(12) United States Patent
Lu et al.

(10) Patent No.: US 9,586,947 B2
(45) Date of Patent: Mar. 7, 2017

(54) IMIDAZOLINE DERIVATIVES, PREPARATION METHODS THEREOF, AND THEIR APPLICATIONS IN MEDICINE

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Hejun Lu, Shanghai (CN); Piaoyang Sun, Lianyungang (CN); Hongbo Fei, Shanghai (CN); Hongjian Jiang, Shanghai (CN); Haowei Wang, Shanghai (CN); Qing Dong, Shanghai (CN)

(73) Assignees: Shanghai Hengrui Pharmaceutical Co., Ltd., Shanghai (CN); Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/425,207

(22) PCT Filed: Aug. 26, 2013

(86) PCT No.: PCT/CN2013/082273
§ 371 (c)(1),
(2) Date: Mar. 2, 2015

(87) PCT Pub. No.: WO2014/036897
PCT Pub. Date: Mar. 13, 2014

(65) Prior Publication Data
US 2015/0225381 A1    Aug. 13, 2015

(30) Foreign Application Priority Data

Sep. 4, 2012    (CN) .......................... 2012 1 0323870

(51) Int. Cl.
| | | |
|---|---|---|
| *C07D 233/86* | (2006.01) |
| *C07D 409/12* | (2006.01) |
| *C07D 403/12* | (2006.01) |
| *C07D 405/14* | (2006.01) |
| *C07D 405/12* | (2006.01) |
| *C07D 401/04* | (2006.01) |
| *C07D 401/12* | (2006.01) |

(52) U.S. Cl.
CPC ......... *C07D 409/12* (2013.01); *C07D 233/86* (2013.01); *C07D 401/04* (2013.01); *C07D 401/12* (2013.01); *C07D 403/12* (2013.01); *C07D 405/12* (2013.01); *C07D 405/14* (2013.01)

(58) Field of Classification Search
CPC .................................................. C07D 233/86
USPC ....................................... 548/319.1; 514/391
See application file for complete search history.

(56) References Cited

U.S. PATENT DOCUMENTS

| 7,709,517 B2 * | 5/2010 | Sawyers ............... C07D 233/70 |
| | | 514/385 |
| 2003/0153752 A1 | 8/2003 | Hirst et al. |
| 2006/0025589 A1 * | 2/2006 | Binet .................. C07D 233/86 |
| | | 544/139 |
| 2012/0110702 A1 | 5/2012 | Yap et al. |

FOREIGN PATENT DOCUMENTS

| CN | 101048381 A | 10/2007 |
| CN | 101817787 A | 9/2010 |
| EP | 1466898 A1 | 10/2004 |
| WO | 2008/001931 A2 | 1/2008 |
| WO | 2010092371 A1 | 8/2010 |
| WO | 2010118354 A1 | 10/2010 |
| WO | 2011008543 A2 | 1/2011 |
| WO | 2011/103196 A1 | 8/2011 |
| WO | 2012011840 A1 | 1/2012 |
| WO | 2012015723 A1 | 2/2012 |
| WO | 2012050868 A1 | 4/2012 |
| WO | 2012119559 A1 | 9/2012 |

OTHER PUBLICATIONS

Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1996.*
Int'l Search Report issued on Dec. 5, 2013 in Int'l Application No. PCT/CN2013/082273.

* cited by examiner

*Primary Examiner* — Patricia L Morris
(74) *Attorney, Agent, or Firm* — Panitch Schwarze Belisario & Nadel LLP

(57) ABSTRACT

New imidazoline derivatives represented by formula (I):

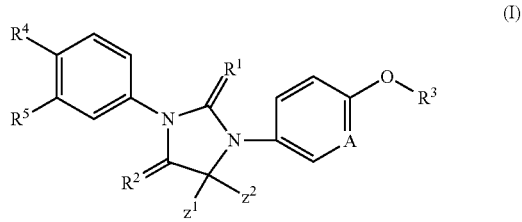

preparation methods thereof, pharmaceutical compositions comprising such derivatives, and applications of such derivatives in preparing androgen receptor antagonists and medicaments for treating diseases such as prostate cancer are described.

21 Claims, No Drawings

US 9,586,947 B2

IMIDAZOLINE DERIVATIVES, PREPARATION METHODS THEREOF, AND THEIR APPLICATIONS IN MEDICINE

CROSS-REFERENCE TO RELATED APPLICATIONS

This application is a Section 371 of International Application No. PCT/CN2013/082273, filed on Aug. 26, 2013, which was published in the Chinese language on Mar. 13, 2014, under International Publication No. WO 2014/036897 A1, and the disclosure of which is incorporated herein by reference.

FIELD OF THE INVENTION

The present invention relates to imidazoline derivatives, preparation processes, pharmaceutical compositions containing the same, and their use as a therapeutic agent, particularly as an androgen receptor (AR) inhibitor, and in the preparation of a medicament for the treatment and prevention of prostate cancer, etc.

BACKGROUND OF THE INVENTION

Prostate cancer is the most common cancer in western males, and is the third leading cause of cancer mortality due to a high incidence rate. Based on global estimates, prostate cancer accounted for more than 900,000 of total cases (only a little lower than lung cancer and bronchiolar carcinoma (1,095,200)) and nearly 260,000 deaths (approximately 6% of the total cancer deaths) in men in 2008. In curable early stages, prostate cancer in situ can be diagnosed by prostate-specific antigen (PSA) test and cured via surgical excision or radiotherapy. Most prostate cancer patients respond to androgen deprivation therapy (ADT) in a certain period. The mechanism of ADT is to block or decrease the activity of androgen receptors (AR) by reducing the androgen level, thereby inhibiting the activation of the androgen-dependent signaling pathway. However, almost all patients have progressed to "castration-resistant prostate cancer" (CRPC).

Functional androgen receptor (AR) signaling is necessary for the development of prostate cancer. AR signaling is absent or weak in androgen insensitivity syndrome and spinal and bulbar muscular atrophy patients, which results in underdeveloped prostates that do not produce carcinomas. It has become clear that AR expression and signaling remains intact as the disease evolves from androgen-sensitive cancer to hormone refractory prostate cancer (HRPC). Genetic and epigenetic changes mean that prostate tumors continue to rely on AR growth signaling, and they thus remain targets of 'hormonal' therapy. The development of new strategies and new drugs that more effectively abrogate AR signaling will probably result in important clinical benefits.

The AR, the gene for which is located on chromosome Xq11-12, is a member of the steroid hormone receptor family of ligand-activated nuclear transcription factors. The AR contains four functional regions: an amino terminal regulatory domain (AF-1 site), a DNA-binding domain composed of two zinc fingers, a hinge region containing a nuclear localization signal, and a carboxy-terminal ligand-binding domain (AF-2 site). Unligated ARs are located primarily in the cytoplasm, and are bound to heat shock proteins (HSPs) 90, 70, 56, and 23, which stabilize the ARs' tertiary structure in a conformation that permits androgen binding. Androgen binds to the AR, results in dissociation of HSPs from the AR, causing dimerization of the AR and subsequent tyrosine kinase phosphorylation, resulting in translocation of the AR to the nucleus. Once inside the nucleus, the AR binds to androgen response elements located in the promoter and enhancer regions of target genes, resulting in concomitant recruitment of co-regulatory proteins and formation of an active transcription complex. Co-regulatory proteins form a bridge between the AR, the preinitiation complex, and RNA poly-merase; coactivators facilitate transcription by recruiting protein complexes to DNA that alter the chromatin structure to a more transcriptionally active form, and co-repressors mediate chromatin condensation and silence transcription.

AR gene amplification has been reported in 25%-30% of patients with HRPC but is present at very low rates (1-2%) in those with primary prostate cancer, indicating that AR gene amplification is related to the development of HRPC. AR gene amplification highlights the strong selective pressure for continued AR signaling as tumors evolve in androgen-deprived environments, and provides the impetus for the development of more effective inhibition of AR signaling. Point mutations in AR can result in altered ligand specificity such that mutated ARs can be activated by non-androgenic ligands such as anti-androgens.

Bicalutamide (trade name: Casodex) is the most commonly used anti-androgen drug, which inhibits AR in hormone-sensitive prostate cancer. However, Bicalutamide cannot effectively inhibit AR activity when the cancer becomes hormone-resistant. Novel AR antagonist MDV-3100, developed by Medivation Inc., can effectively suppress the combination of androgen and AR protein, and block translocation of AR to the nucleus and recruitment of coactivators of the ligand-receptor complex. So far, none have found that MDV-3100 would become an agonist and promote cancer development in AR-overexpressed tumors. In May 21, 2012, MDV-3100 entered into the pre-registration stage.

Up to now, a series of AR antagonists have been disclosed by some patent applications, including PCT Patent Application Publications WO 2010/092371, WO 2011/008543, WO 2012/011840, and WO 2012/015723, etc.

Although a series of AR antagonists for treating prostate cancer has been disclosed, there remains a need to develop new compounds with better efficacy. After continuous efforts, the present invention provides compounds of formula (I), and shows that the compounds having such structure exhibit excellent effects and actions.

SUMMARY OF THE INVENTION

The present invention is directed to providing a compound of formula (I), a tautomer, mesomer, racemate, enantiomer, or diastereomer thereof, or a mixture thereof, and a pharmaceutically acceptable salt thereof, as well as a metabolite, metabolic precursor, or prodrug thereof:

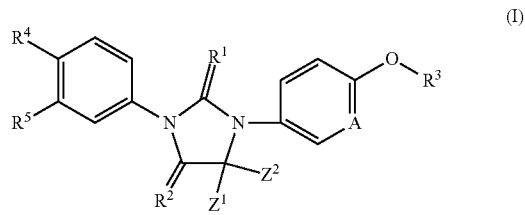

(I)

wherein:

A is —CR' or N;

R' is hydrogen, halogen, alkyl, cycloalkyl or heterocyclyl, wherein said alkyl, cycloalkyl, and heterocyclyl are each optionally substituted with one or more groups selected from the group consisting of halogen, cyano, hydroxy, alkyl, alkoxy, carboxyl, and carboxylic ester;

$Z^1$ and $Z^2$ are each independently alkyl, or $Z^1$ and $Z^2$ are taken together with the attached carbon atoms to form one cycloalkyl or heterocyclyl;

$R^1$ and $R^2$ are each independently selected from the group consisting of S and O;

$R^3$ is selected from the group consisting of alkyl, alkenyl, alkynyl, cycloalkyl, heterocyclyl, aryl, heteroaryl, and —S(O)$_m$R$^6$, wherein the alkenyl, alkynyl, cycloalkyl, heterocyclyl, aryl and heteroaryl are each optionally substituted with one or more groups selected from the group consisting of halogen, cyano, amino, alkyl, haloalkyl, hydroxyalkyl, cycloalkyl, heterocyclyl, aryl, heteroaryl, —OR$^6$, —C(O)NR$^7$R$^8$, —S(O)$_m$R$^6$, —C(O)R$^6$, —OC(O)R$^6$, —NR$^7$C(O)R$^8$, —NR$^7$C(O)OR$^8$, and —C(O)OR$^6$; wherein the alkyl is optionally substituted with one or more groups selected from the group consisting of halogen, cyano, amino, cycloalkyl, heterocyclyl, aryl, heteroaryl, —OR$^6$, —C(O)NR$^7$R$^8$, —S(O)$_m$R$^6$, —C(O)R$^6$, —OC(O)R$^6$, —NR$^7$C(O)R$^8$, —NR$^7$C(O)OR$^8$, and —C(O)OR$^6$, wherein the cycloalkyl, heterocyclyl, aryl, and heteroaryl are each optionally substituted with one or more groups selected from the group consisting of halogen, cyano, amino, alkyl, haloalkyl, hydroxyalkyl, cycloalkyl, heterocyclyl, aryl, heteroaryl, —OR$^6$, —C(O)NR$^7$R$^8$, —S(O)$_m$R$^6$, —C(O)R$^6$, —OC(O)R$^6$, —NR$^7$C(O)R$^8$, —NR$^7$C(O)OR$^8$, and —C(O)OR$^6$;

$R^4$ and $R^5$ are each independently selected from the group consisting of cyano, nitro, alkyl, haloalkyl, hydroxy, hydrogen, alkoxy, and haloalkoxy;

$R^6$ is hydrogen, alkyl, alkenyl, alkynyl, hydroxy, halogen, alkoxy, cycloalkyl, heterocyclyl, aryl, or heteroaryl, wherein the alkyl, alkoxy, cycloalkyl, heterocyclyl, aryl, and heteroaryl are each optionally substituted with one or more groups selected from the group consisting of halogen, cyano, hydroxy, amino, oxo, alkyl, haloalkyl, hydroxyalkyl, alkoxy, cycloalkyl, heterocyclyl, aryl, heteroaryl, carboxyl, and carboxylic ester;

$R^7$ and $R^8$ are each independently selected from the group consisting of hydrogen, alkyl, cycloalkyl, heterocyclyl, aryl, and heteroaryl, wherein the alkyl, cycloalkyl, heterocyclyl, aryl or heteroaryl is each optionally substituted with one or more groups selected from the group consisting of halogen, cyano, hydroxy, amino, oxo, alkyl, haloalkyl, hydroxyalkyl, alkoxy, cycloalkyl, heterocyclyl, aryl, heteroaryl, carboxyl, and carboxylic ester; and m is 0, 1, or 2.

In an embodiment of the invention, a compound of formula (I) or a tautomer, mesomer, racemate, enantiomer, diastereomer, or mixture thereof, or a pharmaceutically acceptable salt thereof, is selected from a compound of formula (II) or a tautomer, mesomer, racemate, enantiomer, diastereomer, or mixture thereof, or a pharmaceutically acceptable salt thereof:

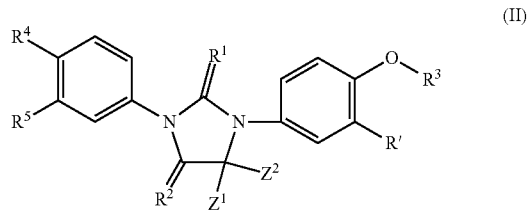

(II)

wherein R' is hydrogen or halogen, and $Z^1$, $Z^2$, $R^1$ to $R^5$ are as defined in formula (I).

In another embodiment of the invention, in the compound of formula (I) or a tautomer, mesomer, racemate, enantiomer, diastereomer, or mixture thereof, or a pharmaceutically acceptable salt thereof, A is N.

In another embodiment of the invention, in the compound of formula (I) or a tautomer, mesomer, racemate, enantiomer, diastereomer, or mixture thereof, or a pharmaceutically acceptable salt thereof, A is —CR', and R' is halogen.

In another embodiment of the invention, in the compound of formula (I) or a tautomer, mesomer, racemate, enantiomer, diastereomer, or mixture thereof, or a pharmaceutically acceptable salt thereof, $R^1$ is S.

In another embodiment of the invention, in the compound of formula (I) or a tautomer, mesomer, racemate, enantiomer, diastereomer, or mixture thereof, or a pharmaceutically acceptable salt thereof, $R^2$ is O.

In another embodiment of the invention, in the compound of formula (I) or a tautomer, mesomer, racemate, enantiomer, diastereomer, or mixture thereof, or a pharmaceutically acceptable salt thereof, $Z^1$ and $Z^2$ are each independently methyl.

In another embodiment of the invention, in the compound of formula (I) or a tautomer, mesomer, racemate, enantiomer, diastereomer, or mixture thereof, or a pharmaceutically acceptable salt thereof, $R^4$ is cyano.

In another embodiment of the invention, in the compound of formula (I) or a tautomer, mesomer, racemate, enantiomer, diastereomer, or mixture thereof, or a pharmaceutically acceptable salt thereof, $R^5$ is haloalkyl.

In another embodiment of the invention, in the compound of formula (I) or a tautomer, mesomer, racemate, enantiomer, diastereomer, or mixture thereof, or a pharmaceutically acceptable salt thereof, $R^5$ is trifluoromethyl.

In another embodiment of the invention, in the compound of formula (I) or a tautomer, mesomer, racemate, enantiomer, diastereomer, or mixture thereof, or a pharmaceutically acceptable salt thereof, $R^3$ is selected from the group consisting of alkyl, cycloalkyl, heterocyclyl, aryl, and heteroaryl, wherein the cycloalkyl, heterocyclyl, aryl, and heteroaryl are each optionally substituted with one or more groups selected from the group consisting of halogen, amino, alkyl, —OR$^6$, —C(O)NR$^7$R$^8$, —S(O)$_m$R$^6$, —C(O)R$^6$, and —C(O)OR$^6$, wherein the alkyl is optionally substituted with one or more groups selected from the group consisting of halogen, cyano, amino, cycloalkyl, heterocyclyl, aryl, heteroaryl, —OR$^6$, —C(O)NR$^7$R$^8$, —S(O)$_m$R$^6$, and —C(O)OR$^6$, wherein the cycloalkyl, heterocyclyl, aryl, and heteroaryl are each optionally substituted with one or more groups selected from the group consisting of halogen, cyano, amino, alkyl, haloalkyl, hydroxyalkyl, cycloalkyl, heterocyclyl, aryl, heteroaryl, —OR$^6$, —C(O)NR$^7$R$^8$, —S(O)$_m$R$^6$, and —C(O)OR$^6$;

R⁶, R⁷, and R⁸ are each independently selected from the group consisting of hydrogen and alkyl, wherein the alkyl is optionally substituted with one or more groups selected from the group consisting of halogen, cyano, hydroxy, amino, oxo, alkyl, and haloalkyl; and m is 2.

In another embodiment of the invention, in the compound of formula (I) or a tautomer, mesomer, racemate, enantiomer, diastereomer, or mixture thereof, or a pharmaceutically acceptable salt thereof, R³ is alkyl, wherein the alkyl is substituted with one or more groups selected from the group consisting of halogen, cyano, amino, cycloalkyl, heterocyclyl, aryl, heteroaryl, —OR⁶, —C(O)NR⁷R⁸, —S(O)ₘR⁶, and —C(O)OR⁶;

R⁶, R⁷, and R⁸ are each independently selected from the group consisting of hydrogen and alkyl, wherein the alkyl is each optionally substituted with one or more groups selected from the group consisting of halogen, cyano, hydroxy, amino, oxo, alkyl, and haloalkyl; and m is 2.

In another embodiment of the invention, in the compound of formula (I) or a tautomer, mesomer, racemate, enantiomer, diastereomer, or mixture thereof, or a pharmaceutically acceptable salt thereof, R³ is alkyl, wherein the alkyl is substituted with one or more hydroxy groups.

In another embodiment of the invention, in the compound of formula (I) or a tautomer, mesomer, racemate, enantiomer, diastereomer, or mixture thereof, or a pharmaceutically acceptable salt thereof, R³ is heterocyclyl, wherein the heterocyclyl is optionally substituted with one or more groups selected from the group consisting of halogen, amino, alkyl, —OR⁶, —C(O)NR⁷R⁸, —S(O)ₘR⁶, —C(O)R⁶, and —C(O)OR⁶;

R⁶, R⁷, and R⁸ are each independently selected from the group consisting of hydrogen and alkyl; and m is 2.

Typical compounds of the present invention include, but are not limited to the following:

| Example No. | Structure and Name |
|---|---|
| 1 | 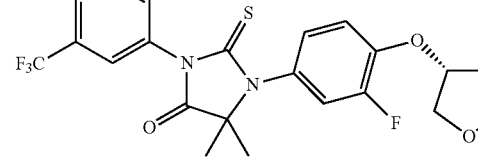<br>(R)-4-(3-(3-fluoro-4-((tetrahydrofuran-3-yl)oxy)phenyl)-4,4-dimethyl-5-oxo-2-thioxoimidazolidin-1-yl)-2-(trifluoromethyl)benzonitrile |
| 2 | 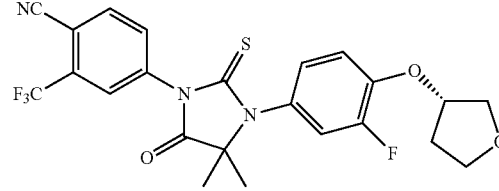 [SMILES: CC1(C)C(=O)N(c2ccc(C#N)c(C(F)(F)F)c2)C(=S)N1c1ccc(O[C@@H]2CCOC2)c(F)c1]<br>(S)-4-(3-(3-fluoro-4-((tetrahydrofuran-3-yl)oxy)phenyl)-4,4-dimethyl-5-oxo-2-thioxoimidazolidin-1-yl)-2-(trifluoromethyl)benzonitrile |
| 3 | 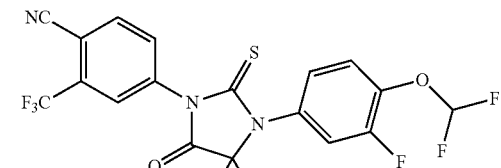<br>4-(3-(4-(difluoromethoxy)-3-fluorophenyl)-4,4-dimethyl-5-oxo-2-thioxoimidazolidin-1-yl)-2-(trifluoromethyl)benzonitrile |
| 4 | 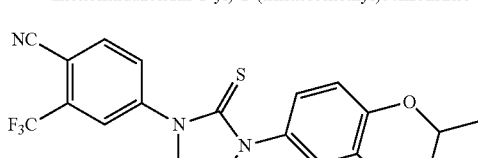<br>4-(3-(3-fluoro-4-((tetrahydro-2H-pyran-4-yl)oxy)phenyl)-4,4-dimethyl-5-oxo-2-thioxoimidazolidin-1-yl)-2-(trifluoromethyl)benzonitrile |

-continued

| Example No. | Structure and Name |
|---|---|
| 5 | 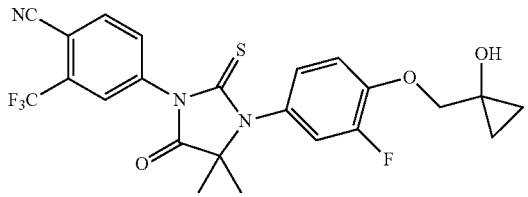 [SMILES: CC1(C)C(=O)N(c2ccc(C#N)c(C(F)(F)F)c2)C(=S)N1c1ccc(OCC2(O)CC2)c(F)c1] 4-(3-(3-fluoro-4-((1-hydroxycyclopropyl)methoxy)phenyl)-4,4-dimethyl-5-oxo-2-thioxoimidazolidin-1-yl)-2-(trifluoromethyl)benzonitrile |
| 6 | 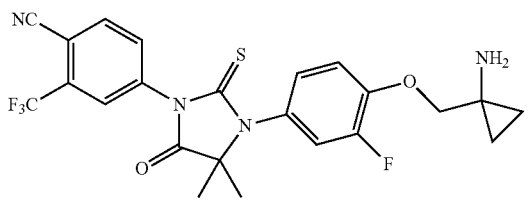 [SMILES: CC1(C)C(=O)N(c2ccc(C#N)c(C(F)(F)F)c2)C(=S)N1c1ccc(OCC2(N)CC2)c(F)c1] 4-(3-(4-((1-aminocyclopropyl)methoxy)-3-fluorophenyl)-4,4-dimethyl-5-oxo-2-thioxoimidazolidin-1-yl)-2-(trifluoromethyl)benzonitrile |
| 7 | 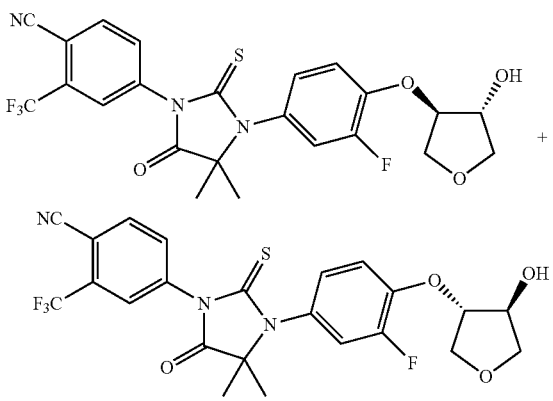 4-(3-(3-fluoro-4-(((3R,4R/3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile |
| 8 | 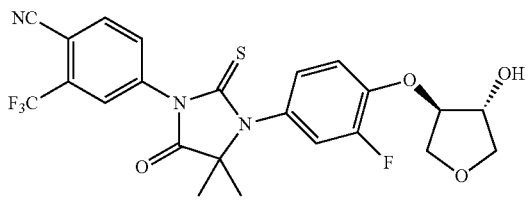 [SMILES: CC1(C)C(=O)N(c2ccc(C#N)c(C(F)(F)F)c2)C(=S)N1c1ccc(O[C@@H]2COC[C@H]2O)c(F)c1] 4-(3-(3-fluoro-4-(((3R,4R)-4-hydroxytetrahydrofuran-3-yl)oxy)phenyl)-4,4-dimethyl-5-oxo-2-thioxoimidazolidin-1-yl)-2-(trifluoromethyl)benzonitrile |
| 9 | 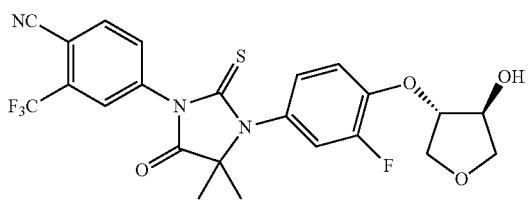 [SMILES: CC1(C)C(=O)N(c2ccc(C#N)c(C(F)(F)F)c2)C(=S)N1c1ccc(O[C@H]2COC[C@@H]2O)c(F)c1] 4-(3-(3-fluoro-4-(((3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile |

| Example No. | Structure and Name |
|---|---|
| 10 | 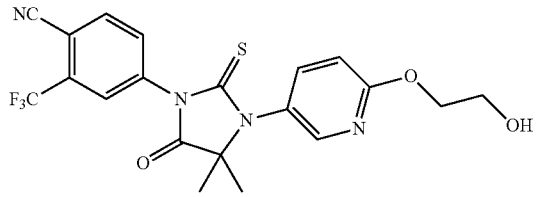 [SMILES: CC1(C)C(=O)N(c2ccc(C#N)c(C(F)(F)F)c2)C(=S)N1c1ccc(OCCO)nc1]
4-(3-(6-(2-hydroxyethoxy)pyridin-3-yl)-4,4-dimethyl-5-oxo-2-thioxoimidazolidin-1-yl)-2-(trifluoromethyl)benzonitrile |
| 11 | 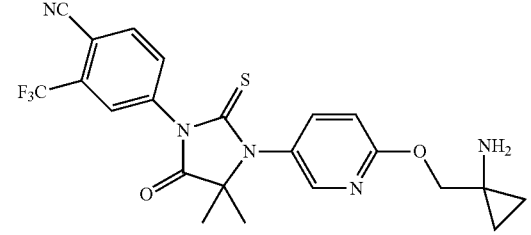 [SMILES: CC1(C)C(=O)N(c2ccc(C#N)c(C(F)(F)F)c2)C(=S)N1c1ccc(OCC2(N)CC2)nc1]
4-(3-(6-((1-aminocyclopropyl)methoxy)pyridin-3-yl)-4,4-dimethyl-5-oxo-2-thioxoimidazolidin-1-yl)-2-(trifluoromethyl)benzonitrile |
| 12 | 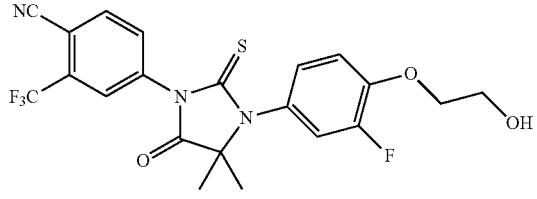 [SMILES: CC1(C)C(=O)N(c2ccc(C#N)c(C(F)(F)F)c2)C(=S)N1c1ccc(OCCO)c(F)c1]
4-(3-(3-fluoro-4-(2-hydroxyethoxy)phenyl)-4,4-dimethyl-5-oxo-2-thioxoimidazolidin-1-yl)-2-(trifluoromethyl)benzonitrile |
| 13 | 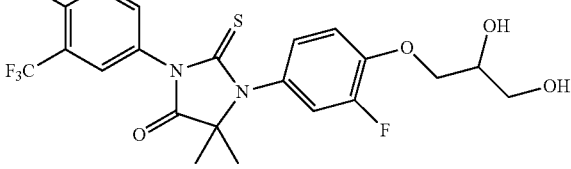
4-(3-(4-(2,3-dihydroxypropoxy)-3-fluorophenyl)-4,4-dimethyl-5-oxo-2-thioxoimidazolidin-1-yl)-2-(trifluoromethyl)benzonitrile |
| 14 | 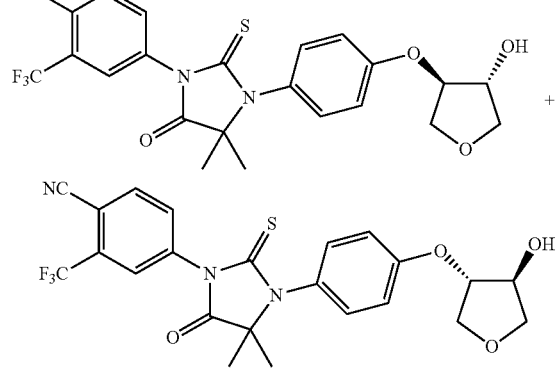
4-(3-(4-(((3R,4R/3S,4S)-4-hydroxytetrahydrofuran-3-yl)oxy)phenyl)-4,4-dimethyl-5-oxo-2-thioxoimidazlidin-1-yl)-2-(trifluoromethyl)benzonitrile |

| Example No. | Structure and Name |
|---|---|
| 15 | 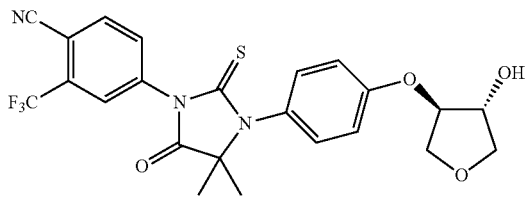 [SMILES: CC1(C)C(=O)N(c2ccc(C#N)c(C(F)(F)F)c2)C(=S)N1c1ccc(O[C@@H]2COC[C@H]2O)cc1]<br>4-(3-(4-(((3R,4R)-4-hydroxytetrahydrofuran-3-yl)oxy)phenyl)-4,4-dimethyl-5-oxo-2-thioxoimidazolidin-1-yl)-2-(trifluoromethyl)benzonitrile |
| 16 | 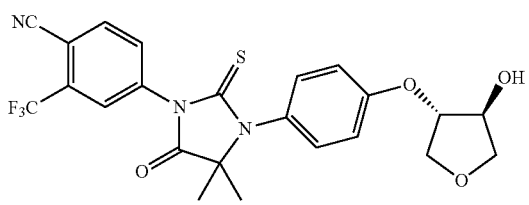 [SMILES: CC1(C)C(=O)N(c2ccc(C#N)c(C(F)(F)F)c2)C(=S)N1c1ccc(O[C@H]2COC[C@@H]2O)cc1]<br>4-(3-(4-((((3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile |
| 17 | 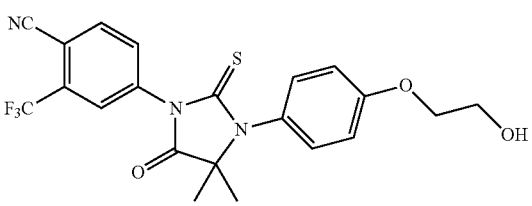 [SMILES: CC1(C)C(=O)N(c2ccc(C#N)c(C(F)(F)F)c2)C(=S)N1c1ccc(OCCO)cc1]<br>4-(3-(4-(2-hydroxyethoxy)phenyl)-4,4-dimethyl-5-oxo-2-thioxoimidazolidin-1-yl)-2-(trifluoromethyl)benzonitrile |
| 18 | 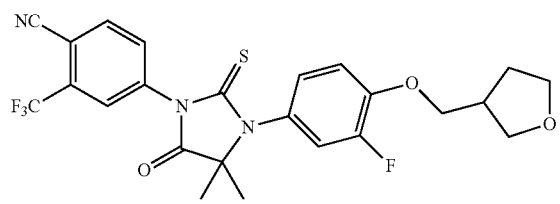 [SMILES: CC1(C)C(=O)N(c2ccc(C#N)c(C(F)(F)F)c2)C(=S)N1c1ccc(OCC2CCOC2)c(F)c1]<br>4-(3-(3-fluoro-4-((tetrahydrofuran-3-yl)methoxy)phenyl)-4,4-dimethyl-5-oxo-2-thioxoimidazolidin-1-yl)-2-(trifluoromethyl)benzonitrile |
| 19 | 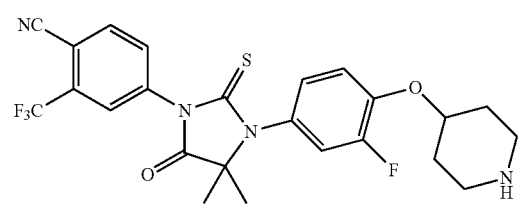 [SMILES: CC1(C)C(=O)N(c2ccc(C#N)c(C(F)(F)F)c2)C(=S)N1c1ccc(OC2CCNCC2)c(F)c1]<br>4-(3-(3-fluoro-4-((piperidin-4-yl)oxy)phenyl)-4,4-dimethyl-5-oxo-2-thioxoimidazolidin-1-yl)-2-(trifluoromethyl)benzonitrile |

| Example No. | Structure and Name |
|---|---|
| 20 | 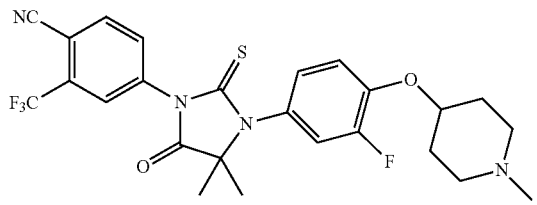 [SMILES: CN1CCC(Oc2ccc(N3C(=S)N(c4ccc(C#N)c(C(F)(F)F)c4)C(=O)C3(C)C)cc2F)CC1]<br>4-(3-(3-fluoro-4-((1-methylpiperidin-4-yl)oxy)phenyl)-4,4-dimethyl-5-oxo-2-thioxoimidazolidin-1-yl)-2-(trifluoromethyl)benzonitrile |
| 21 | 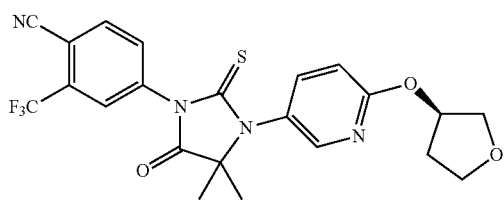 [SMILES: CC1(C)C(=O)N(c2ccc(C#N)c(C(F)(F)F)c2)C(=S)N1c1ccc(O[C@@H]2CCOC2)nc1]<br>(R)-4-(4,4-dimethyl-5-oxo-3-(6-((tetrahydrofuran-3-yl)oxy)pyridin-3-yl)-2-thioxoimidazolidin-1-yl)-2-(trifluoromethyl)benzonitrile |
| 22 | 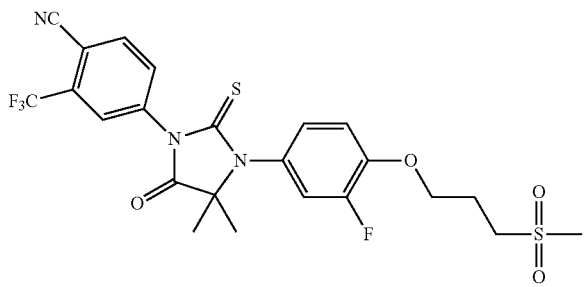 [SMILES: CC1(C)C(=O)N(c2ccc(C#N)c(C(F)(F)F)c2)C(=S)N1c1ccc(OCCCS(C)(=O)=O)c(F)c1]<br>4-(3-(3-fluoro-4-(3-(methylsulfonyl)propoxy)phenyl)-4,4-dimethyl-5-oxo-2-thioxoimidazolidin-1-yl)-2-(trifluoromethyl)benzonitrile |
| 23 | 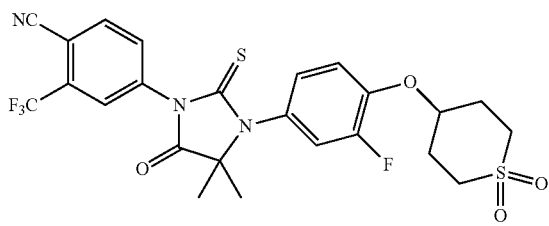 [SMILES: CC1(C)C(=O)N(c2ccc(C#N)c(C(F)(F)F)c2)C(=S)N1c1ccc(OC2CCS(=O)(=O)CC2)c(F)c1]<br>4-(3-(4-((1,1-dioxidotetrahydro-2H-thiopyran-4-yl)oxy)-3-fluorophenyl)-4,4-dimethyl-5-oxo-2-thioxoimidazolidin-1-yl)-2-(trifluoromethyl)benzonitrile |
| 24 | 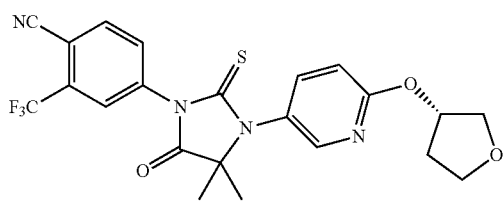 [SMILES: CC1(C)C(=O)N(c2ccc(C#N)c(C(F)(F)F)c2)C(=S)N1c1ccc(O[C@H]2CCOC2)nc1]<br>(S)-4-(4,4-dimethyl-5-oxo-3-(6-((tetrahydrofuran-3-yl)oxy)pyridin-3-yl)-2-thioxoimidazolidin-1-yl)-2-(trifluoromethyl)benzonitrile |

| Example No. | Structure and Name |
|---|---|
| 25 | 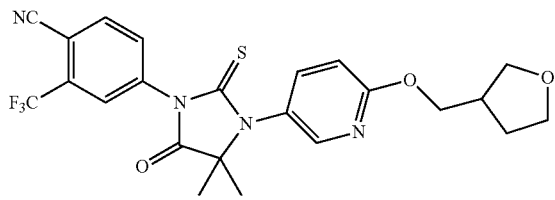 [SMILES: CC1(C)C(=O)N(c2ccc(C#N)c(C(F)(F)F)c2)C(=S)N1c1ccc(OCC2CCOC2)nc1]<br>4-(4,4-dimethyl-5-oxo-3-(6-((tetrahydrofuran-3-yl)methoxy)pyridin-3-yl)-2-thioxoimidazolidin-1-yl)-2-(trifluoromethyl)benzonitrile |
| 26 | 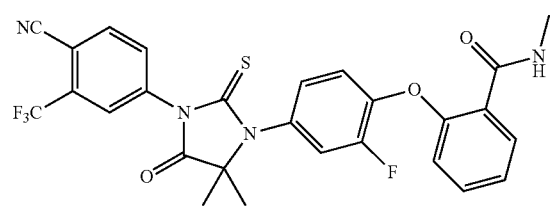 [SMILES: CNC(=O)c1ccccc1Oc1ccc(N2C(=S)N(c3ccc(C#N)c(C(F)(F)F)c3)C(=O)C2(C)C)cc1F]<br>2-(4-(3-(4-cyano-3-(trifluoromethyl)phenyl)-5,5-dimethyl-4-oxo-2-thioxoimidazolidin-1-yl)-2-fluorophenoxy)-N-methylbenzamide |
| 27 | 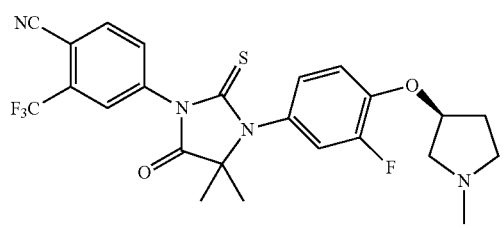 [SMILES: CN1CC[C@H](Oc2ccc(N3C(=S)N(c4ccc(C#N)c(C(F)(F)F)c4)C(=O)C3(C)C)cc2F)C1]<br>(S)-4-(3-(3-fluoro-4-((1-methylpyrrolidin-3-yl)oxy)phenyl)-4,4-dimethyl-5-oxo-2-thioxoimidazolidin-1-yl)-2-(trifluoromethyl)benzonitrile |
| 28 | 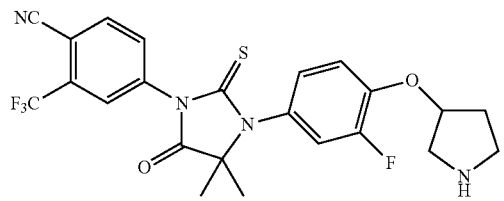 [SMILES: CC1(C)C(=O)N(c2ccc(C#N)c(C(F)(F)F)c2)C(=S)N1c1ccc(OC2CCNC2)c(F)c1]<br>4-(3-(3-fluoro-4-((pyrrolidin-3-yl)oxy)phenyl)-4,4-dimethyl-5-oxo-2-thioxoimidazolidin-1-yl)-2-(trifluoromethyl)benzonitrile |
| 29 | 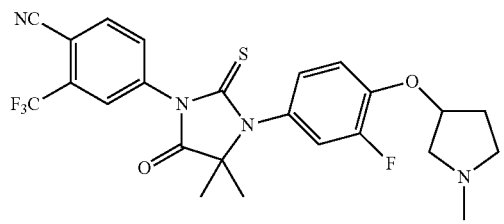 [SMILES: CN1CCC(Oc2ccc(N3C(=S)N(c4ccc(C#N)c(C(F)(F)F)c4)C(=O)C3(C)C)cc2F)C1]<br>4-(3-(3-fluoro-4-((1-methylpyrrolidin-3-yl)oxy)phenyl)-4,4-dimethyl-5-oxo-2-thioxoimidazolidin-1-yl)-2-(trifluoromethyl)benzonitrile |

-continued

| Example No. | Structure and Name |
|---|---|
| 30 | 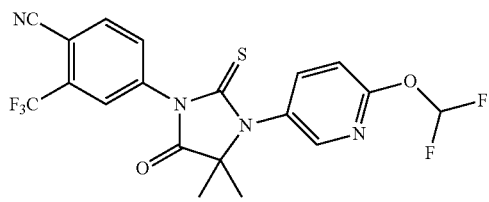 [SMILES: CC1(C)C(=O)N(c2ccc(C#N)c(C(F)(F)F)c2)C(=S)N1c1ccc(OC(F)F)nc1]

4-(3-(6-(difluoromethoxy)pyridin-3-yl)-4,4-dimethyl-5-oxo-2-thioxoimidazolidin-1-yl)-2-(trifluoromethyl)benzonitrile |
| 31 | 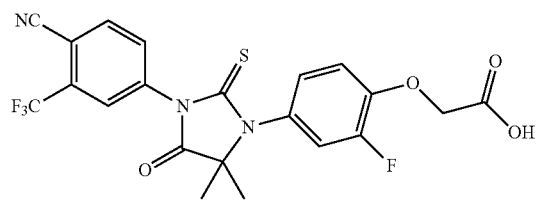 [SMILES: CC1(C)C(=O)N(c2ccc(C#N)c(C(F)(F)F)c2)C(=S)N1c1ccc(OCC(=O)O)c(F)c1]

2-(4-(3-(4-cyano-3-(trifluoromethyl)phenyl)-5,5-dimethyl-4-oxo-2-thioxoimidazolidin-1-yl)-2-fluorophenoxy)acetic acid |
| 32 | 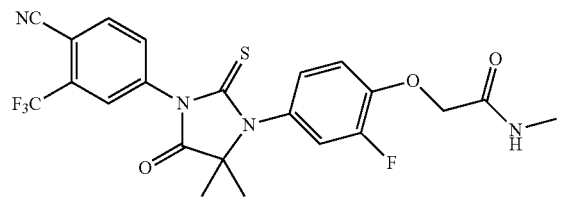 [SMILES: CNC(=O)COc1ccc(N2C(=S)N(c3ccc(C#N)c(C(F)(F)F)c3)C(=O)C2(C)C)cc1F]

2-(4-(3-(4-cyano-3-(trifluoromethyl)phenyl)-5,5-dimethyl-4-oxo-2-thioxoimidazolidin-1-yl)-2-fluorophenoxy)-N-methylacetamide |
| 33 | 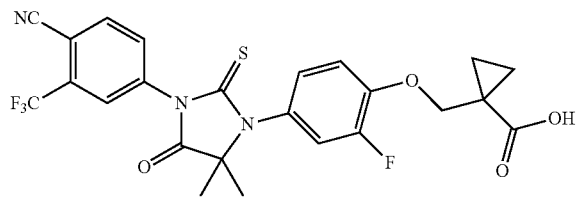 [SMILES: CC1(C)C(=O)N(c2ccc(C#N)c(C(F)(F)F)c2)C(=S)N1c1ccc(OCC2(C(=O)O)CC2)c(F)c1]

1-((4-(3-(4-cyano-3-(trifluoromethyl)phenyl)-5,5-dimethyl-4-oxo-2-thioxoimidazolidin-1-yl)-2-fluorophenoxy)methyl)cyclopropanecarboxylic acid |
| 34 | 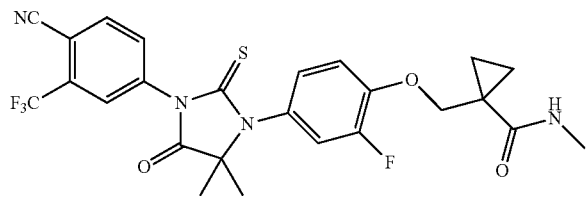 [SMILES: CNC(=O)C1(COc2ccc(N3C(=S)N(c4ccc(C#N)c(C(F)(F)F)c4)C(=O)C3(C)C)cc2F)CC1]

1-((4-(3-(4-cyano-3-(trifluoromethyl)phenyl)-5,5-dimethyl-4-oxo-2-thioxoimidazolidin-1-yl)-2-fluorophenoxy)methyl)-N-methylcyclopropanecarboxamide |

| Example No. | Structure and Name |
|---|---|
| 35 | 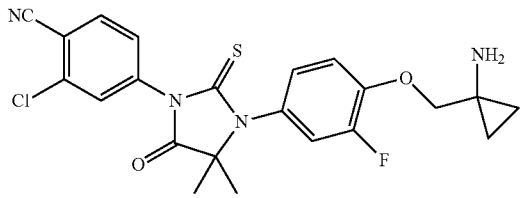 [SMILES: CC1(C)C(=O)N(c2ccc(C#N)c(Cl)c2)C(=S)N1c1ccc(OCC2(N)CC2)c(F)c1]<br>4-(3-(4-((1-aminocyclopropyl)methoxy)-3-fluorophenyl)-4,4-dimethyl-5-oxo-2-thioxoimidazolidin-1-yl)-2-chlorobenzonitrile |
| 36 | 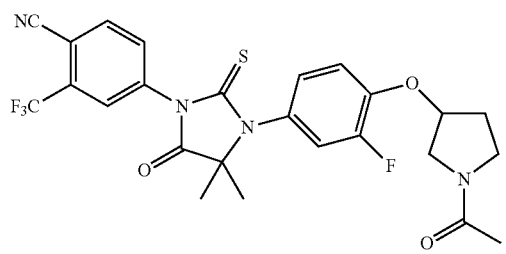 [SMILES: CC(=O)N1CCC(Oc2ccc(N3C(=S)N(c4ccc(C#N)c(C(F)(F)F)c4)C(=O)C3(C)C)cc2F)C1]<br>4-(3-(4-((1-acetylpyrrolidin-3-yl)oxy)-3-fluorophenyl)-4,4-dimethyl-5-oxo-2-thioxoimidazolidin-1-yl)-2-(trifluoromethyl)benzonitrile |
| 37 | 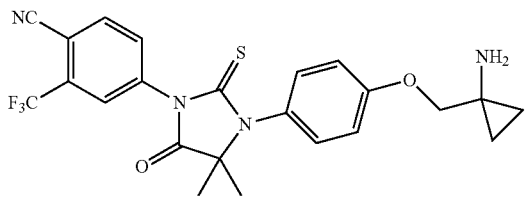 [SMILES: CC1(C)C(=O)N(c2ccc(C#N)c(C(F)(F)F)c2)C(=S)N1c1ccc(OCC2(N)CC2)cc1]<br>4-(3-(4-((1-aminocyclopropyl)methoxy)phenyl)-4,4-dimethyl-5-oxo-2-thioxoimidazolidin-1-yl)-2-(trifluoromethyl)benzonitrile |
| 38 | 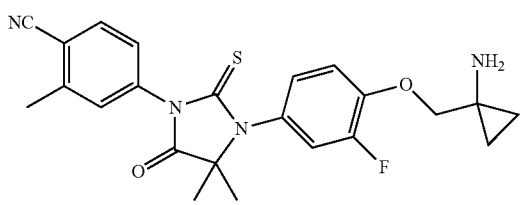 [SMILES: Cc1cc(N2C(=O)C(C)(C)N(c3ccc(OCC4(N)CC4)c(F)c3)C2=S)ccc1C#N]<br>4-(3-(4-((1-aminocyclopropyl)methoxy)-3-fluorophenyl)-4,4-dimethyl-5-oxo-2-thioxoimidazolidin-1-yl)-2-methylbenzonitrile |
| 39 | 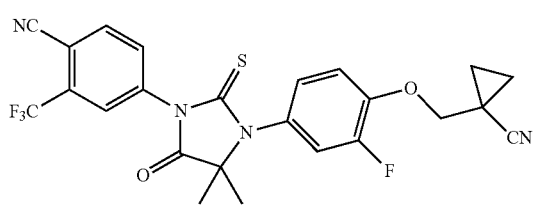 [SMILES: CC1(C)C(=O)N(c2ccc(C#N)c(C(F)(F)F)c2)C(=S)N1c1ccc(OCC2(C#N)CC2)c(F)c1]<br>4-(3-(4-((1-cyanocyclopropyl)methoxy)-3-fluorophenyl)-4,4-dimethyl-5-oxo-2-thioxoimidazolidin-1-yl)-2-(trifluoromethyl)benzonitrile |

| Example No. | Structure and Name |
|---|---|
| 40 | 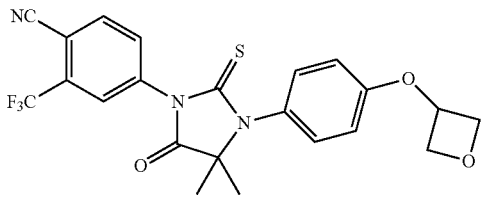 [SMILES: CC1(C)C(=O)N(c2ccc(C#N)c(C(F)(F)F)c2)C(=S)N1c1ccc(OC2COC2)cc1]<br>4-(4,4-dimethyl-3-(4-((oxetan-3-yl)oxy)phenyl)-5-oxo-2-thioxoimidazolidin-1-yl)-2-(trifluoromethyl)benzonitrile |
| 41 | 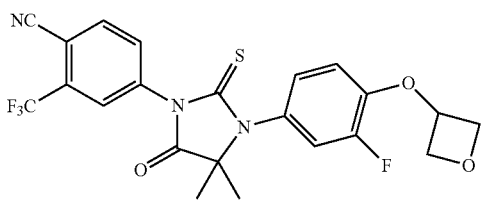 [SMILES: CC1(C)C(=O)N(c2ccc(C#N)c(C(F)(F)F)c2)C(=S)N1c1ccc(OC2COC2)c(F)c1]<br>4-(3-(3-fluoro-4-((oxetan-3-yl)oxy)phenyl)-4,4-dimethyl-5-oxo-2-thioxoimidazolidin-1-yl)-2-(trifluoromethyl)benzonitrile |
| 42 | 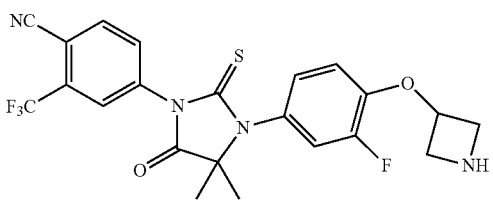 [SMILES: CC1(C)C(=O)N(c2ccc(C#N)c(C(F)(F)F)c2)C(=S)N1c1ccc(OC2CNC2)c(F)c1]<br>4-(3-(4-((azetidin-3-yl)oxy)-3-fluorophenyl)-4,4-dimethyl-5-oxo-2-thioxoimidazolidin-1-yl)-2-(trifluoromethyl)benzonitrile |
| 43 | 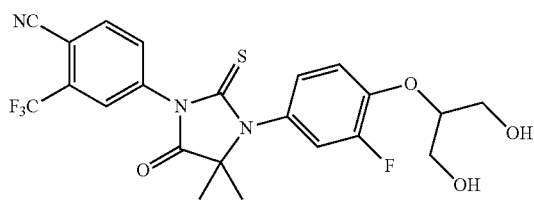 [SMILES: CC1(C)C(=O)N(c2ccc(C#N)c(C(F)(F)F)c2)C(=S)N1c1ccc(OC(CO)CO)c(F)c1]<br>4-(3-(4-((1,3-dihydroxypropan-2-yl)oxy)-3-fluorophenyl)-4,4-dimethyl-5-oxo-2-thioxoimidazolidin-1-yl)-2-(trifluoromethyl)benzonitrile |
| 44 | 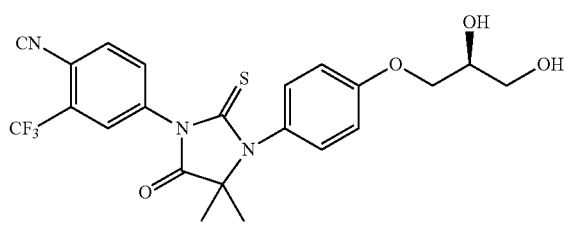<br>(S)-4-(3-(4-(2,3-dihydroxypropoxy)phenyl)-4,4-dimethyl-5-oxo-2-thioxoimidazolidin-1-yl)-2-(trifluoromethyl)benzonitrile |

| Example No. | Structure and Name |
|---|---|
| 45 | 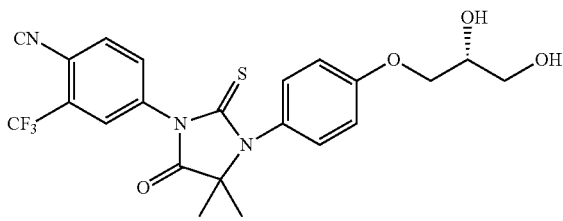<br>(R)-4-(3-(4-(2,3-dihydroxypropoxy)phenyl)-4,4-dimethyl-5-oxo-2-thioxoimidazolidin-1-yl)-2-(trifluoromethyl)benzonitrile |
| 46 | 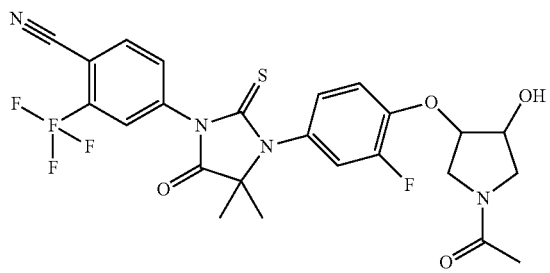<br>4-(3-(4-((1-acetyl-4-hydroxypyrrolidin-3-yl)oxy)-3-fluorophenyl)-4,4-dimethyl-5-oxo-2-thioxoimidazolidin-1-yl)-2-(trifluoromethyl)benzonitrile |
| 47 | 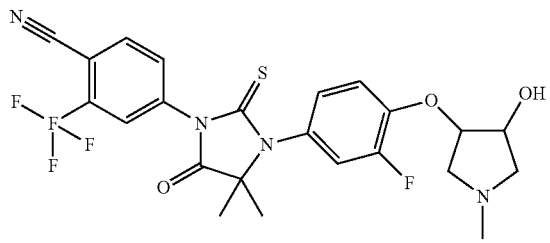<br>4-(3-(3-fluoro-4-((4-hydroxy-1-methylpyrrolidin-3-yl)oxy)phenyl)-4,4-dimethyl-5-oxo-2-thioxoimidazolidin-1-yl)-2-(trifluoromethyl)benzonitrile |
| 48 | 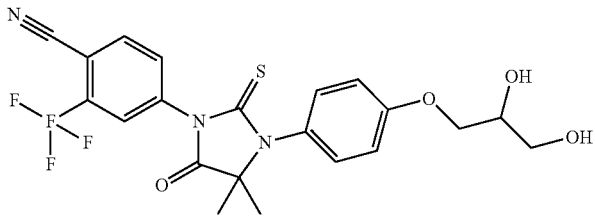<br>4-(3-(4-(2,3-dihydroxypropoxy)phenyl)-4,4-dimethyl-5-oxo-2-thioxoimidazolidin-1-yl)-2-(trifluoromethyl)benzonitrile |
| 49 | 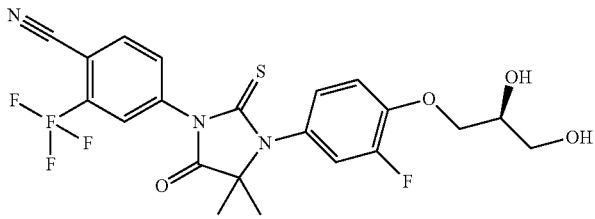<br>(S)-4-(3-(4-(2,3-dihydroxypropoxy)-3-fluorophenyl)-4,4-dimethyl-5-oxo-2-thioxoimidazolidin-1-yl)-2-(trifluoromethyl)benzonitrile |

| Example No. | Structure and Name |
|---|---|
| 50 | 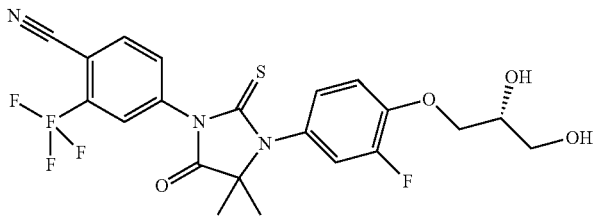
(R)-4-(3-(4-(2,3-dihydroxypropoxy)-3-fluorophenyl)-4,4-dimethyl-5-oxo-2-thioxoimidazolidin-1-yl)-2-(trifluoromethyl)benzonitrile |
| 51 | 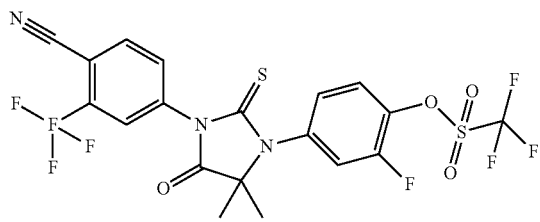
4-(3-(4-cyano-3-(trifluoromethyl)phenyl)-5,5-dimethyl-4-oxo-2-thioxoimidazolidin-1-yl)-2-fluorophenyl trifluoromethanesulfonate |
| 11a | 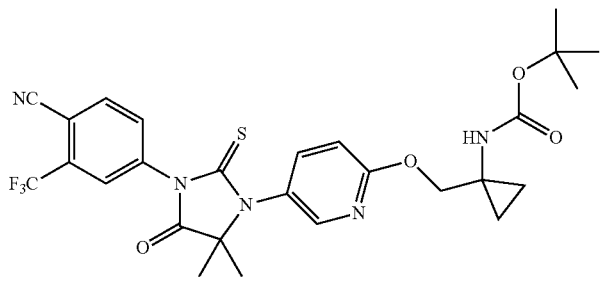 [SMILES: CC(C)(C)OC(=O)NC1(COc2ccc(N3C(=S)N(c4ccc(C#N)c(C(F)(F)F)c4)C(=O)C3(C)C)cn2)CC1]
tert-butyl (1-(((5-(3-(4-cyano-3-(trifluoromethyl)phenyl)-5,5-dimethyl-4-oxo-2-thioxoimidazolidin-1-yl)pyridin-2-yl)oxy)methyl)cyclopropyl)carbamate |
| 13a | 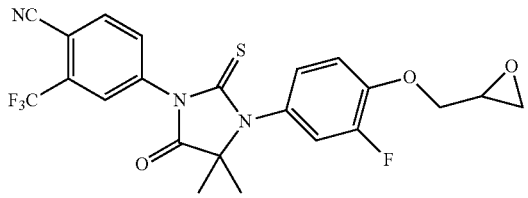 [SMILES: CC1(C)C(=O)N(c2ccc(C#N)c(C(F)(F)F)c2)C(=S)N1c1ccc(OCC2CO2)c(F)c1]
4-(3-(3-fluoro-4-(oxiran-2-ylmethoxy)phenyl)-4,4-dimethyl-5-oxo-2-thioxoimidazolidin-1-yl)-2-(trifluoromethyl)benzonitrile |
| 19b | 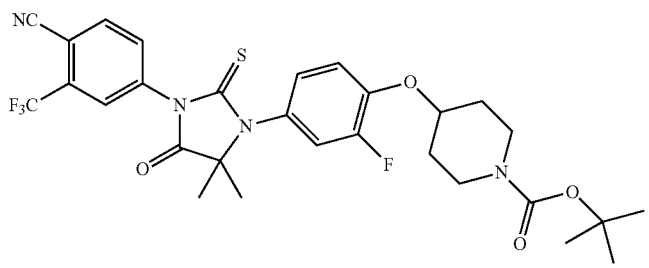 [SMILES: CC(C)(C)OC(=O)N1CCC(Oc2ccc(N3C(=S)N(c4ccc(C#N)c(C(F)(F)F)c4)C(=O)C3(C)C)cc2F)CC1]
tert-butyl 4-(4-(3-(4-cyano-3-(trifluoromethyl)phenyl)-5,5-dimethyl-4-oxo-2-thioxoimidazolidin-1-yl)-2-fluorophenoxy)piperidine-1-carboxylate |

-continued

| Example No. | Structure and Name |
|---|---|
| 31a | 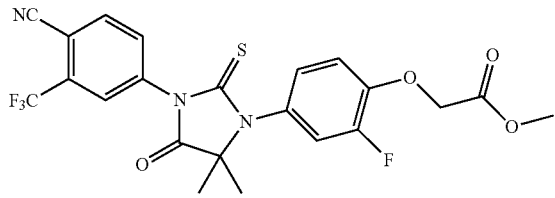 [SMILES: COC(=O)COc1ccc(N2C(=S)N(c3ccc(C#N)c(C(F)(F)F)c3)C(=O)C2(C)C)cc1F]<br>methyl 2-(4-(3-(4-cyano-3-(trifluoromethyl)phenyl)-5,5-dimethyl-4-oxo-2-thioxoimidazolidin-1-yl)-2-fluorophenoxy)acetate |
| 33b | 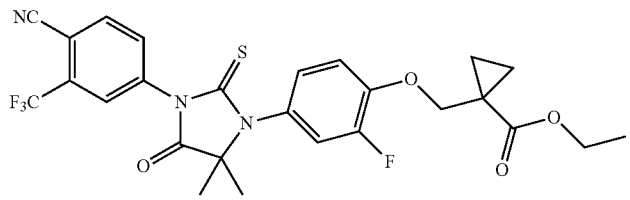 [SMILES: CCOC(=O)C1(COc2ccc(N3C(=S)N(c4ccc(C#N)c(C(F)(F)F)c4)C(=O)C3(C)C)cc2F)CC1]<br>ethyl 1-((4-(3-(4-cyano-3-(trifluoromethyl)phenyl)-5,5-dimethyl-4-oxo-2-thioxoimidazolidin-1-yl)-2-fluorophenoxy)methyl)cyclopropanecarboxylate |
| 46b | 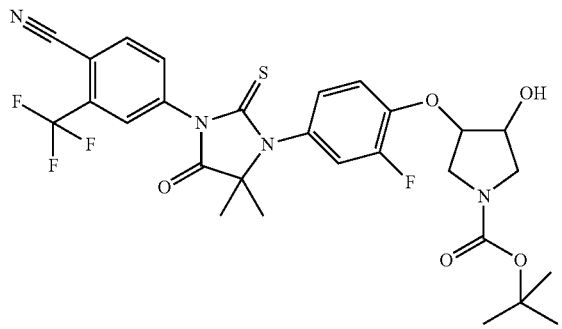 [SMILES: CC(C)(C)OC(=O)N1CC(O)C(Oc2ccc(N3C(=S)N(c4ccc(C#N)c(C(F)(F)F)c4)C(=O)C3(C)C)cc2F)C1]<br>tert-butyl 3-(4-(3-(4-cyano-3-(trifluoromethyl)phenyl)-5,5-dimethyl-4-oxo-2-thioxoimidazolidin-1-yl)-2-fluorophenoxy)-4-hydroxypyrrolidine-1-carboxylate |
| 6b | 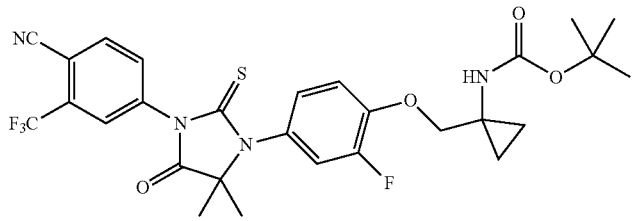<br>6b<br>tert-butyl (1-((4-(3-(4-cyano-3-(trifluoromethyl)phenyl)-5,5-dimethyl-4-oxo-2-thioxoimidazolidin-1-yl)-2-fluorophenoxy)methyl)cyclopropyl)carbamate |
| 27a | 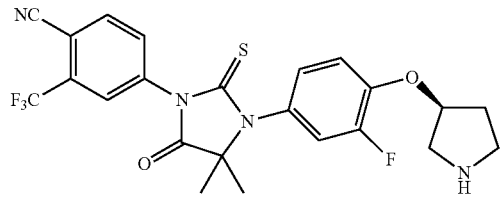<br>27a<br>(S)-4-(3-(3-fluoro-4-((pyrrolidin-3-yl)oxy)phenyl)-4,4-dimethyl-5-oxo-2-thioxoimidazolidin-1-yl)-2-(trifluoromethyl)benzonitrile |

| Example No. | Structure and Name |
|---|---|
| 35d | 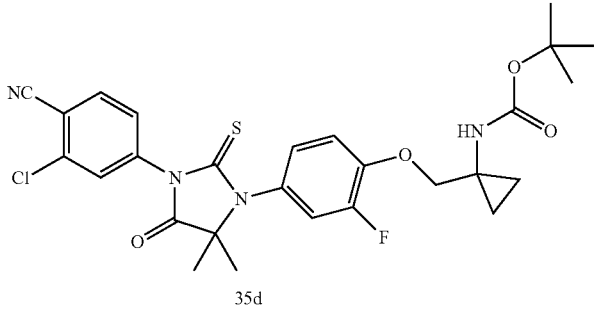 [SMILES: CC(C)(C)OC(=O)NC1(COc2ccc(N3C(=S)N(c4ccc(C#N)c(Cl)c4)C(=O)C3(C)C)cc2F)CC1]<br>35d<br><br>tert-butyl (1-((4-(3-(3-chloro-4-cyanophenyl)-5,5-dimethyl-4-oxo-2-thioxoimidazolidin-1-yl)-2-fluorophenoxy)methyl)cyclopropyl)carbamate |
| 37a | 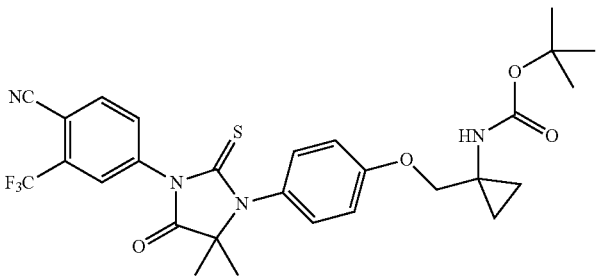<br>37a<br><br>tert-butyl (1-((4-(3-(4-cyano-3-(trifluoromethyl)phenyl)-5,5-dimethyl-4-oxo-2-thioxoimidazolidin-1-yl)phenoxy)methyl)cyclopropyl)carbamate |
| 38d | 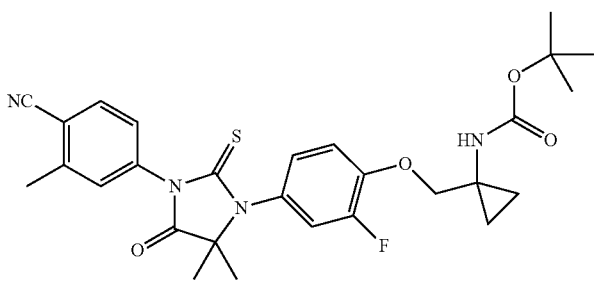<br>38d<br><br>tert-butyl (1-((4-(3-(4-cyano-3-methylphenyl)-5,5-dimethyl-4-oxo-2-thioxoimidazolidin-1-yl)-2-fluorophenoxy)methyl)cyclopropyl)carbamate |
| 42b | 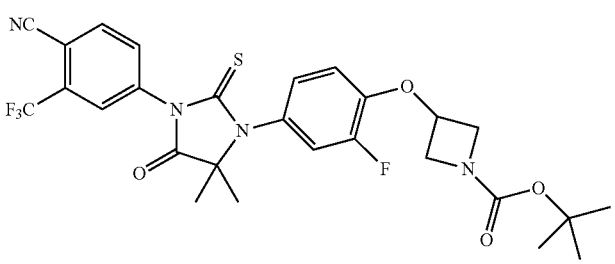<br>42b<br><br>tert-butyl 3-(4-(3-(4-cyano-3-(trifluoromethyl)phenyl)-5,5-dimethyl-4-oxo-2-thioxoimidazolidin-1-yl)-2-fluorophenoxy)azetidine-1-carboxylate |

| Example No. | Structure and Name |
|---|---|
| 43c | 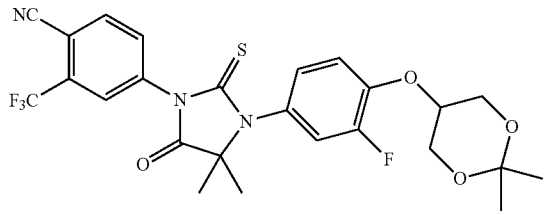

43c 4-(3-(4-((2,2-dimethyl-1,3-dioxan-5-yl)oxy)-3-fluorophenyl)-4,4-dimethyl-5-oxo-2-thioxoimidazolidin-1-yl)-2-(trifluoromethyl)benzonitrile |
| 44a | 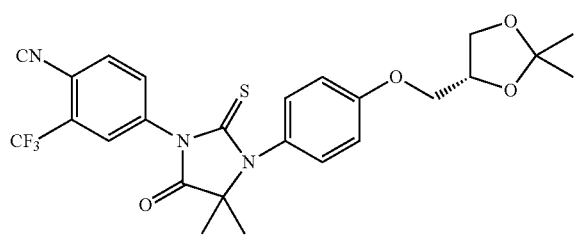

44a (R)-4-(3-(4-((2,2-dimethyl-1,3-dioxolan-4-yl)methoxy)phenyl)-4,4-dimethyl-5-oxo-2-thioxoimidazolidin-1-yl)-2-(trifluoromethyl)benzonitrile |
| 45a | 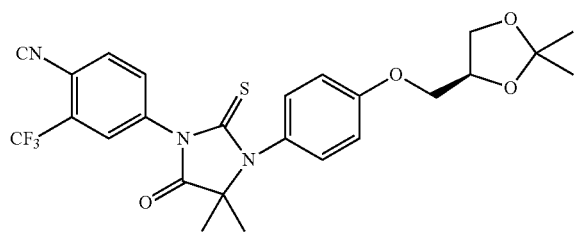

45a (S)-4-(3-(4-((2,2-dimethyl-1,3-dioxolan-4-yl)methoxy)phenyl)-4,4-dimethyl-5-oxo-2-thioxoimidazolidin-1-yl)-2-(trifluoromethyl)benzonitrile |
| 48a | 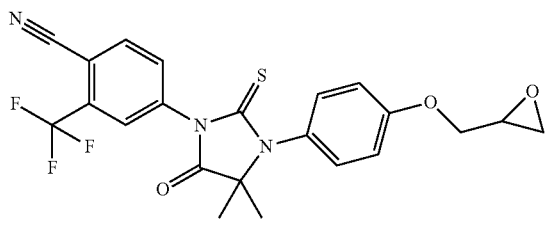

48a 4-(4,4-dimethyl-3-(4-(oxiran-2-ylmethoxy)phenyl)-5-oxo-2-thioxoimidazolidin-1-yl)-2-(trifluoromethyl)benzonitrile | or a tautomer, mesomer, racemate, enantiomer, diastereomer, or mixture thereof, or a pharmaceutically acceptable salt thereof.

In another aspect, the invention provides an intermediate for synthesizing the compounds described above. For example, compounds 11a, 13a, 19b, 31a, 33b, 46b, 6b, 27a, 35d, 37a, 38d, 42b, 43c, 44a, 45a, 48a can be used as an intermediate for synthesizing the corresponding compounds. For example, compound 11a can be used as an intermediate for synthesizing compound 11, and compound 13a can be used as an intermediate for synthesizing compound 13, and so on.

In another aspect, the invention provides a process of preparing a compound of formula (I), or a tautomer, mesomer, racemate, enantiomer, diastereomer, or mixture thereof, or a pharmaceutically acceptable salt thereof, comprising a step of:

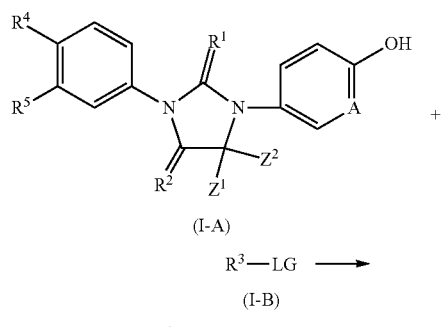

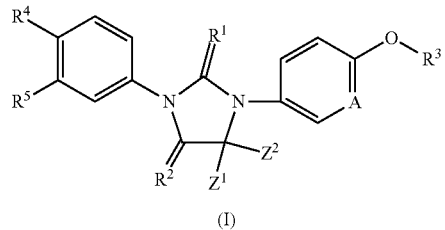

reacting a compound of formula (I-A) with a compound of formula (I-B) under an alkaline condition to obtain a compound of formula (I);

wherein LG is a leaving group, preferably halogen or p-toluenesulfonyloxy; and A, $Z^1$, $Z^2$, and $R^1$ to $R^5$ are as defined in formula (I).

In another aspect, the invention provides a process of preparing a compound of formula (I), or a tautomer, mesomer, racemate, enantiomer, diastereomer, or mixture thereof, or a pharmaceutically acceptable salt thereof, comprising a step of:

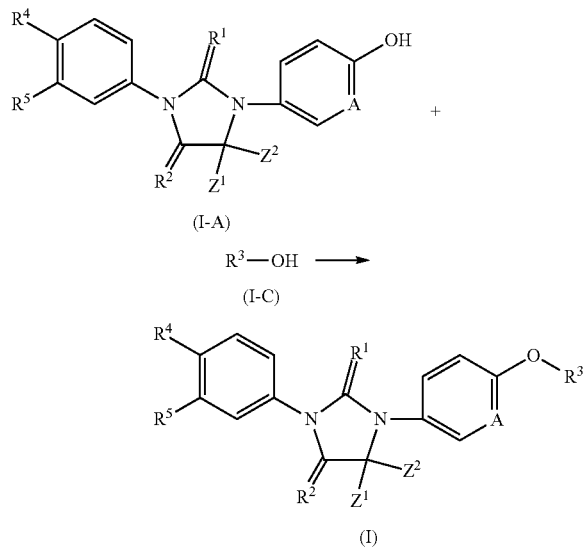

condensing a compound of formula (I-A) with a compound of formula (I-C) in the presence of triphenylphosphine or tri-n-butylphosphine, azodicarboxylate (preferably 1,1'-(azodicarbonyl)dipiperidine or diisopropyl azodicarboxylate) to obtain a compound of formula (I); wherein A, $Z^1$, $Z^2$, and $R^1$ to $R^5$ are as defined in formula (I).

In another aspect, the invention provides a compound of formula (IIA):

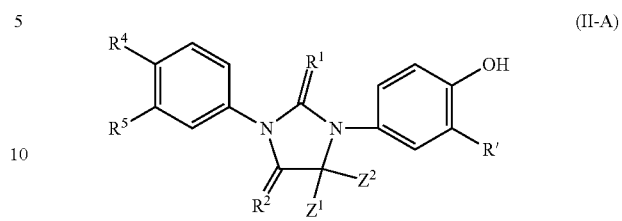

used as an intermediate for preparing a compound of formula (II), wherein:
R' is hydrogen, halogen, alkyl, cycloalkyl, or heterocyclyl, wherein the alkyl, cycloalkyl and heterocyclyl are each optionally substituted with one or more groups selected from the group consisting of halogen, cyano, hydroxy, alkyl, alkoxy, carboxyl and carboxylic ester; R' is preferably hydrogen or halogen;
$Z^1$ and $Z^2$ are each independently alkyl, or $Z^1$ and $Z^2$ are taken together with the attached carbon atoms to form a cycloalkyl or heterocyclyl;
$R^1$ and $R^2$ are each independently selected from the group consisting of S and O; and
$R^4$ and $R^5$ are each independently selected from the group consisting of cyano, nitro, alkyl, haloalkyl, hydroxy, hydrogen, alkoxy, and haloalkoxy.

In another aspect, the invention provides a process of preparing a compound of formula (II), or a tautomer, mesomer, racemate, enantiomer, diastereomer, or mixture thereof, or a pharmaceutically acceptable salt thereof, comprising a step of:

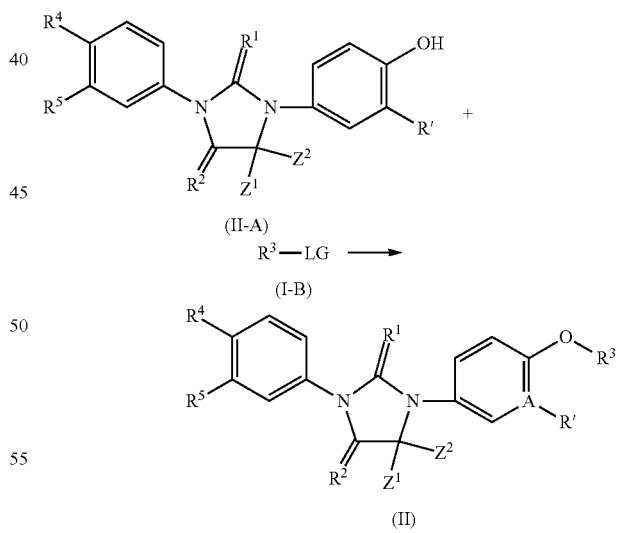

reacting a compound of formula (II-A) with a compound of formula (I-B) under an alkaline condition to obtain a compound of formula (II);
wherein LG is a leaving group, preferably halogen or p-toluenesulfonyloxy; and A, $Z^1$, $Z^2$, R', and $R^1$ to $R^5$ are as defined in formula (I).

In another aspect, the invention provides a process of preparing a compound of formula (II), or a tautomer, mesomer, racemate, enantiomer, diastereomer, or mixture thereof, or a pharmaceutically acceptable salt thereof, comprising a step of:

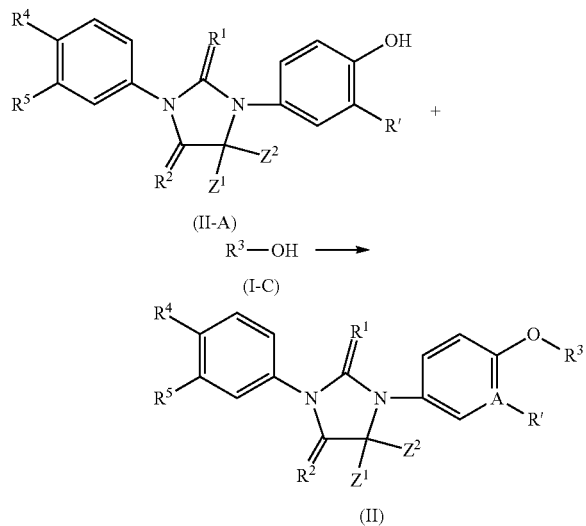

condensing a compound of formula (II-A) with a compound of formula (I-C) in the presence of triphenylphosphine or tri-n-butylphosphine, azodicarboxylate (preferably 1,1'-(azodicarbonyl)dipiperidine or diisopropyl azodicarboxylate) to obtain a compound of formula (II); wherein A, $Z^1$, $Z^2$, R', and $R^1$ to $R^5$ are as defined in formula (I).

The present invention also provides a pharmaceutical composition comprising a therapeutically effective amount of a compound of formula (I), or a tautomer, mesomer, racemate, enantiomer, diastereomer, or mixture thereof, or a pharmaceutically acceptable salt thereof, together with a pharmaceutically acceptable carrier, diluent or excipient.

The present invention also relates to use of a compound of formula (I), or a tautomer, mesomer, racemate, enantiomer, diastereomer, or mixture thereof, or a pharmaceutically acceptable salt thereof, or a pharmaceutical composition comprising the same, in the preparation of a medicament for modulating an androgen receptor.

The present invention also relates to use of a compound of formula (I), or a tautomer, mesomer, racemate, enantiomer, diastereomer, or mixture thereof, or a pharmaceutically acceptable salt thereof, or a pharmaceutical composition comprising the same, in the preparation of a medicament for inhibiting an androgen receptor.

The present invention also relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for modulating an androgen receptor, preferably for inhibiting an androgen receptor.

The present invention also relates to a method for modulating androgen receptor activity, preferably inhibiting androgen receptor activity, comprising a step of administering to a subject in need thereof a therapeutically effective amount of a compound of formula (I), or a tautomer, racemate, enantiomer, diastereoisomer, or mixture thereof, or a pharmaceutically acceptable salt thereof, or a pharmaceutical composition containing the same.

The present invention also relates to use of a compound of formula (I), or a tautomer, mesomer, racemate, enantiomer, diastereomer, or mixture thereof, or a pharmaceutically acceptable salt thereof, or a pharmaceutical composition comprising the same, in the preparation of a medicament for the treatment or prevention of androgen receptor-mediated disorders or diseases, wherein the androgen receptor-mediated disorders or diseases are selected from the group consisting of prostate cancer, prostatic hyperplasia, hirsutism, alopecia, anorexia nervosa, breast cancer, acne, male sexual dysfunction, AIDS and cachexia, preferably breast cancer or prostate cancer, more preferably prostate cancer, and most preferably hormone-sensitive prostate cancer or hormone-refractory prostate cancer.

The present invention also relates to a method for the treatment or prevention of androgen receptor-mediated disorders or diseases, comprising a step of administering to a subject in need thereof a therapeutically effective amount of a compound of formula (I), or a tautomer, racemate, enantiomer, diastereoisomer, or mixture thereof, or a pharmaceutically acceptable salt thereof, or a pharmaceutical composition comprising the same, wherein the androgen receptor-mediated disorders or diseases are selected from the group consisting of prostate cancer, prostatic hyperplasia, hirsutism, alopecia, anorexia nervosa, breast cancer, acne, male sexual dysfunction, AIDS and cachexia, preferably breast cancer or prostate cancer, more preferably prostate cancer, and most preferably hormone-sensitive prostate cancer or hormone-refractory prostate cancer.

The present invention also relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for the treatment or prevention of androgen receptor-mediated disorders or diseases, wherein the androgen receptor-mediated disorders or diseases are selected from the group consisting of prostate cancer, prostatic hyperplasia, hirsutism, alopecia, anorexia nervosa, breast cancer, acne, male sexual dysfunction, AIDS and cachexia, preferably breast cancer or prostate cancer, more preferably prostate cancer, and most preferably hormone-sensitive prostate cancer or hormone-refractory prostate cancer.

The present invention also relates to use of a compound of formula (I), or a tautomer, mesomer, racemate, enantiomer, diastereomer, or mixture thereof, or a pharmaceutically acceptable salt thereof, or the pharmaceutical composition comprising the same, in the preparation of a medicament for male contraception.

The present invention also relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for male contraception.

The present invention also relates to a method of male contraception, comprising a step of administering to a subject in need thereof a therapeutically effective amount of a compound of formula (I), or a tautomer, racemate, enantiomer, diastereoisomer, or mixture thereof, or a pharmaceutically acceptable salt thereof, or a pharmaceutical composition comprising the same.

DETAILED DESCRIPTION OF THE INVENTION

Unless otherwise stated, the terms used in the specification and claims have the meanings described below.

"Alkyl" refers to a saturated aliphatic hydrocarbon group including $C_1$-$C_{20}$ straight chain and branched chain groups. Preferably, an alkyl group is an alkyl having 1 to 10 carbon atoms, and more preferably an alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methyl-propyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and isomers of branched chains thereof. More preferably an alkyl group is a lower alkyl having 1 to 6 carbon atoms, representative examples of which include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, and preferably the substituent group(s) is one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, oxo group, —$OR^6$, —$NR^7R^8$, —$C(O)NR^7R^8$, —$S(O)_mR^6$, —$C(O)R^6$, —$OC(O)R^6$, —$NR^7C(O)R^8$, —$NR^7C(O)OR^8$, and —$C(O)OR^6$.

"Cycloalkyl" refers to a saturated or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms. Representative examples of monocyclic cycloalkyls include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes a cycloalkyl having a spiro ring, fused ring, or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system. Preferably, a spiro cycloalkyl is 6 to 14 membered, and more preferably 7 to 10 membered. According to the number of common spiro atoms, a spiro cycloalkyl is divided into mono-spiro cycloalkyl, di-spiro cycloalkyl, or poly-spiro cycloalkyl, and preferably refers to a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Representative examples of spiro cycloalkyls include, but are not limited to, the following groups:

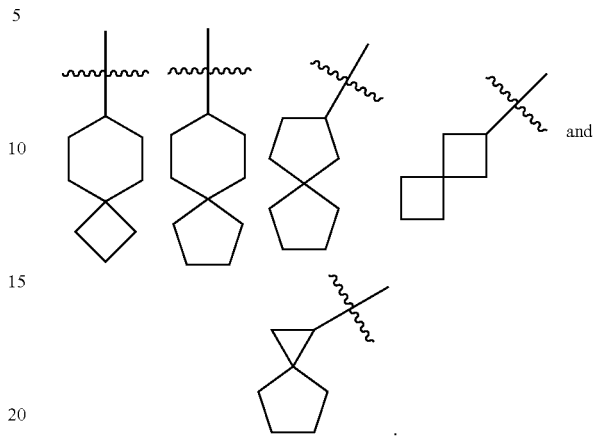

"Fused cycloalkyl" refers to a 5 to 20 membered polycyclic hydrocarbon group, wherein each ring in the system shares an adjacent pair of carbon atoms with another ring, wherein one or more rings can contain one or more double bonds, but none of the rings has a completely conjugated pi-electron system. Preferably, a fused cycloalkyl group is 6 to 14 membered, and more preferably 7 to 10 membered. According to the number of membered rings, a fused cycloalkyl is divided into bicyclic, tricyclic, tetracyclic, or polycyclic fused cycloalkyl, and preferably refers to a bicyclic or tricyclic fused cycloalkyl, and more preferably 5-membered/5-membered, or 5-membered/6-membered bicyclic fused cycloalkyl. Representative examples of fused cycloalkyls include, but are not limited to, the following groups:

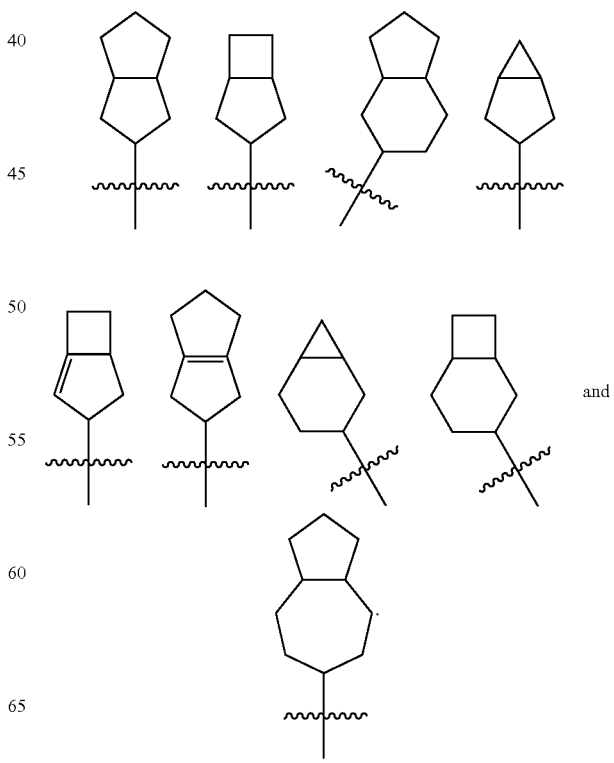

"Bridged cycloalkyl" refers to a 5 to 20 membered polycyclic hydrocarbon group, wherein every two rings in the system share two disconnected carbon atoms. The rings can have one or more double bonds, but none of the rings has a completely conjugated pi-electron system. Preferably, a bridged cycloalkyl is 6 to 14 membered, and more preferably 7 to 10 membered. According to the number of membered rings, a bridged cycloalkyl is divided into bicyclic, tricyclic, tetracyclic or polycyclic bridged cycloalkyl, and preferably refers to a bicyclic, tricyclic, or tetracyclic bridged cycloalkyl, and more preferably refers to a bicyclic or tricyclic bridged cycloalkyl. Representative examples of bridged cycloalkyls include, but are not limited to, the following groups:

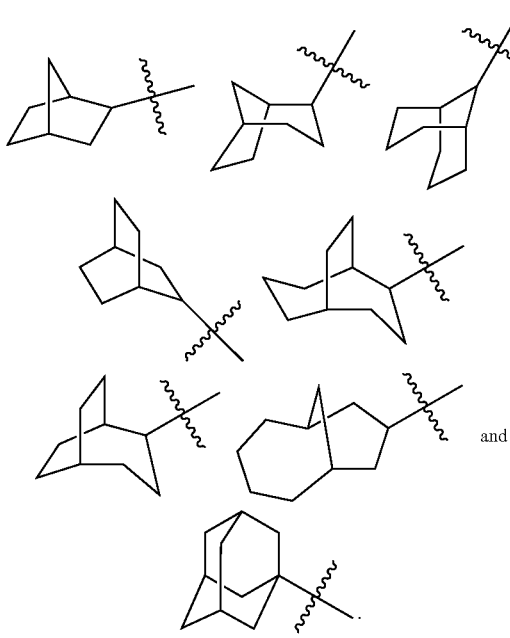

The cycloalkyl can be fused to the ring of an aryl, heteroaryl or heterocyclic alkyl, wherein the ring bound to the parent structure is cycloalkyl. Representative examples include, but are not limited to indanylacetic, tetrahydronaphthalene, benzocycloheptyl, and so on. The cycloalkyl can be optionally substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, oxo group, —OR$^6$, —NR$^7$R$^8$, —C(O)NR$^7$R$^8$, —S(O)$_m$R$^6$, —C(O)R$^6$, —OC(O)R$^6$, —NR$^7$C(O)R$^8$, —NR$^7$C(O)OR$^8$, and —C(O)OR$^6$.

"Heterocyclyl" refers to a 3 to 20 membered saturated or partially unsaturated monocyclic or polycyclic hydrocarbon group having one or more heteroatoms selected from the group consisting of N, O, and S(O)$_m$ (wherein m is an integer selected from 0, 1, and 2) as ring atoms, but excluding —O—O—, —O—S— or —S—S— in the ring, with the remaining ring atoms being C. Preferably, heterocyclyl has 3 to 12 atoms, wherein 1 to 4 atoms are heteroatoms; more preferably 3 to 10 atoms; and most preferably 4 to 6 atoms. Representative examples of monocyclic heterocyclyls include, but are not limited to, pyrrolidyl, piperidyl, piperazinyl, morpholinyl, sulfo-morpholinyl, homopiperazinyl, pyranyl, tetrahydrofuranyl, 1,1-dioxo-tetrahydrothiopyranyl, oxetanyl, azetidinyl, and so on. Polycyclic heterocyclyl includes a heterocyclyl having a spiro ring, fused ring, or bridged ring.

"Spiro heterocyclyl" refers to a 5 to 20 membered polycyclic heterocyclyl with rings connected through one common carbon atom (called a spiro atom), wherein said rings have one or more heteroatoms selected from the group consisting of N, O, and S(O)$_m$ (wherein m is an integer selected from 0, 1, and 2) as ring atoms, with the remaining ring atoms being C, wherein one or more rings can contain one or more double bonds, but none of the rings has a completely conjugated pi-electron system. Preferably a spiro heterocyclyl is 6 to 14 membered, and more preferably 7 to 10 membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Representative examples of spiro heterocyclyls include, but are not limited to the following groups:

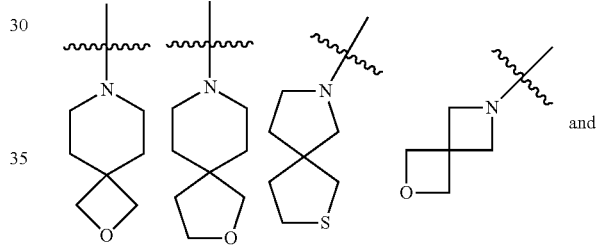

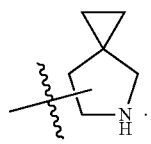

"Fused heterocyclyl" refers to a 5 to 20 membered polycyclic heterocyclyl group, wherein each ring in the system shares an adjacent pair of carbon atoms with another ring, wherein one or more rings can contain one or more double bonds, but none of the rings has a completely conjugated pi-electron system, and wherein said rings have one or more heteroatoms selected from the group consisting of N, O, and S(O)$_m$ (wherein m is an integer selected from 0, 1, and 2) as ring atoms, with the remaining ring atoms being C. Preferably, a fused heterocyclyl is 6 to 14 membered, and more preferably 7 to 10 membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocyclyls include, but are not limited to, the following groups:

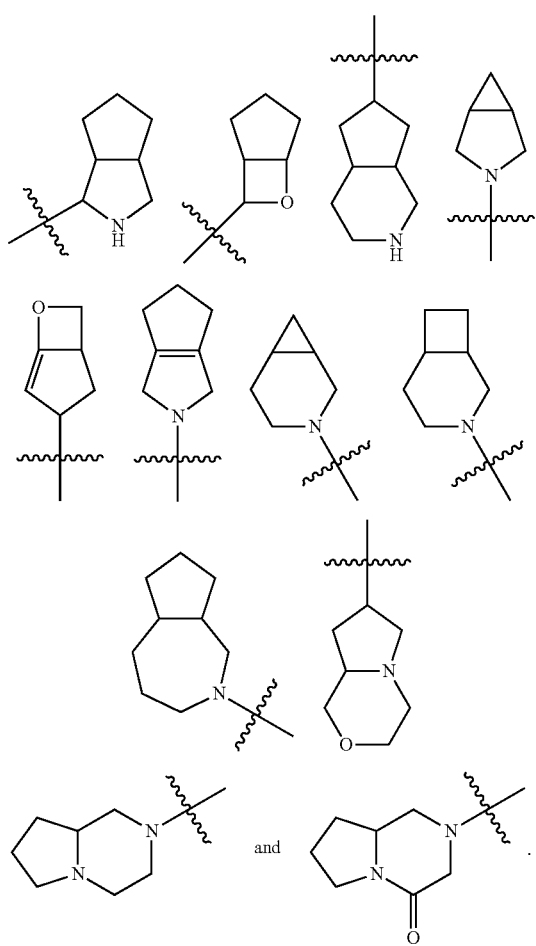

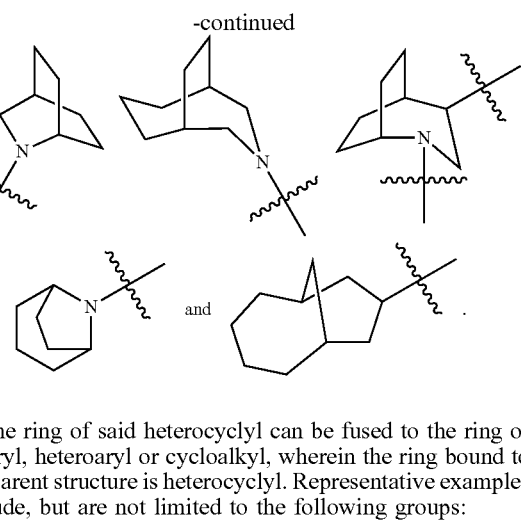

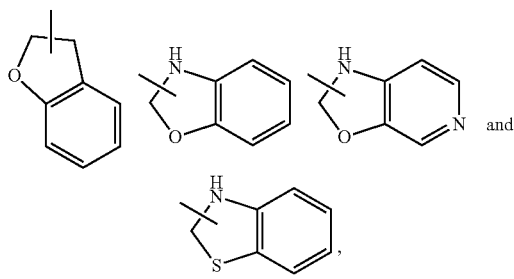

"Bridged heterocyclyl" refers to a 5 to 14 membered polycyclic heterocyclic alkyl group, wherein every two rings in the system share two disconnected atoms, the rings can have one or more double bonds, but none of the rings has a completely conjugated pi-electron system, and the rings have one or more heteroatoms selected from the group consisting of N, O, and $S(O)_m$ (wherein m is an integer selected from 0, 1, and 2) as ring atoms, with the remaining ring atoms being C. Preferably, a bridged heterocyclyl is 6 to 14 membered, and more preferably 7 to 10 membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but are not limited to, the following groups:

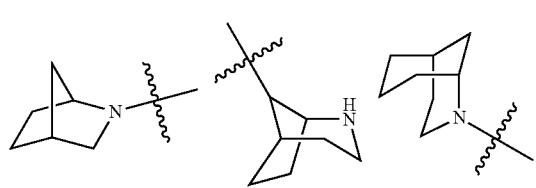

The ring of said heterocyclyl can be fused to the ring of an aryl, heteroaryl or cycloalkyl, wherein the ring bound to the parent structure is heterocyclyl. Representative examples include, but are not limited to the following groups:

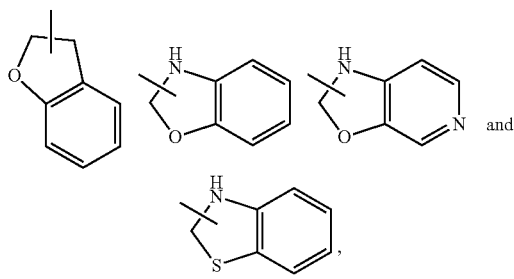

etc.

The heterocyclyl can be optionally substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, oxo group, $-OR^6$, $-NR^7R^8$, $-C(O)NR^7R^8$, $-S(O)_mR^6$, $-C(O)R^6$, $-OC(O)R^6$, $-NR^7C(O)R^8$, $-NR^7C(O)OR^8$, and $-C(O)OR^6$.

"Aryl" refers to a 6 to 14 membered all-carbon monocyclic ring or polycyclic fused ring (a "fused" ring system means that each ring in the system shares an adjacent pair of carbon atoms with another ring in the system), which has a completely conjugated pi-electron system. Preferably, aryl is 6 to 10 membered, more preferably phenyl and naphthyl, and most preferably phenyl. The aryl can be fused to the ring of heteroaryl, heterocyclyl or cycloalkyl, wherein the ring bound to the parent structure is aryl. Representative examples include, but are not limited to, the following groups:

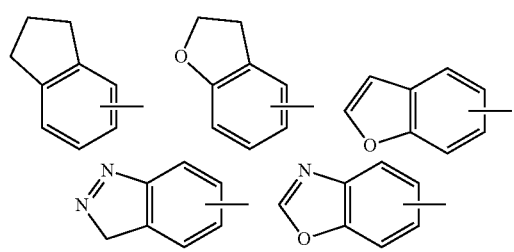

-continued

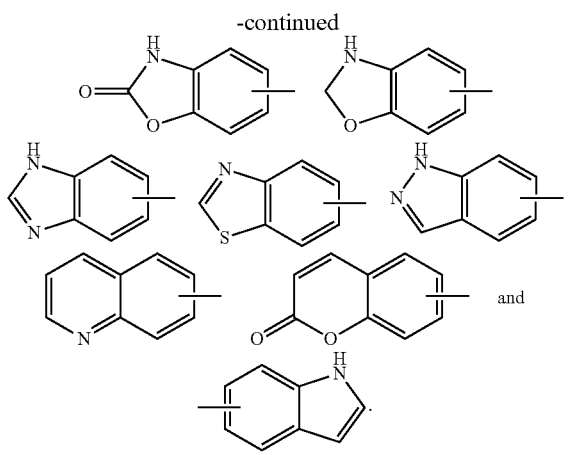

The aryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, —$OR^6$, —$NR^7R^8$, —$C(O)NR^7R^8$, —$S(O)_mR^6$, —$C(O)R^6$, —$OC(O)R^6$, —$NR^7C(O)R^8$, —$NR^7C(O)OR^8$, and —$C(O)OR^6$.

"Heteroaryl" refers to an aryl system having 1 to 4 heteroatoms selected from the group consisting of O, S, and N as ring atoms, and having 5 to 14 members. Preferably, a heteroaryl is 5- to 10-membered, more preferably 5- or 6-membered, and even more preferably furyl, thienyl, pyridyl, pyrrolyl, N-alkyl pyrrolyl, pyrimidinyl, pyrazinyl, imidazolyl, tetrazolyl, and the like. The heteroaryl can be fused with the ring of an aryl, heterocyclyl or cycloalkyl, wherein the ring bound to the parent structure is heteroaryl. Representative examples include, but are not limited to, the following groups:

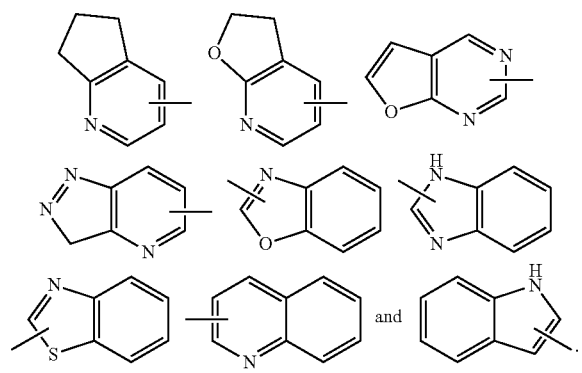

The heteroaryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, —$OR^6$, —$NR^7R^8$, —$C(O)NR^7R^8$, —$S(O)_mR^6$, —$C(O)R^6$, —$OC(O)R^6$, —$NR^7C(O)R^8$, —$NR^7C(O)OR^8$, and —$C(O)OR^6$.

"Alkenyl" refers to an alkyl as defined above that has at least two carbon atoms and at least one carbon-carbon double bond, preferably $C_{2-6}$ alkenyl, and more preferably $C_{2-4}$ alkenyl, for example, vinyl, 1-propenyl, 2-propenyl, 1-, 2-, or 3-butenyl, etc. The alkenyl group can be substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, oxo group, —$OR^6$, —$NR^7R^8$, —$C(O)NR^7R^8$, —$S(O)_mR^6$, —$C(O)R^6$, —$OC(O)R^6$, —$NR^7C(O)R^8$, —$NR^7C(O)OR^8$, and —$C(O)OR^6$.

"Alkynyl" refers to an alkyl as defined above that has at least two carbon atoms and at least one carbon-carbon triple bond, preferably $C_{2-6}$ alkynyl, and more preferably $C_{2-4}$ alkynyl, for example, ethynyl, 1-propynyl, 2-propynyl, 1-, 2-, or 3-butyryl, etc. The alkynyl group can be substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, oxo group, —$OR^6$, —$NR^7R^8$, —$C(O)NR^7R^8$, —$S(O)_mR^6$, —$C(O)R^6$, —$OC(O)R^6$, —$NR^7C(O)R^8$, —$NR^7C(O)OR^8$, and —$C(O)OR^6$.

"Alkoxy" refers to both an —O-(alkyl) and an —O-(unsubstituted cycloalkyl) group, wherein the alkyl and cycloalkyl are as defined above. Representative examples include, but are not limited to, methoxy, ethoxy, propoxy, butoxy, cyclopropyloxy, cyclobutyloxy, cyclopentyloxy, cyclohexyloxy, and the like. The alkoxy can be substituted or unsubstituted. When substituted, the substituent is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, —$OR^6$, —$NR^7R^8$, —$C(O)NR^7R^8$, —$S(O)_mR^6$, —$C(O)R^6$, —$OC(O)R^6$, —$NR^7C(O)R^8$, —$NR^7C(O)OR^8$, and —$C(O)OR^6$.

"Hydroxy alkyl" refers to -(alkyl)-OH, wherein alkyl is as defined above.

"Haloalkyl" refers to a alkyl substituted with one or more halogen atoms, wherein alkyl is as defined above.

"Hydroxy" refers to an —OH group.

"Halogen" refers to fluoro, chloro, bromo, or iodo.

"Amino" refers to an —$NH_2$ group.

"Cyano" refers to a —CN group.

"Nitro" refers to a —$NO_2$ group.

"Oxo group" refers to an =O group.

"Carboxyl" refers to a —C(O)OH group.

"Alkoxycarbonyl" refers to a —C(O)O(alkyl) or (cycloalkyl) group, wherein the alkyl and cycloalkyl are as defined above.

"Optional" or "optionally" means that the event or circumstance described subsequently can, but need not, occur, and the description includes the instances in which the event or circumstance does or does not occur. For example, "the heterocyclic group optionally substituted with an alkyl" means that an alkyl group can be, but need not be, present, and the description includes the case of the heterocyclic group being substituted with an alkyl and the heterocyclic group being not substituted with an alkyl.

"Substituted" refers to one or more hydrogen atoms in the group, preferably up to 5, more preferably 1 to 3 hydrogen atoms, independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxy group having free hydrogen and carbon atoms having unsaturated bonds (such as olefinic) may be unstable.

A "pharmaceutical composition" refers to a mixture of one or more of the compounds described in the present invention, or pharmaceutically acceptable salts or prodrugs thereof and other chemical components such as pharmaceutically acceptable carriers and excipients. The purpose of a pharmaceutical composition is to facilitate administration of a compound to an organism, which is conducive to the absorption of the active ingredient, thus displaying biological activity.

m and $R^6$ to $R^8$ are as defined in the compound of formula (I).

Synthesis Method of the Compound of the Present Invention

In order to complete the purpose of the invention, the present invention applies, but is not limited to, the following technical solution:

A process of preparing a compound of formula (I) of the invention, or a tautomer, racemate, enantiomer, diastereomer, or mixture thereof, or a pharmaceutically acceptable salt thereof, comprising the following steps of:

Scheme 1:

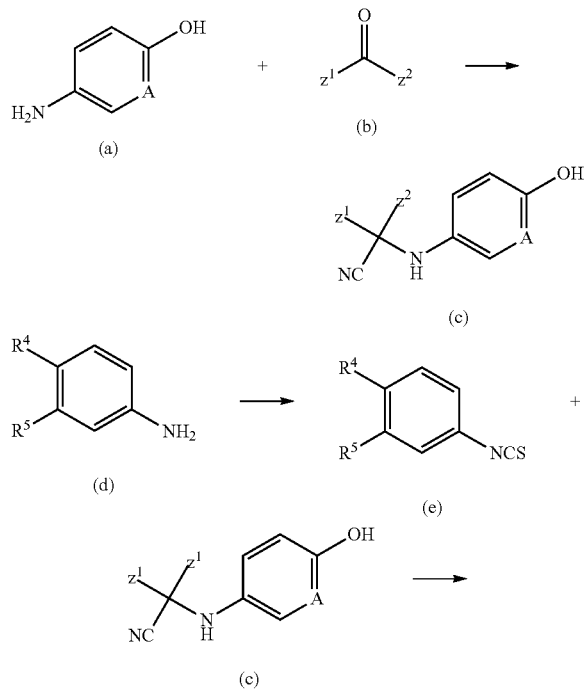

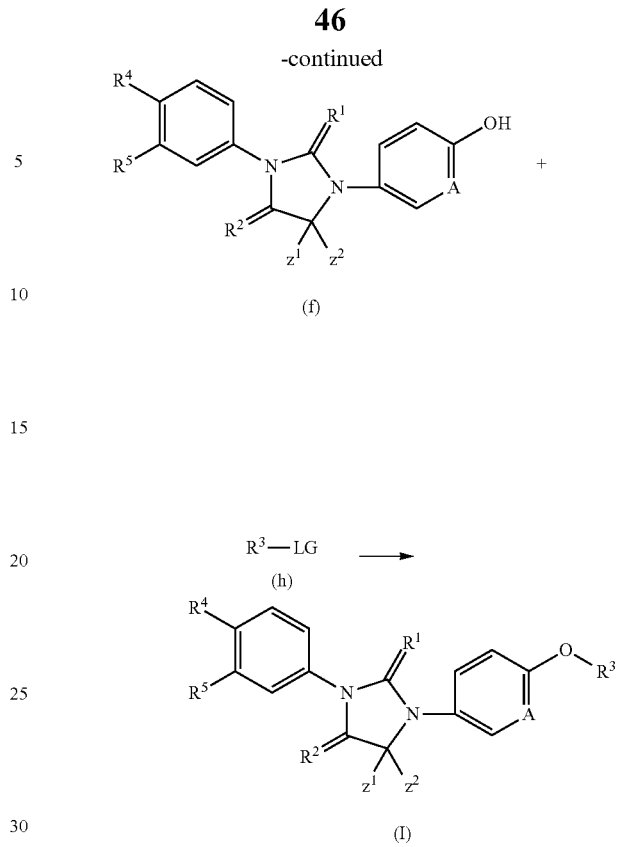

reacting an amino compound (a) with a ketone compound (b) and trimethylsilyl cyanide in a solvent in the presence of trimethylsilyl trifluoromethanesulfonate to obtain a cyano compound (c); reacting a phenylamine compound (d) with thiophosgene in a solvent to obtain an isothiocyanatobenzene compound (e); cyclizing the isothiocyanatobenzene compound (e) with a cyano compound (c) in a solvent, and hydrolyzing the resulting product under an acidic condition to obtain a thioxoimidazolidine compound (f); then reacting the thioxoimidazolidine compound (f) with a LG-substituted $R^3$ compound (g) in a solvent under an alkaline condition to obtain a compound of formula (I); wherein LG is a leaving group, preferably halogen or p-toluenesulfonyloxy; and A, $Z^1$, $Z^2$, and $R^1$ to $R^5$ are as defined in formula (I).

The acidic condition includes, but is not limited to, trifluoroacetic acid, formic acid, acetic acid, hydrochloric acid, sulfuric acid, and methanesulfonic acid, preferably hydrochloric acid.

The alkaline condition includes an organic alkali and an inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide; and the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, or potassium hydroxide.

The solvent includes, but is not limited to, acetic acid, ethanol, tetrahydrofuran, dimethyl sulfoxide, 1,4-dioxane, n-hexane, acetone, methanol, water, acetonitrile, dichloromethane, methylbenzene, N,N-dimethylformamide, and N,N-dimethylacetamide.

Scheme 2:

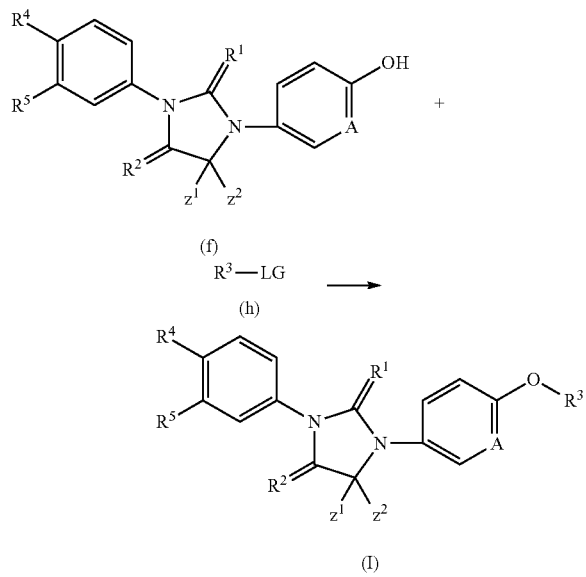

condensing a thioxoimidazolidine compound (f) with a hydroxy-substituted $R^3$ compound (h) in a solvent in the presence of triphenylphosphine or tri-n-butylphosphine, azodicarboxylic acid derivatives (preferably 1,1'-(azodicarbonyl)dipiperidine or diisopropyl azodicarboxylate) to obtain a compound of formula (I); wherein A, $Z^1$, $Z^2$, and $R^1$-$R^5$ are as defined in formula (I).

The alkaline condition includes an organic alkali and an inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide; wherein the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, or potassium hydroxide.

The solvent includes, but is not limited to, acetic acid, ethanol, tetrahydrofuran, dimethyl sulfoxide, 1,4-dioxane, n-hexane, acetone, methanol, water, acetonitrile, dichloromethane, methylbenzene, N,N-dimethylformamide, and N,N-dimethylacetamide.

Scheme 3:

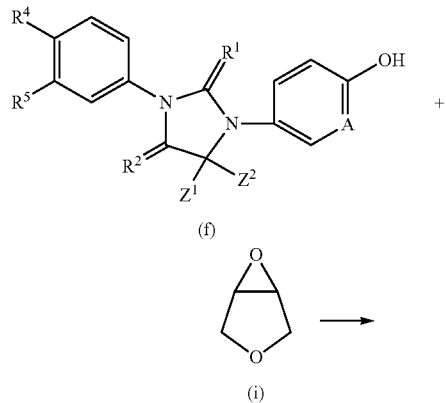

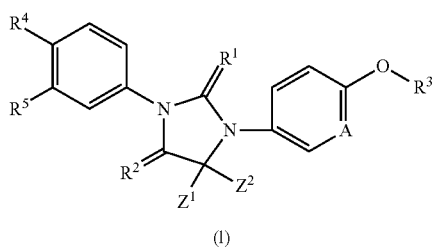

reacting a thioxoimidazolidine compound (f) with 3,4-epoxy-tetrahydrofuran (i) in a solvent under an alkaline condition to obtain a compound of formula (I); wherein A, $Z^1$, $Z^2$, $R^1$, $R^2$, $R^4$, and $R^5$ are as defined in formula (I), and $R^3$ is 4-hydroxy-tetrahydrofuran.

The alkaline condition includes an organic alkali and an inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide; and the inorganic alkali includes, but is not limited to, sodium hydride, sodium hydroxide, potassium hydroxide, sodium carbonate, sodium bicarbonate, potassium carbonate, potassium bicarbonate, or cesium carbonate, preferably sodium carbonate, potassium carbonate, and potassium hydroxide.

The solvent includes, but is not limited to, acetic acid, ethanol, tetrahydrofuran, dimethyl sulfoxide, 1,4-dioxane, n-hexane, acetone, methanol, water, acetonitrile, dichloromethane, methylbenzene, N,N-dimethylformamide, and N, N-dimethylacetamide.

A process of preparing a compound of formula (II) of the invention, or a tautomer, racemate, enantiomer, diastereomer thereof, or mixture thereof, or a pharmaceutically acceptable salt thereof, comprising the following steps of:

Scheme 4:

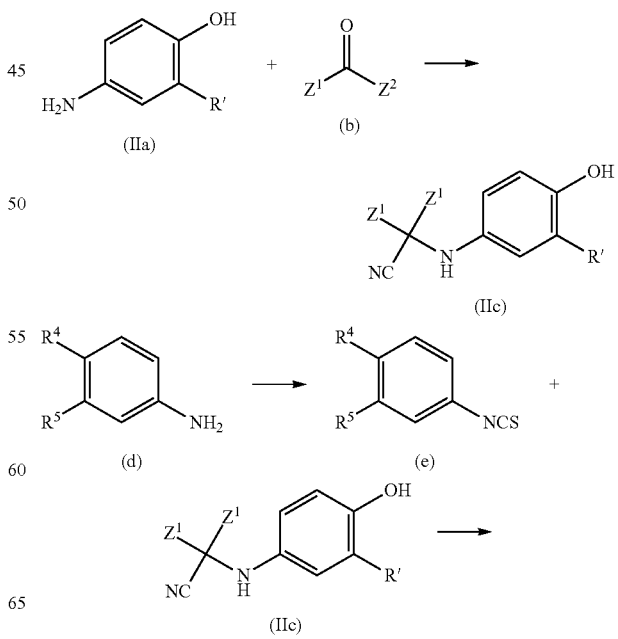

-continued

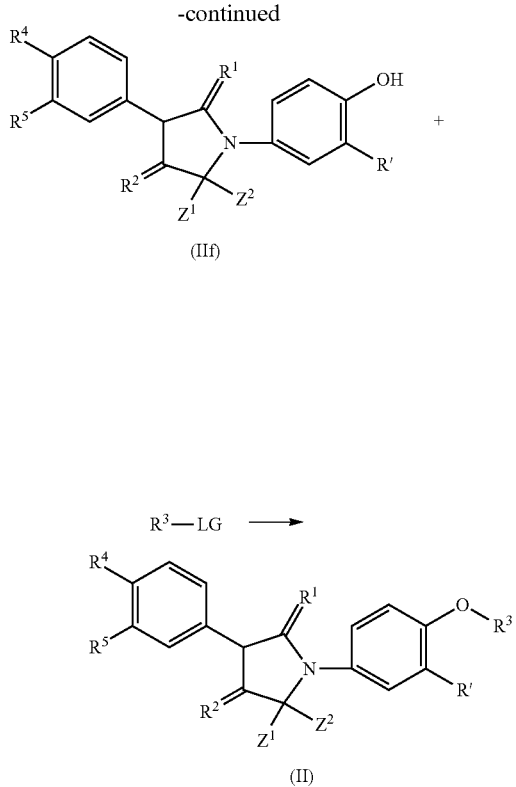

reacting an amino compound (IIa) with a ketone compound (b) and trimethylsilyl cyanide in a solvent in the presence of trimethylsilyl trifluoromethanesulfonate to obtain a cyano compound (IIc); reacting a phenylamine compound (d) with thiophosgene in a solvent to obtain an isothiocyanatobenzene compound (e); cyclizing the isothiocyanatobenzene compound (e) with a cyano compound (IIc) in a solvent, and hydrolyzing the resulting product under an acidic condition to obtain a thioxoimidazolidine compound (IIf); then reacting the thioxoimidazolidine compound (IIf) with a LG-substituted $R^3$ compound (g) in a solvent under an alkaline condition to obtain a compound of formula (II); wherein LG is a leaving group, preferably halogen or p-toluenesulfonyloxy; and $Z^1$, $Z^2$, R', and $R^1$ to $R^5$ are as defined in formula (II).

The acidic condition includes, but is not limited to, trifluoroacetic acid, formic acid, acetic acid, hydrochloric acid, sulfuric acid, and methanesulfonic acid, preferably hydrochloric acid.

The alkaline condition includes an organic alkali and an inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide; and the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, or potassium hydroxide.

The solvent includes, but is not limited to, acetic acid, ethanol, tetrahydrofuran, dimethyl sulfoxide, 1,4-dioxane, n-hexane, acetone, methanol, water, acetonitrile, dichloromethane, methylbenzene, N,N-dimethylformamide, and N,N-dimethylacetamide.

Scheme 5:

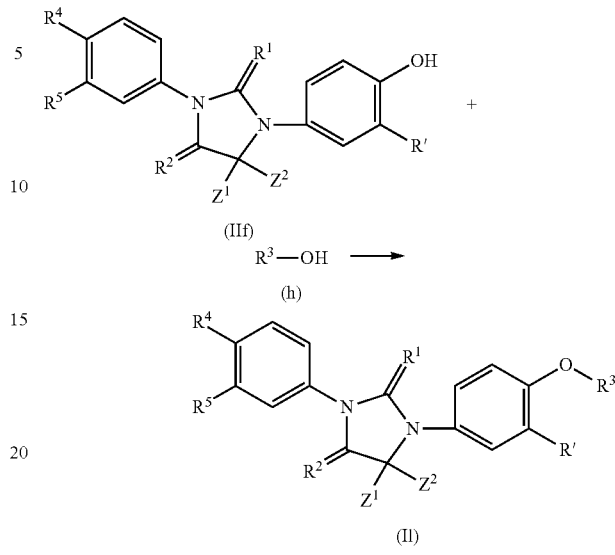

condensing a thioxoimidazolidine compound (IIf) with a hydroxy-substituted $R^3$ compound (h) in a solvent in the presence of triphenylphosphine or tri-n-butylphosphine, azodicarboxylic acid derivatives (preferably 1,1'-(azodicarbonyl)dipiperidine or diisopropyl azodicarboxylate) to obtain a compound of formula (II); wherein $Z^1$, $Z^2$, R', and $R^1$-$R^5$ are as defined in formula (II).

The alkaline condition includes an organic alkali and an inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide; and the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, or potassium hydroxide.

The solvent includes, but is not limited to, acetic acid, ethanol, tetrahydrofuran, dimethyl sulfoxide, 1,4-dioxane, n-hexane, acetone, methanol, water, acetonitrile, dichloromethane, methylbenzene, N,N-dimethylformamide, and N,N-dimethylacetamide.

Scheme 6:

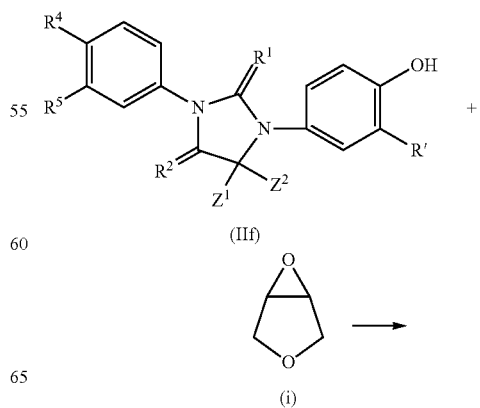

-continued

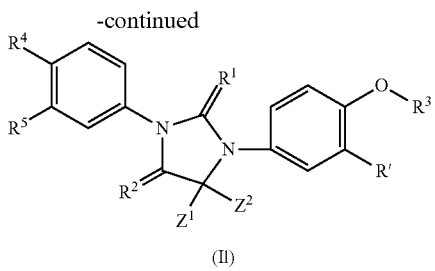

(II)

reacting a thioxoimidazolidine compound (IIf) with 3,4-epoxy-tetrahydrofuran (i) in a solvent under an alkaline condition to obtain a compound of formula (II); wherein $Z^1$, $Z^2$, R', $R^1$, $R^2$, $R^4$, and $R^5$ are as defined in formula (II), and $R^3$ is 4-hydroxy-tetrahydrofuran.

The alkaline condition includes an organic alkali and an inorganic alkali, wherein the organic alkali includes, but is not limited to, triethylamine, N,N-diisopropylethylamine, N,N-dimethylformamide, n-butyllithium, potassium tert-butoxide, and tetrabutyl ammonium bromide; and the inorganic alkali includes, but is not limited to, sodium hydride, sodium hydroxide, potassium hydroxide, sodium carbonate, sodium bicarbonate, potassium carbonate, potassium bicarbonate, and cesium carbonate, preferably sodium carbonate, potassium carbonate, or potassium hydroxide.

The solvent includes, but is not limited to, acetic acid, ethanol, tetrahydrofuran, dimethyl sulfoxide, 1,4-dioxane, n-hexane, acetone, methanol, water, acetonitrile, dichloromethane, methylbenzene, N,N-dimethylformamide, and N,N-dimethylacetamide.

Preferred Embodiments

The following examples serve to illustrate the invention, but the examples should not be considered as limiting the scope of the invention.

If specific conditions for the experimental method are not specified in the examples of the present invention, they are generally in accordance with conventional conditions or recommended conditions of the raw materials and the product manufacturer. The reagents without a specific source indicated are commercially available, conventional reagents.

EXAMPLES

Compound structures were identified by nuclear magnetic resonance (NMR) and/or mass spectrometry (MS). NMR was determined by a Bruker AVANCE-400 machine. NMR chemical shifts (δ) are given in $10^{-6}$ (ppm). The solvents were deuterated-dimethyl sulfoxide (DMSO-$d_6$), deuterated-chloroform (CDCl$_3$) and deuterated-methanol (CD$_3$OD), with tetramethylsilane (TMS) as an internal standard.

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average inhibition rate of kinase and IC$_{50}$ values were determined by a NovoStar ELISA (BMG Co., Germany).

For thin-layer silica gel chromatography (TLC) Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as carrier.

The known starting materials of the invention can be prepared by conventional synthesis methods in the prior art, or can be purchased from ABCR GmbH & Co. KG, Acros Organics, Aldrich Chemical Company, Accela ChemBio Inc., or Dari Chemical Company, etc.

Oxone reagent means 2KHSO$_5$.KHSO$_4$.K$_2$SO$_4$.

Unless otherwise stated, the following reactions were placed under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressured hydrogenation reactions were performed with a Parr 3916EKX hydrogenation spectrometer and a QL-500 hydrogen generator.

In hydrogenation reactions, the reaction system was generally vacuumed and filled with hydrogen, with the above operation repeated three times.

Unless otherwise stated, the solution used in the following reactions refers to an aqueous solution.

Unless otherwise stated, the reaction temperature in the following reactions was room temperature, and the range of the temperature was 20° C. to 30° C.

The reaction process was monitored by thin layer chromatography (TLC), and the system of developing solvent included: A: dichloromethane and methanol, B: n-hexane and ethyl acetate, C: petroleum ether and ethyl acetate, D: acetone. The ratio of the volume of the solvent was adjusted according to the polarity of the compounds.

The elution system for purification of the compounds by column chromatography and thin layer chromatography included: A: dichloromethane and methanol system, B: n-hexane and ethyl acetate system, C: n-hexane and acetone, D: n-hexane, E: ethyl acetate. The volume of the solvent was adjusted according to the polarity of the compounds, and sometimes a little alkaline reagent, such as triethylamine, or acidic reagent, such as acetic acid, was also added.

Example 1

(R)-4-(3-(3-Fluoro-4-((tetrahydrofuran-3-yl)oxy) phenyl)-4,4-dimethyl-5-oxo-2-thioxoimidazolidin-1-yl)-2-(trifluoromethyl)benzonitrile

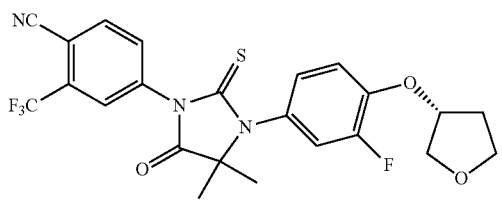

1

53
-continued

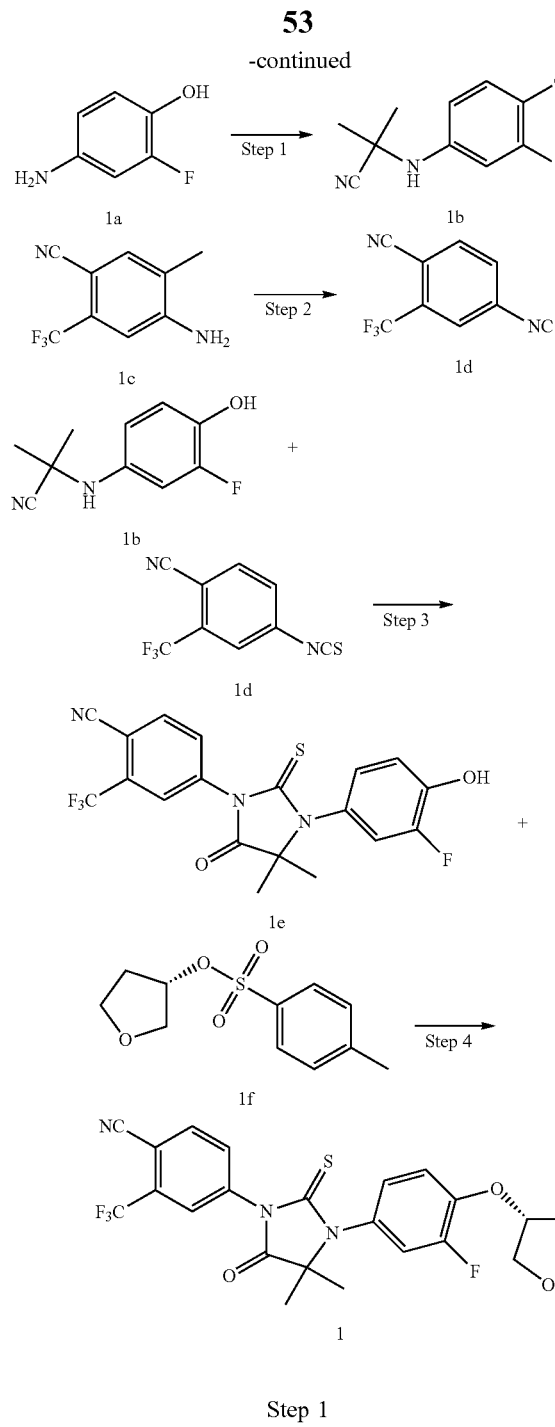

Step 1

2-((3-Fluoro-4-hydroxyphenyl)amino)-2-methylpropanenitrile

4-Amino-2-fluorophenol 1a (6 g, 0.05 mol) was dissolved in 90 mL of a mixture of acetone and dichloromethane (v/v=1:2), followed by addition of trimethylsilyl cyanide (9.4 mL, 0.07 mol) and trifluoromethanesulfonic acid trimethylsilyl ester (0.4 mL, 2.30 mmol). The reaction solution was stirred for 2.5 hours. The reaction solution was concentrated under reduced pressure and the residue was purified by silica gel column chromatography with elution system B to obtain the title compound 2-((3-fluoro-4-hydroxyphenyl)amino)-2-methylpropanenitrile 1b (7.02 g, yield 76.6%) as a brown solid.

MS m/z (ESI): 194.4 [M+1]

54

Step 2

4-Isothiocyanato-2-(trifluoromethyl)benzonitrile

4-Amino-2-(trifluoromethyl)benzonitrile 1c (10 g, 0.05 mol) was dissolved in 60 mL of a mixture of n-hexane and water (v/v=1:1), followed by addition of thiophosgene (4.6 mL, 0.06 mol) in an ice bath (0 to 5° C.). Then, the ice bath was removed, the reaction solution was warmed up to room temperature and reacted for 12 hours, then thiophosgene (3.0 mL, 0.04 mol) was supplemented. After reacting for 24 hours, the reaction was left to stand and separate. The aqueous phase was extracted with a mixture (50 mL) of n-hexane and ethyl acetate (v/v=10:1). The organic phases were combined, washed with saturated sodium chloride solution (50 mL), dried over anhydrous sodium sulfate, and filtered. The filtrate was concentrated under reduced pressure to obtain the title compound 4-isothiocyanato-2-(trifluoromethyl)benzonitrile 1d (10 g, yield 80.8%) as a light brown oil.

Step 3

4-(3-(3-Fluoro-4-hydroxyphenyl)-4,4-dimethyl-5-oxo-2-thioxoimidazolidin-1-yl)-2-(trifluoromethyl)benzonitrile 2-((3-Fluoro-4-hydroxyphenyl)amino)-2-methylpropanenitrile 1b (3 g, 15 mmol) and 4-isothiocyanato-2-(trifluoromethyl)benzonitrile 1d (4.20 g, 18 mmol) were dissolved in 50 mL of N,N-dimethylacetamide and stirred for 3 hours. The reaction solution was mixed with 30 mL of methanol and 30 mL of 2 M hydrochloric acid, and warmed up to 70° C. After reacting for 2 hours, the reaction solution was cooled down to room temperature, mixed with 50 mL of water, and extracted with ethyl acetate (30 mL×3). The organic phases were combined, washed with saturated sodium chloride solution (30 mL×2), dried over anhydrous sodium sulfate, and filtered. The filtrate was concentrated under reduced pressure and the residue was purified by silica gel column chromatography with elution system B to obtain the title compound 4-(3-(3-fluoro-4-hydroxyphenyl)-4,4-dimethyl-5-oxo-2-thioxoimidazolidin-1-yl)-2-(trifluoromethyl)benzonitrile 1e (6 g, yield 91.7%) as a white solid.

MS m/z (ESI): 424.3 [M+1]

Step 4

(R)-4-(3-(3-Fluoro-4-((tetrahydrofuran-3-yl)oxy)phenyl)-4,4-dimethyl-5-oxo-2-thioxoimidazolidin-1-yl)-2-(trifluoromethyl)benzonitrile 4-(3-(3-Fluoro-4-hydroxyphenyl)-4,4-dimethyl-5-oxo-2-thioxoimidazolidin-1-yl)-2-(trifluoromethyl)benzonitrile 1e (80 mg, 0.19 mmol) was placed in a reaction flask, followed by addition of (S)-tetrahydrofuran-3-yl-4-methylbenzenesulfonate 1f (92 mg, 0.38 mmol, prepared by a method disclosed in US Patent Application Publication U.S. 2003/0153752 A1), cesium carbonate (186 mg, 0.57 mmol), and 1 mL of N,N-dimethylacetamide, successively. The reaction solution was warmed up to 50° C. After reacting for 3 hours, the reaction solution was cooled down to room temperature, mixed with 15 mL of H₂O, and extracted with ethyl acetate (15 mL×3). The organic phases were combined, washed with saturated sodium chloride solution (20 mL×2), dried over anhydrous sodium sulfate, and filtered. The filtrate was concentrated under reduced pressure and the residue was purified by silica gel column chromatography with elution system A to obtain the title compound (R)-4-(3-(3-fluoro-4-((tetrahydrofuran-3-yl)oxy)phenyl)-4,4-dimethyl-5-oxo-2-thioxoimidazolidin-1-yl)-2-(trifluoromethyl)benzonitrile 1 (63 mg, yield 67.6%) as a white solid.

MS m/z (ESI): 494.4 [M+1]; $^1$H NMR (400 MHz, CDCl$_3$): δ 7.96-8.00 (m, 2H), 7.84 (d, 1H), 7.00-7.09 (m, 3H), 5.00-5.03 (m, 1H), 4.12-4.14 (m, 2H), 4.06-4.08 (m, 1H), 3.96-4.01 (m, 1H), 2.23-2.26 (m, 2H), 1.59 (s, 6H).

Example 2

(S)-4-(3-(3-Fluoro-4-((tetrahydrofuran-3-yl)oxy) phenyl)-4,4-dimethyl-5-oxo-2-thioxoimidazolidin-1-yl)-2-(trifluoromethyl)benzonitrile

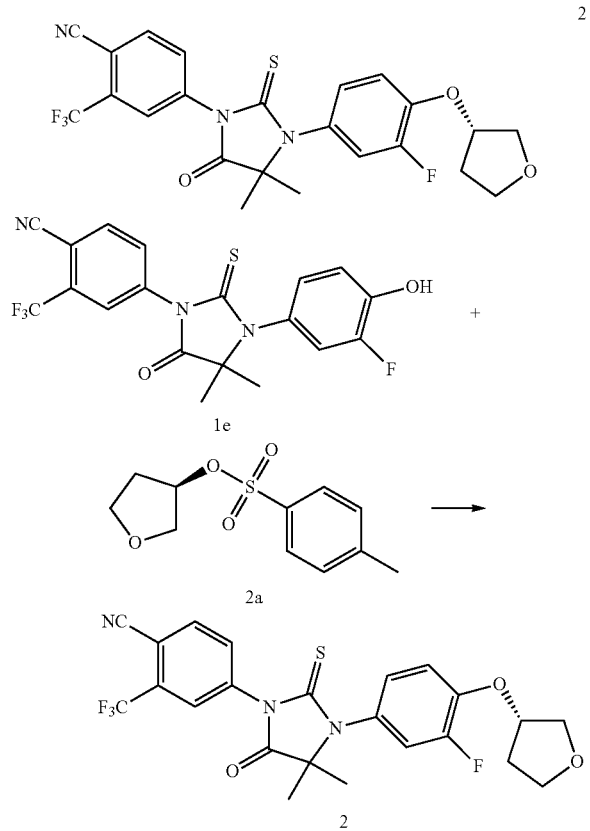

4-(3-(3-Fluoro-4-hydroxyphenyl)-4,4-dimethyl-5-oxo-2-thioxoimidazolidin-1-yl)-2-(trifluoromethyl)benzonitrile 1e (80 mg, 0.19 mmol) was placed in a reaction flask, followed by addition of (R)-tetrahydrofuran-3-yl-4-methylbenzenesulfonate 2a (92 mg, 0.38 mmol, prepared by a well known method described in *Journal of Medicinal Chemistry*, 2011, 54 (12), 4092-4108), cesium carbonate (186 mg, 0.57 mmol), and 3 mL of N,N-dimethylacetamide, successively. The reaction solution was warmed up to 60° C. After reacting for 2 hours, the reaction solution was cooled down to room temperature, mixed with 15 mL of water, and extracted with ethyl acetate (25 mL×3). The organic phases were combined, washed with saturated sodium chloride solution (10 mL×3), dried over anhydrous sodium sulfate, and filtered. The filtrate was concentrated under reduced pressure and the residue was purified by thin layer chromatography with elution system B to obtain the title compound (S)-4-(3-(3-fluoro-4-((tetrahydrofuran-3-yl)oxy)phenyl)-4,4-dimethyl-5-oxo-2-thioxoimidazolidin-1-yl)-2-(trifluoromethyl)benzonitrile 2 (73 mg, yield 77.9%) as a pale yellow solid.

MS m/z (ESI): 494.4 [M+1]; $^1$H NMR (400 MHz, CDCl$_3$): δ 8.00-7.06 (m, 2H), 7.84 (q, 1H), 7.08 (d, 1H), 7.04-7.03 (m, 2H), 5.04-5.02 (m, 1H), 4.07-3.94 (m, 4H), 2.29-2.24 (m, 2H), 1.60 (s, 6H).

Example 3

4-(3-(4-(Difluoromethoxy)-3-fluorophenyl)-4,4-dimethyl-5-oxo-2-thioxoimidazolidin-1-yl)-2-(trifluoromethyl)benzonitrile

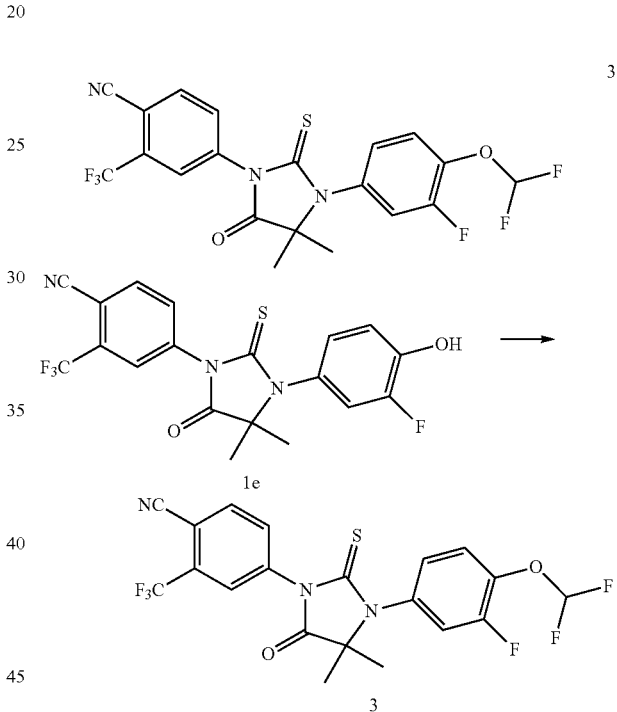

4-(3-(3-Fluoro-4-hydroxyphenyl)-4,4-dimethyl-5-oxo-2-thioxoimidazolidin-1-yl)-2-(trifluoromethyl)benzonitrile 1e (300 mg, 0.71 mmol) was dissolved in 10 mL of a mixture of acetonitrile and water (v/v=1:1), followed by addition of potassium hydroxide (79 mg, 1.42 mmol) and bromodifluoromethane diethyl phosphate (0.15 mL, 0.85 mmol) successively in an ice bath (0° C.). The reaction solution was warmed up to room temperature, stirred for 12 hours, then mixed with 20 mL of water and extracted with ethyl acetate (20 mL×3). The organic phases were combined, washed with saturated sodium chloride solution (20 mL), dried over anhydrous sodium sulfate, and filtered. The filtrate was concentrated under the reduced pressure, and the residue was purified by silica gel column chromatography with elution system D and thin layer chromatography with elution system D, successively, to obtain the title compound 4-(3-(4-(difluoromethoxy)-3-fluorophenyl)-4,4-dimethyl-5-oxo-2-thioxoimidazolidin-1-yl)-2-(trifluoromethyl)benzonitrile 3 (90 mg, yield 26.8%) as a white solid.

MS m/z (ESI): 474.3 [M+1]; $^1$H NMR (400 MHz, CDCl$_3$): δ 7.96-7.99 (m, 2H), 7.84 (d, 1H), 7.44 (s, 1H), 7.13-7.20 (m, 2H), 6.66 (t, 1H), 1.62 (s, 6H).

Example 4

4-(3-(3-Fluoro-4-((tetrahydro-2H-pyran-4-yl)oxy) phenyl)-4,4-dimethyl-5-oxo-2-thioxoimidazolidin-1-yl)-2-(trifluoromethyl)benzonitrile

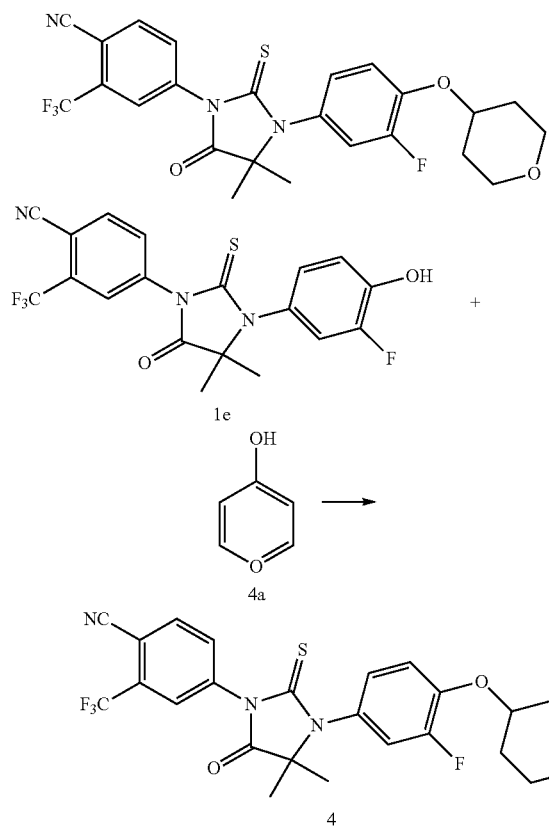

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of tetrahydro-2H-pyran-4-ol 4a (29 mg, 0.28 mmol, prepared by a method disclosed in U.S. Patent Application Publication U.S. 2011/71196 A1), 1,1'-(azodicarbonyl)dipiperidine (95 mg, 0.38 mmol), 10 mL of methylbenzene and tri-n-butylphosphine (94 μL, 0.38 mmol), successively. The reaction solution was warmed up to 50° C. and stirred for 3 hours. The reaction solution was concentrated under reduced pressure, and the residue was purified by silica gel column chromatography with elution system A to obtain the title compound 4-(3-(3-fluoro-4-((tetrahydro-2H-pyran-4-yl)oxy)phenyl)-4,4-dimethyl-5-oxo-2-thioxoimidazolidin-1-yl)-2-(trifluoromethyl)benzonitrile 4 (82 mg, yield 68.4%) as a white solid.

MS m/z (ESI): 508.3 [M+1]; $^1$H NMR (400 MHz, CDCl$_3$): δ 7.96-8.00 (m, 2H), 7.84 (d, 1H), 7.03-7.13 (m, 3H), 4.58-4.59 (m, 1H), 4.00-4.03 (m, 2H), 3.59-3.63 (m, 2H), 2.05-2.08 (m, 2H), 1.87-1.91 (m, 2H), 1.59 (s, 6H).

Example 5

4-(3-(3-Fluoro-4-((1-hydroxycyclopropyl)methoxy) phenyl)-4,4-dimethyl-5-oxo-2-thioxoimidazolidin-1-yl)-2-(trifluoromethyl)benzonitrile

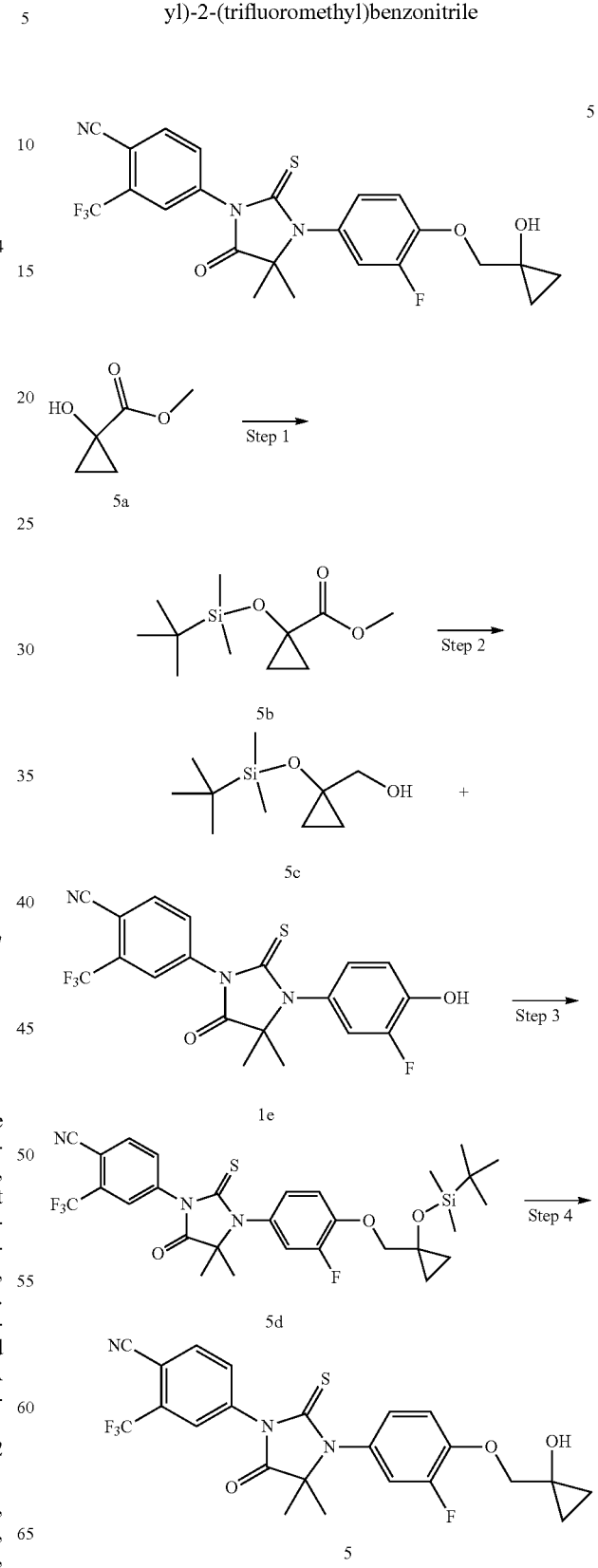

Step 1

Methyl 1-(tert-butyldimethylsilyloxy)cyclopropanecarboxylate

Methyl 1-hydroxycyclopropanecarboxylate 5a (350 mg, 3.02 mmol) was dissolved in 30 mL of dichloromethane, followed by addition of tert-butyldimethylsilyl chloride (495 mg, 3.30 mmol) and imidazole (306 mg, 4.49 mmol). After reacting for 12 hours, the reaction mixture was mixed with 20 mL of dichloromethane, and extracted with saturated sodium chloride solution (20 mL×3), dried over anhydrous sodium sulfate, and filtered. The filtrate was concentrated under reduced pressure to obtain the crude title product methyl 1-(tert-butyldimethylsilyloxy)cyclopropanecarboxylate 5b (600 mg, colourless oil), which was used directly in the next step without further purification.

Step 2

(1-((tert-Butyldimethylsilyl)oxy)cyclopropyl)methanol

Methyl 1-(tert-butyldimethylsilyloxy)cyclopropanecarboxylate 5b (600 mg, 2.61 mmol) was dissolved in 30 mL of tetrahydrofuran and cooled down to −40° C. in an dry ice-acetone bath, followed by addition of diisobutyl aluminum hydride (7.8 mL, 7.80 mmol). The reaction solution was stirred for 3 hours at −40° C., followed by addition of 20 mL of H$_2$O. The reaction solution was warmed up to room temperature and stirred for 10 minutes to quench the reaction. The reaction mixture was filtered. The filtrate was extracted with ethyl acetate (20 mL×2). The organic phases were combined, washed with saturated sodium chloride solution (20 mL×3), dried over anhydrous sodium sulfate, and filtered. The filtrate was concentrated under reduced pressure to obtain the crude title product (1-((tert-butyldimethylsilyl)oxy)cyclopropyl)methanol 5c (500 mg, clear oil), which was used directly in the next step without further purification.

Step 3

4-(3-(4-((1-(((tert-Butyldimethylsilyl)oxy)cyclopropyl)methoxy)-3-fluorophenyl)-4,4-dimethyl-5-oxo-2-thioxoimidazolidin-1-yl)-2-(trifluoromethyl)benzonitrile (1-((tert-Butyldimethylsilyl)oxy)cyclopropyl)methanol 5c (500 mg, 0.23 mmol) was placed in a reaction flask, followed by addition of 4-(3-(3-fluoro-4-hydroxyphenyl)-4,4-dimethyl-5-oxo-2-thioxoimidazolidin-1-yl)-2-(trifluoromethyl)benzonitrile 1e (80 mg, 0.19 mmol), 1,1'-(azodicarbonyl)dipiperidine (77 mg, 0.31 mmol), 5 mL of methylbenzene, and tri-n-butylphosphine (61 mg, 0.31 mmol), successively. The reaction solution was warmed up to 50° C. and stirred for 2 hours. The reaction solution was dissolved in a small amount of methanol, and purified by thin layer chromatography with elution system B to obtain the title compound 4-(3-(4-((1-(((tert-butyldimethylsilyl)oxy)cyclopropyl)methoxy)-3-fluorophenyl)-4,4-dimethyl-5-oxo-2-thioxoimidazolidin-1-yl)-2-(trifluoromethyl)benzonitrile 5d (73 mg, yield 63.3%) as a yellow oil.

Step 4

4-(3-(3-Fluoro-4-((1-hydroxycyclopropyl)methoxy)phenyl)-4,4-dimethyl-5-oxo-2-thioxoimidazolidin-1-yl)-2-(trifluoromethyl)benzonitrile 4-(3-(4-((1-(((tert-Butyldimethylsilyl)oxy)cyclopropyl)methoxy)-3-fluorophenyl)-4,4-dimethyl-5-oxo-2-thioxoimidazolidin-1-yl)-2-(trifluoromethyl)benzonitrile 5d (73 mg, 0.12 mmol) was dissolved in 7 mL of tetrahydrofuran, followed by addition of tetrabutylammonium fluoride (0.13 mL, 0.13 mmol). The reaction solution was stirred for 1 hour. The reaction solution was concentrated under reduced pressure, mixed with 5 mL of H$_2$O, and extracted with ethyl acetate (20 mL). The organic phases were combined, washed with saturated sodium chloride solution (10 mL×3), dried over anhydrous sodium sulfate, and filtered. The filtrate was concentrated under reduced pressure, and the resulting residue was purified by thin layer chromatography with elution system A to obtain the title product 4-(3-(3-fluoro-4-((1-hydroxycyclopropyl)methoxy)phenyl)-4,4-dimethyl-5-oxo-2-thioxoimidazolidin-1-yl)-2-(trifluoromethyl)benzonitrile 5 (50 mg, yield 84.4%) as a white solid.

MS m/z (ESI): 494.4 [M+1]; $^1$H NMR (400 MHz, CDCl$_3$): δ 8.00-7.96 (m, 2H), 7.85-7.83 (m, 1H), 7.13-7.03 (m, 3H), 4.15 (s, 2H), 1.60 (s, 6H), 1.04-1.00 (m, 2H), 0.77-0.74 (m, 2H).

Example 6

4-(3-(4-((1-Aminocyclopropyl)methoxy)-3-fluorophenyl)-4,4-dimethyl-5-oxo-2-thioxoimidazolidin-1-yl)-2-(trifluoromethyl)benzonitrile

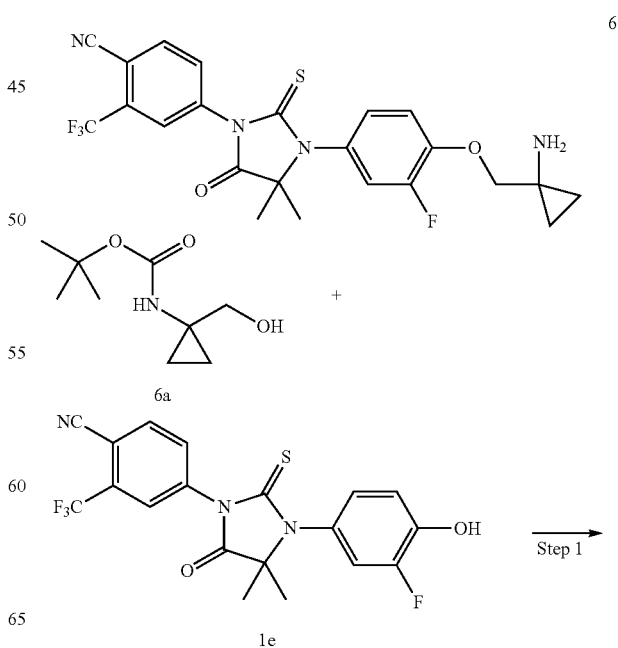

-continued

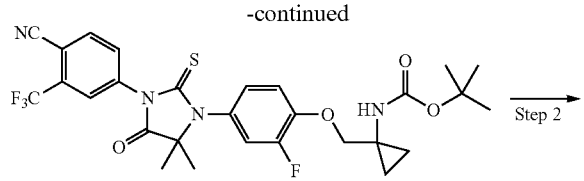

6b

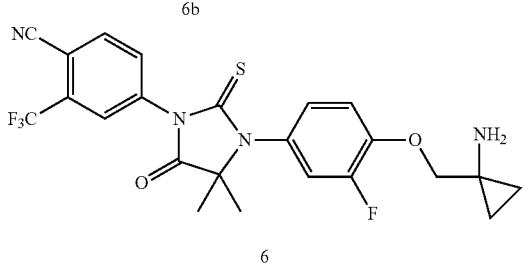

6

Step 1 tert-Butyl (1-((4-(3-(4-cyano-3-(trifluoromethyl)phenyl)-5,5-dimethyl-4-oxo-2-thioxoimidazolidin-1-yl)-2-fluorophenoxy)methyl)cyclopropyl)carbamate tert-Butyl (1-(hydroxymethyl)cyclopropyl)carbamate 6a (53 mg, 0.28 mmol) was placed in a reaction flask, followed by addition of 4-(3-(3-fluoro-4-hydroxyphenyl)-4,4-dimethyl-5-oxo-2-thioxoimidazolidin-1-yl)-2-(trifluoromethyl)benzonitrile 1e (100 mg, 0.24 mmol), 1,1'-(azodicarbonyl)dipiperidine (95 mg, 0.38 mmol), 5 mL of methylbenzene, and tri-n-butylphosphine (76 mg, 0.38 mmol), successively. The reaction solution was warmed up to 50° C. and stirred for 2 hours. The reaction solution was dissolved in a small amount of methanol, and purified by thin layer chromatography with elution system A to obtain the title compound tert-butyl (1-((4-(3-(4-cyano-3-(trifluoromethyl)phenyl)-5,5-dimethyl-4-oxo-2-thioxoimidazolidin-1-yl)-2-fluorophenoxy)methyl)cyclopropyl)carbamate 6b (115 mg, yield 82.3%) as a white solid.

Step 2

4-(3-(4-((1-Aminocyclopropyl)methoxy)-3-fluorophenyl)-4,4-dimethyl-5-oxo-2-thioxoimidazolidin-1-yl)-2-(trifluoromethyl)benzonitrile tert-Butyl (1-((4-(3-(4-cyano-3-(trifluoromethyl)phenyl)-5,5-dimethyl-4-oxo-2-thioxoimidazolidin-1-yl)-2-fluorophenoxy)methyl)cyclopropyl)carbamate 6b (115 mg, 0.19 mmol) was dissolved in 4 mL of a solution of 2 M hydrogen chloride in methanol. The reaction solution was stirred for 4 hours, followed by addition of 2 N aqueous sodium hydroxide solution to adjust the pH to 7. Most of the methanol was evaporated, and the reaction solution was extracted with ethyl acetate (30 mL). The organic phases were dried over anhydrous magnesium sulfate, and filtered. The filtrate was concentrated under reduced pressure to obtain the title product 4-(3-(4-((1-aminocyclopropyl) methoxy)-3-fluorophenyl)-4,4-dimethyl-5-oxo-2-thioxoimidazolidin-1-yl)-2-(trifluoromethyl)benzonitrile 6 (97 mg, yield 94.7%) as a white solid.

MS m/z (ESI): 493.4 [M+1]; $^1$H NMR (400 MHz, CDCl$_3$): δ 8.41-8.39 (m, 1H), 8.28-8.27 (m, 1H), 8.08-8.05 (m, 1H), 7.40-7.34 (m, 2H), 7.21-7.19 (m, 1H), 4.25 (s, 2H), 1.51 (s, 6H), 1.14-1.11 (m, 2H), 1.12-0.99 (m, 2H).

Example 7

4-(3-(3-Fluoro-4-(((3R,4R/3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile

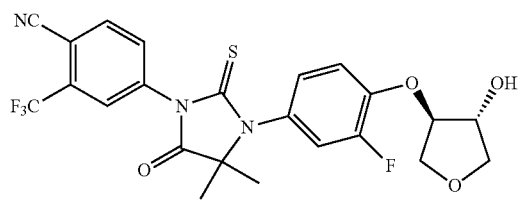

7

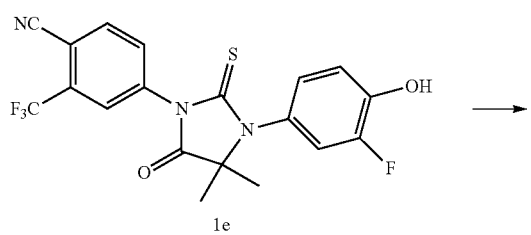 + 

1e

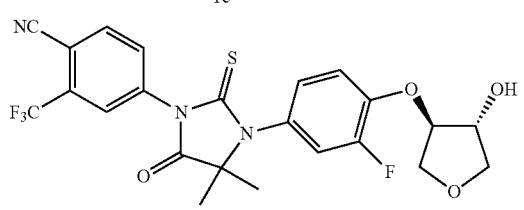 + 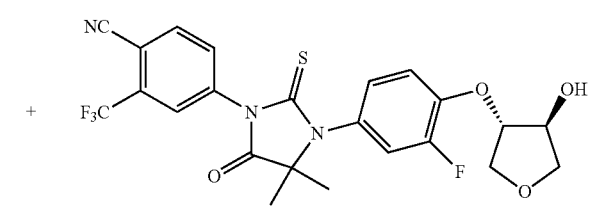

7

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of 3,4-epoxy-tetrahydrofuran (24 mg, 0.28 mmol), cesium carbonate (115 mg, 0.35 mmol), and 4 mL of N,N-dimethylacetamide, successively. The reaction mixture was warmed up to 120° C. After reacting for 1 hour, the reaction solution was supplemented with 3,4-epoxy-tetrahydrofuran (100 mg, 1.16 mmol), and stirred at 120° C. for another 1 hour. The reaction solution was mixed with 30 mL of H₂O and extracted with ethyl acetate (30 mL). The organic phases were combined, washed with water (15 mL×3) and saturated sodium chloride solution (15 mL×3), dried over anhydrous sodium sulfate, and filtered. The filtrate was concentrated under reduced pressure, and the residue was purified by thin layer chromatography with elution system A and subsequently with elution system B to obtain the title compound 4-(3-(3-fluoro-4-(((3R,4R/3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile 7 (40 mg, yield 33.3%) as a white solid.

MS m/z (ESI): 510.3 [M+1]; ¹H NMR (400 MHz, CDCl₃): δ 8.00-7.96 (m, 2H), 7.85-7.82 (m, 1H), 7.19-7.15 (t, 1H), 7.08-7.04 (m, 2H), 4.81-4.80 (m, 1H), 4.52-4.50 (m, 1H), 4.33-4.29 (m, 1H), 4.14-4.10 (m, 1H), 4.03-4.00 (m, 1H), 3.88-3.86 (m, 1H), 1.60 (s, 6H).

Examples 8, 9

4-(3-(3-Fluoro-4-(((3R,4R)-4-hydroxytetrahydrofuran-3-yl)oxy)phenyl)-4,4-dimethyl-5-oxo-2-thioxoimidazolidin-1-yl)-2-(trifluoromethyl)benzonitrile 4-(3-(3-Fluoro-4-(((3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile

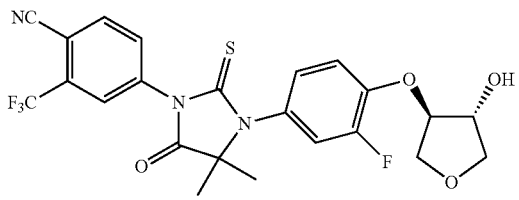

8

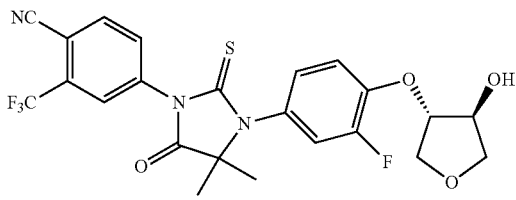

9

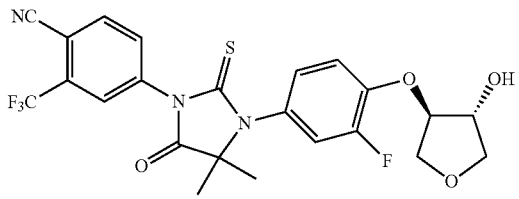

7

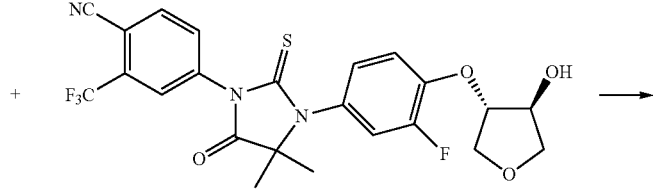

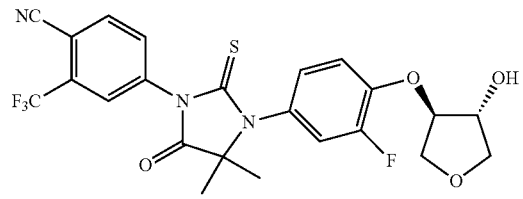

8

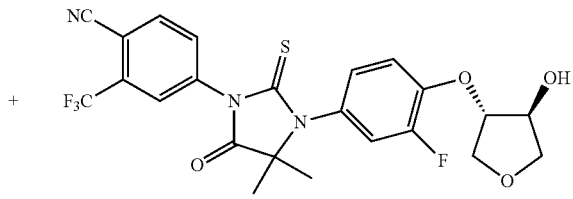

9

4-(3-(3-Fluoro-4-(((3R,4R/3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile 7 (320 mg, 0.63 mmol) was separated by chiral HPLC (separation condition: chiral column CHIRALCEL IC, mobile phase: n-hexane:isopropanol=85:15, flow rate: 15 mL/minute). The corresponding fractions were collected, and evaporated to remove the solvent to obtain the title product 4-(3-(3-fluoro-4-(((3R,4R)-4-hydroxytetrahydrofuran-3-yl)oxy)phenyl)-4,4-dimethyl-5-oxo-2-thioxoimidazolidin-1-yl)-2-(trifluoromethyl)benzonitrile 8 (130 mg, 0.26 mmol) and 4-(3-(3-fluoro-4-(((3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile 9 (130 mg, 0.26 mmol).

8: MS m/z (ESI): 510.3 [M+1], retention time=26.958 minutes, ee value>99.0%.

9: MS m/z (ESI): [M+1], retention time=32.291 minutes, ee value>99.0%.

8: $^1$H NMR (400 MHz, CDCl$_3$): δ 8.00-7.96 (m, 2H), 7.85-7.82 (m, 1H), 7.19-7.15 (t, 1H), 7.08-7.04 (m, 2H), 4.81-4.80 (m, 1H), 4.52-4.50 (m, 1H), 4.33-4.29 (m, 1H), 4.14-4.10 (m, 1H), 4.03-4.00 (m, 1H), 3.88-3.86 (m, 1H), 1.60 (s, 6H).

9: $^1$H NMR (400 MHz, CDCl$_3$): δ 8.00-7.96 (m, 2H), 7.85-7.82 (m, 1H), 7.19-7.15 (t, 1H), 7.08-7.04 (m, 2H), 4.81-4.80 (m, 1H), 4.52-4.50 (m, 1H), 4.33-4.29 (m, 1H), 4.14-4.10 (m, 1H), 4.03-4.00 (m, 1H), 3.88-3.86 (m, 1H), 1.60 (s, 6H).

Example 10

4-(3-(6-(2-Hydroxyethoxy)pyridin-3-yl)-4,4-dimethyl-5-oxo-2-thioxoimidazolidin-1-yl)-2-(trifluoromethyl)benzonitrile

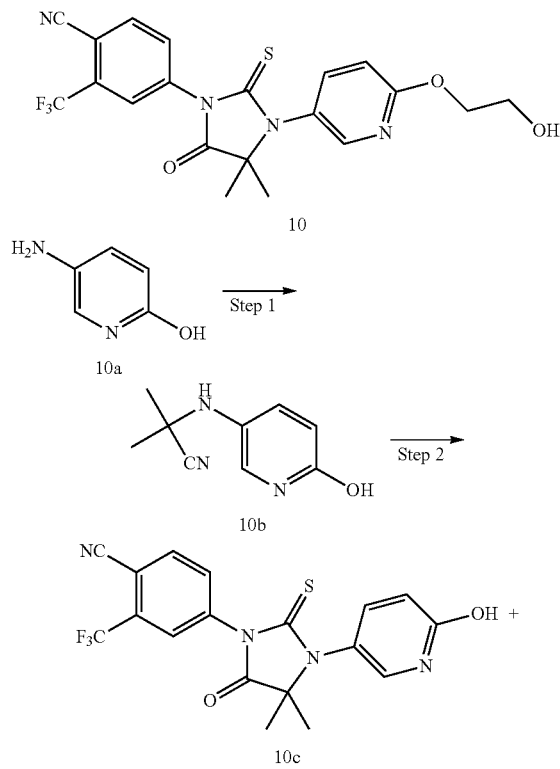

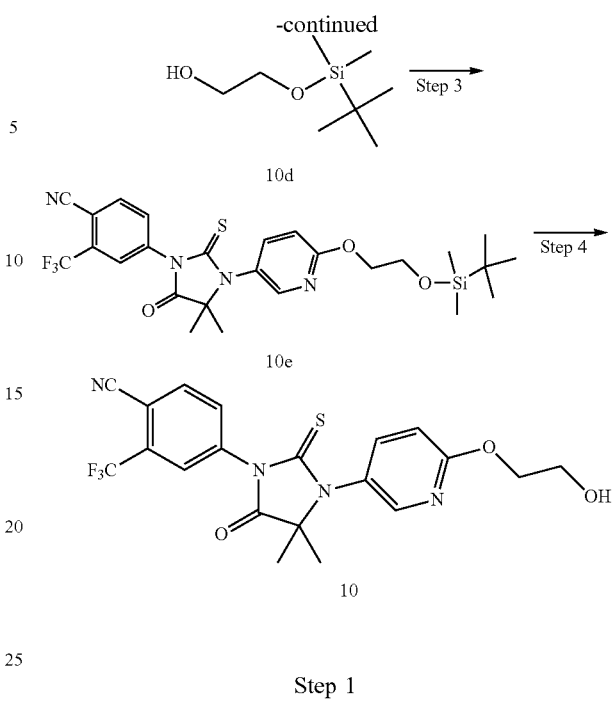

Step 1

2-((6-Hydroxypyridin-3-yl)amino)-2-methylpropanenitrile

5-Aminopyridin-2-ol 10a (400 mg, 3.63 mmol) was dissolved in 9 mL of a mixture of acetone and dichloromethane (v/v=1:2), followed by addition of trimethylsilyl cyanide (0.7 mL, 5.40 mmol) and trifluoromethanesulfonic acid trimethylsilyl ester (33 μL, 0.18 mmol). The reaction solution was stirred for 12 hours. The resulting solution was concentrated under reduced pressure, and the residue was purified by silica gel column chromatography with elution system A to obtain the title compound 2-((6-hydroxypyridin-3-yl)amino)-2-methylpropanenitrile 10b (507 mg, yield 79.5%) as a brown solid.

MS m/z (ESI): 178.2 [M+1]

Step 2

4-(3-(6-Hydroxypyridin-3-yl)-4,4-dimethyl-5-oxo-2-thioxoimidazolidin-1-yl)-2-(trifluoromethyl)benzonitrile 2-((6-Hydroxypyridin-3-yl)amino)-2-methylpropanenitrile 10b (167 mg, 0.94 mmol) and 4-amino-2-(trifluoromethyl)benzonitrile 1c (175 mg, 0.94 mmol) were dissolved in 5 mL of N,N-dimethylacetamide, followed by addition of thiophosgene (72 μL, 0.94 mmol). The reaction solution was warmed up to 60° C. and stirred for 12 hours, followed by addition of 4 mL of methanol and 2 mL of concentrated hydrochloric acid. The reaction solution was cooled down to room temperature and extracted with ethyl acetate (10 mL×3). The organic phases were combined, dried over anhydrous sodium sulfate, and filtered. The filtrate was concentrated under reduced pressure and the residue was purified by thin layer chromatography with elution system A to obtain the title compound 4-(3-(6-hydroxypyridin-3-yl)-4,4-dimethyl-5-oxo-2-thioxoimidazolidin-1-yl)-2-(trifluoromethyl)benzonitrile 10c (200 mg, yield 51.9%) as a gray solid.

Step 3

4-(3-(6-(2-((tert-butyldimethylsilyl)oxy)ethoxy)pyridin-3-yl)-4,4-dimethyl-5-oxo-2-thioxoimidazolidin-1-yl)-2-(trifluoromethyl)benzonitrile 4-(3-(6-Hydroxypyridin-3-yl)-4,4-dimethyl-5-oxo-2-thioxoimidazolidin-1-yl)-2-(trifluoromethyl)benzonitrile 10c (55 mg, 0.14 mmol) was placed in a reaction flask, followed by addition of 2-((tert-butyldimethylsilyl)oxy) ethanol 10d (48 mg, 0.27 mmol, prepared by a well known method described in *Bioorganic & Medicinal Chemistry*, 2006, 14(7), 2375-2385), triphenylphosphine (53 mg, 0.20 mmol), 5 mL of dichloromethane, and diisopropyl azodicarboxylate (41 mg, 0.20 mmol), successively. The reaction solution was stirred for 2 hours. The reaction solution was concentrated under reduced pressure and the residue was purified by thin layer chromatography with elution system B to obtain the title compound 4-(3-(6-(2-((tert-butyldimethylsilyl)oxy)ethoxy)pyridin-3-yl)-4,4-dimethyl-5-oxo-2-thioxoimidazolidin-1-yl)-2-(trifluoromethyl)benzonitrile 10e (28 mg, yield 18.4%) as a white solid.

MS m/z (ESI): 565.3 [M+1]

Step 4

4-(3-(6-(2-Hydroxyethoxy)pyridin-3-yl)-4,4-dimethyl-5-oxo-2-thioxoimidazolidin-1-yl)-2-(trifluoromethyl)benzonitrile 4-(3-(6-(2-((tert-Butyldimethylsilyl)oxy)ethoxy)pyridin-3-yl)-4,4-dimethyl-5-oxo-2-thioxoimidazolidin-1-yl)-2-(trifluoromethyl)benzonitrile 10e (28 mg, 0.05 mmol) was dissolved in 3 mL of tetrahydrofuran, followed by addition of tetrabutylammonium fluoride (54 μL, 0.05 mmol). The reaction solution was stirred for 1 hour. The reaction solution was concentrated under reduced pressure, mixed with ethyl acetate (30 mL), washed with saturated sodium chloride solution (10 mL×3), dried over anhydrous sodium sulfate, and filtered. The filtrate was concentrated under reduced pressure, and the resulting residue was purified by thin layer chromatography with elution system B, and subsequently with elution system A to obtain the title product 4-(3-(6-(2-hydroxyethoxy)pyridin-3-yl)-4,4-dimethyl-5-oxo-2-thioxoimidazolidin-1-yl)-2-(trifluoromethyl)benzonitrile 10 (9 mg, yield 40.9%) as a white solid.

MS m/z (ESI): 451.2 [M+1]; $^1$H NMR (400 MHz, CDCl$_3$): δ 8.10-8.09 (m, 1H), 8.01-7.97 (m, 2H), 7.86-7.83 (m, 1H), 7.57-7.55 (m, 1H), 6.99-6.96 (m, 1H), 4.55-4.53 (m, 2H), 4.02-4.00 (m, 2H), 1.60 (s, 6H).

Example 11

4-(3-(6-((1-Aminocyclopropyl)methoxy)pyridin-3-yl)-4,4-dimethyl-5-oxo-2-thioxoimidazolidin-1-yl)-2-(trifluoromethyl)benzonitrile

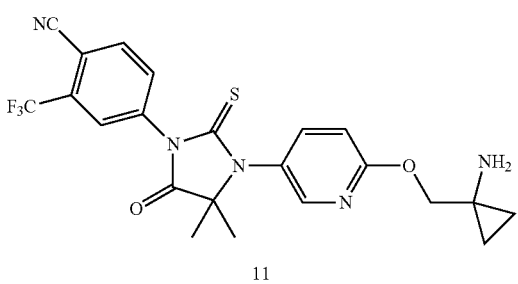

11

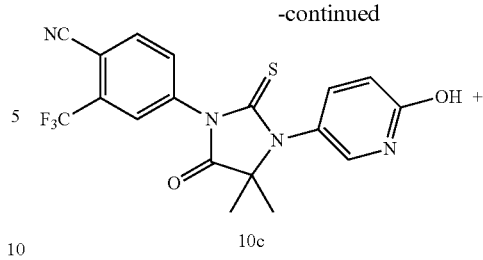

10c

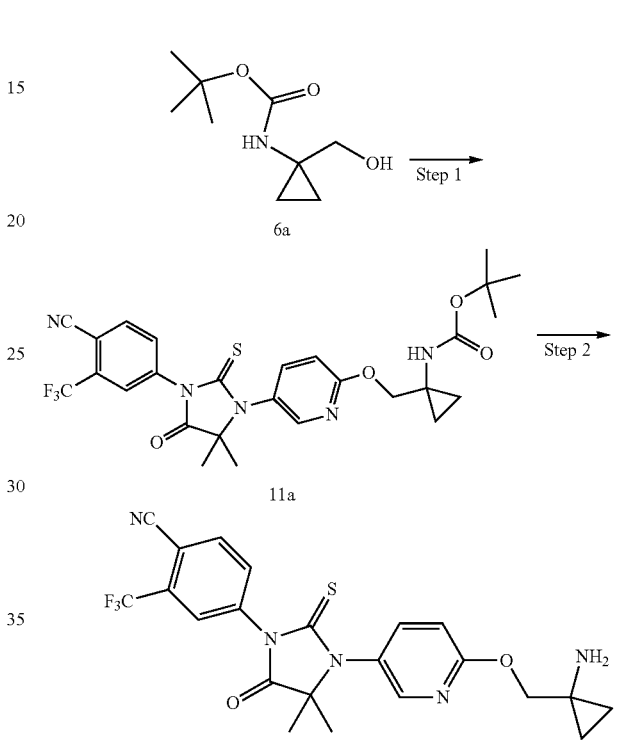

Step 1 tert-butyl (1-(((5-(3-(4-Cyano-3-(trifluoromethyl)phenyl)-5,5-dimethyl-4-oxo-2-thioxoimidazolidin-1-yl)pyridin-2-yl)oxy)methyl)cyclopropyl)carbamate tert-Butyl (1-(hydroxymethyl)cyclopropyl)carbamate 6a (92 mg, 0.49 mmol) was placed in a reaction flask, followed by addition of 4-(3-(6-hydroxypyridin-3-yl)-4,4-dimethyl-5-oxo-2-thioxoimidazolidin-1-yl)-2-(trifluoromethyl)benzonitrile 10c (100 mg, 0.24 mmol), triphenylphosphine (97 mg, 0.37 mmol), 5 mL of dichloromethane, and diisopropyl azodicarboxylate (75 mg, 0.37 mmol), successively. The reaction solution was stirred for 2 hours. The reaction solution was purified by thin layer chromatography with elution system A, and subsequently with elution system B to obtain the title compound tert-butyl (1-(((5-(3-(4-cyano-3-(trifluoromethyl)phenyl)-5,5-dimethyl-4-oxo-2-thioxoimidazolidin-1-yl)pyridin-2-yl)oxy)methyl)cyclopropyl)carbamate 11a (40 mg, yield 28.4%) as a white solid.

MS m/z (ESI): 576.2 [M+1]

Step 2

4-(3-(6-((1-Aminocyclopropyl)methoxy)pyridin-3-yl)-4,4-dimethyl-5-oxo-2-thioxoimidazolidin-1-yl)-2-(trifluoromethyl)benzonitrile tert-Butyl (1-(((5-(3-(4-cyano-3-(trifluoromethyl)phenyl)-5,5-dimethyl-4-oxo-2-thioxoimidazolidin-1-yl)pyridin-2-yl)oxy)methyl)cyclopropyl)carbamate 11a (40 mg, 0.07 mmol) was dissolved in 5 mL of a solution of 2 M hydrogen chloride in methanol. The reaction solution was stirred for 1 hour, followed by addition of 2 N aqueous sodium hydroxide solution to adjust the pH to 7. Most of the methanol was evaporated, and the reaction solution was extracted with ethyl acetate (20 mL). The organic phases were dried over anhydrous magnesium sulfate, and filtered. The filtrate was concentrated under reduced pressure to obtain the title product 4-(3-(6-((1-aminocyclopropyl)methoxy)pyridin-3-yl)-4,4-dimethyl-5-oxo-2-thioxoimidazolidin-1-yl)-2-(trifluoromethyl)benzonitrile 11 (35 mg, yield 98.5%) as a yellow solid.

MS m/z (ESI): 476.2 [M+1]; $^1$H NMR (400 MHz, CDCl$_3$): δ 8.19-8.16 (m, 3H), 8.00-7.98 (m, 1H), 7.80-7.78 (m, 1H), 7.10-7.08 (m, 1H), 4.53 (s, 2H), 1.57 (s, 6H), 1.24-1.13 (m, 4H).

Example 12

4-(3-(3-Fluoro-4-(2-hydroxyethoxy)phenyl)-4,4-dimethyl-5-oxo-2-thioxoimidazolidin-1-yl)-2-(trifluoromethyl)benzonitrile 0.24 mmol), successively. The reaction solution was warmed up to 80° C. After reacting for 12 hours, the reaction solution was cooled down to room temperature, mixed with 20 mL of water, and extracted with ethyl acetate (15 mL×3). The organic phases were combined, washed with saturated sodium chloride solution (20 mL×3), dried over anhydrous sodium sulfate, and filtered. The filtrate was concentrated under reduced pressure, and the residue was purified by silica gel column chromatography with elution system B, and subsequently with elution system A to obtain the title compound 4-(3-(3-fluoro-4-(2-hydroxyethoxy)phenyl)-4,4-dimethyl-5-oxo-2-thioxoimidazolidin-1-yl)-2-(trifluoromethyl)benzonitrile 12 (25 mg, yield 45.3%) as a white solid.

MS m/z (ESI): 556.2 [M+1]; $^1$H NMR (400 MHz, CDCl$_3$): δ 7.96-7.99 (m, 2H), 7.83 (d, 1H), 7.04-7.15 (m, 3H), 4.22 (t, 2H), 4.03 (t, 2H), 1.59 (s, 6H).

Example 13

4-(3-(4-(2,3-Dihydroxypropoxy)-3-fluorophenyl)-4,4-dimethyl-5-oxo-2-thioxoimidazolidin-1-yl)-2-(trifluoromethyl)benzonitrile

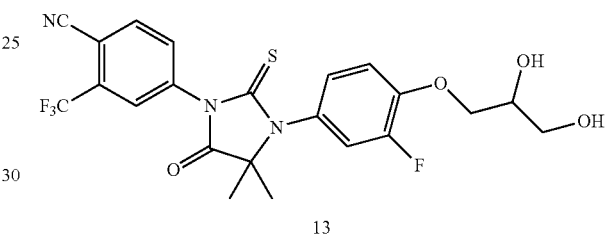

13

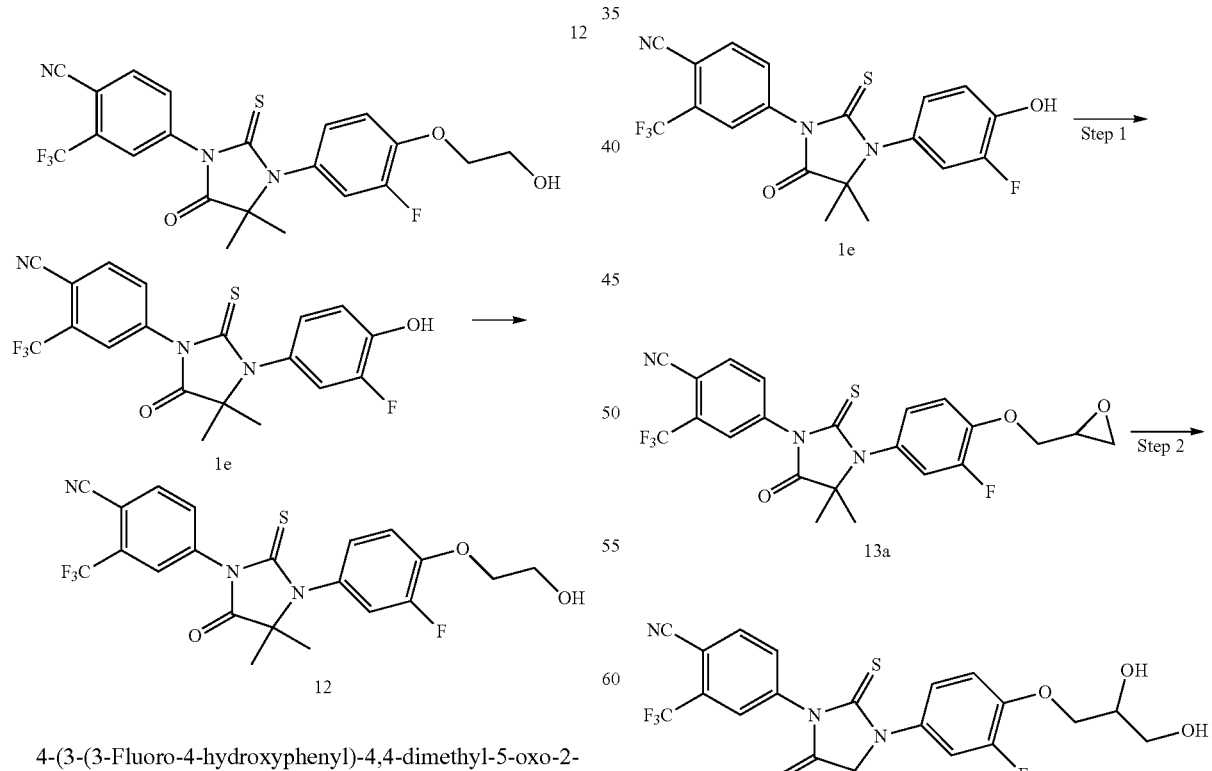

4-(3-(3-Fluoro-4-hydroxyphenyl)-4,4-dimethyl-5-oxo-2-thioxoimidazolidin-1-yl)-2-(trifluoromethyl)benzonitrile 1e (50 mg, 0.12 mmol) was placed in a reaction flask, followed by addition of potassium carbonate (33 mg, 0.24 mmol), 2 mL of N,N-dimethylformamide, and bromoethanol (30 mg,

Step 1

4-(3-(3-Fluoro-4-(oxiran-2-ylmethoxy)phenyl)-4,4-dimethyl-5-oxo-2-thioxoimidazolidin-1-yl)-2-(trifluoromethyl)benzonitrile 4-(3-(3-fluoro-4-hydroxyphenyl)-4,4-dimethyl-5-oxo-2-thioxoimidazolidin-1-yl)-2-(trifluoromethyl)benzonitrile 1e (500 mg, 1.18 mmol) was was dissolved in 20 mL of acetonitrile, followed by addition of epoxy chloropropane (218 mg, 2.36 mmol) and potassium carbonate (407 mg, 2.95 mmol), successively. The reaction solution was warmed up to 80° C. and refluxed for 12 hours. The reaction solution was cooled down to room temperature, mixed with 20 mL of water, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system A to obtain the title compound 4-(3-(3-fluoro-4-(oxiran-2-ylmethoxy)phenyl)-4,4-dimethyl-5-oxo-2-thioxoimidazolidin-1-yl)-2-(trifluoromethyl)benzonitrile 13a (300 mg, yield 53.0%) as a white solid.

MS m/z (ESI): 480.2 [M+1]

Step 2

4-(3-(4-(2,3-Dihydroxypropoxy)-3-fluorophenyl)-4,4-dimethyl-5-oxo-2-thioxoimidazolidin-1-yl)-2-(trifluoromethyl)benzonitrile 4-(3-(3-Fluoro-4-(oxiran-2-ylmethoxy)phenyl)-4,4-dimethyl-5-oxo-2-thioxoimidazolidin-1-yl)-2-(trifluoromethyl)benzonitrile 13a (100 mg, 0.21 mmol) was dissolved in 10 mL of a mixture of water and tetrahydrofuran (v/v=1:1), followed by addition of 0.2 mL of concentrated sulfuric acid. The reaction solution was heated under reflux for 4 hours. The reaction solution was cooled down to room temperature, mixed with 10 mL of 1 M sodium hydroxide solution, and extracted with ethyl acetate (30 mL×2). The organic phases were combined, washed with saturated sodium chloride solution (20 mL×2), dried over anhydrous sodium sulfate, and filtered. The filtrate was concentrated under reduced pressure, and the residue was purified by silica gel column chromatography with elution system A to obtain the title compound 4-(3-(4-(2,3-dihydroxypropoxy)-3-fluorophenyl)-4,4-dimethyl-5-oxo-2-thioxoimidazolidin-1-yl)-2-(trifluoromethyl)benzonitrile 13 (40 mg, yield 40.0%) as a white solid.

MS m/z (ESI): 498.3 [M+1]; $^1$H NMR (400 MHz, CDCl$_3$): δ 7.99-7.95 (m, 2H), 7.84-7.82 (m, 1H), 7.15-7.04 (m, 3H), 4.22-4.18 (m, 3H), 3.91-3.79 (m, 2H), 1.59 (s, 6H).

Example 14

4-(3-(4-(((3R,4R/3S,4S)-4-Hydroxytetrahydrofuran-3-yl)oxy)phenyl)-4,4-dimethyl-5-oxo-2-thioxoimidazolidin-1-yl)-2-(trifluoromethyl)benzonitrile

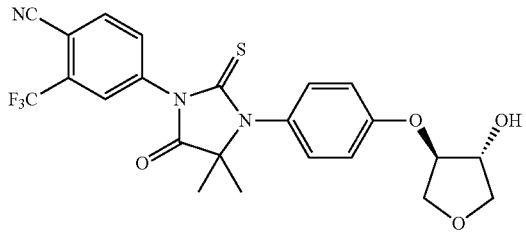

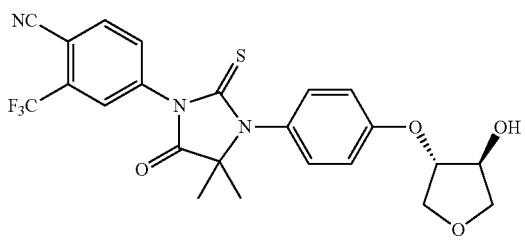

14

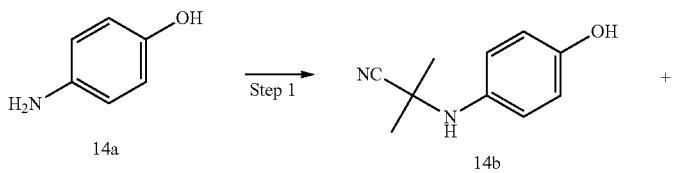

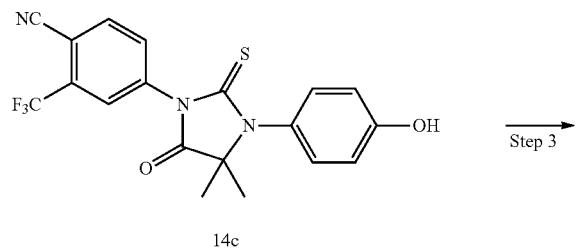

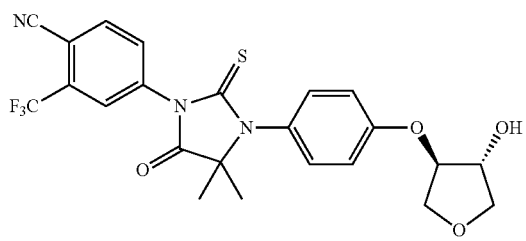

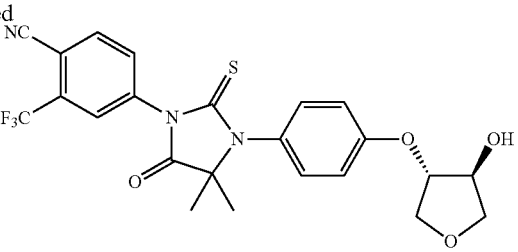

14

Step 1

2-((4-Hydroxyphenyl)amino)-2-methylpropanenitrile

4-Aminophenol 14a (4 g, 36.65 mmol) was dissolved in 72 mL of a mixture of acetone and dichloromethane (v/v=1:2), followed by addition of trimethylsilyl cyanide (7.4 mL, 55.05 mmol) and trifluoromethanesulfonic acid trimethylsilyl ester (0.3 mL, 1.84 mmol). The reaction solution was stirred for 12 hours. The resulting solution was concentrated under reduced pressure. The residue was purified by silica gel column chromatography with elution system B to obtain the title compound 2-((4-hydroxyphenyl)amino)-2-methylpropanenitrile 14b (1.50 g, yield 23.2%) as a white solid.

Step 2

4-(3-(4-Hydroxyphenyl)-4,4-dimethyl-5-oxo-2-thioxoimidazolidin-1-yl)-2-(trifluoromethyl)benzonitrile 2-((4-Hydroxyphenyl)amino)-2-methylpropanenitrile 14b (1.50 g, 8.51 mmol) and 4-isothiocyanato-2-(trifluoromethyl)benzonitrile 1d (2.90 g, 12.75 mmol) were dissolved in 5 mL N,N-dimethylacetamide. The reaction solution was warmed up to 60° C. After reacting for 1.5 hours, the reaction solution was mixed with 20 mL of methanol and 20 mL of concentrated hydrochloric acid, cooled down to room temperature, and extracted with ethyl acetate (50 mL). The organic phases were combined, washed with saturated sodium chloride solution (20 mL×3), dried over anhydrous sodium sulfate, and filtered. The filtrate was concentrated under reduced pressure, and the residue was purified by silica gel column chromatography with elution system B to obtain the title compound 4-(3-(4-hydroxyphenyl)-4,4-dimethyl-5-oxo-2-thioxoimidazolidin-1-yl)-2-(trifluoromethyl)benzonitrile 14c (3.20 g, yield 92.9%) as a pale yellow solid.

MS m/z (ESI): 406.2 [M+1]

Step 3

4-(3-(4-((4-Hydroxytetrahydrofuran-3-yl)oxy)phenyl)-4,4-dimethyl-5-oxo-2-thioxoimidazolidin-1-yl)-2-(trifluoromethyl)benzonitrile 4-(3-(4-Hydroxyphenyl)-4,4-dimethyl-5-oxo-2-thioxoimidazolidin-1-yl)-2-(trifluoromethyl)benzonitrile 14c (2.38 g, 5.87 mmol) was placed in a reaction flask, followed by addition of cesium carbonate (2.86 g, 8.81 mmol), 20 mL of N,N-dimethylacetamide and 3,4-epoxy-tetrahydrofuran (0.61 g, 7.05 mmol), successively. The reaction solution was warmed up to 120° C. After reacting for 0.5 hour, the reaction solution was mixed with 100 mL of water and extracted with ethyl acetate (100 mL). The organic phases were combined, washed with water (30 mL×3) and saturated sodium chloride solution (30 mL×3), dried over anhydrous sodium sulfate, and filtered. The filtrate was concentrated under reduced pressure, and the residue was purified by silica gel column chromatography with elution system B to obtain the crude compound. The crude compound was separated by HPLC to obtain the title product 4-(3-(4-(((3R,4R/3S,4S)-4-hydroxytetrahydrofuran-3-yl)oxy)phenyl)-4,4-dimethyl-5-oxo-2-thioxoimidazolidin-1-yl)-2-(trifluoromethyl)benzonitrile 14 (350 mg, yield 12.1%) as a white solid.

MS m/z (ESI): 492.3 [M+1]; $^1$H NMR (400 MHz, CDCl$_3$): δ 8.03-8.01 (m, 2H), 7.90-7.88 (m, 1H), 7.28-7.26 (m, 2H), 7.12-7.10 (m, 2H), 4.81-4.80 (m, 1H), 4.53-4.52 (m, 1H), 4.37-4.33 (m, 1H), 4.14-4.10 (m, 1H), 4.02-3.99 (m, 1H), 3.91-3.89 (m, 1H), 1.62 (s, 6H).

Examples 15, 16

4-(3-(4-(((3R,4R)-4-Hydroxytetrahydrofuran-3-yl)oxy)phenyl)-4,4-dimethyl-5-oxo-2-thioxoimidazolidin-1-yl)-2-(trifluoromethyl)benzonitrile

4-(3-(4-(((3S,4S)-4-Hydroxytetrahydrofuran-3-yl)oxy)phenyl)-4,4-dimethyl-5-oxo-2-thioxoimidazolidin-1-yl)-2-(trifluoromethyl)benzonitrile

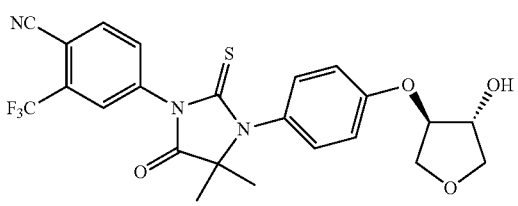

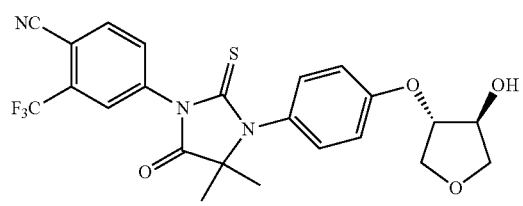

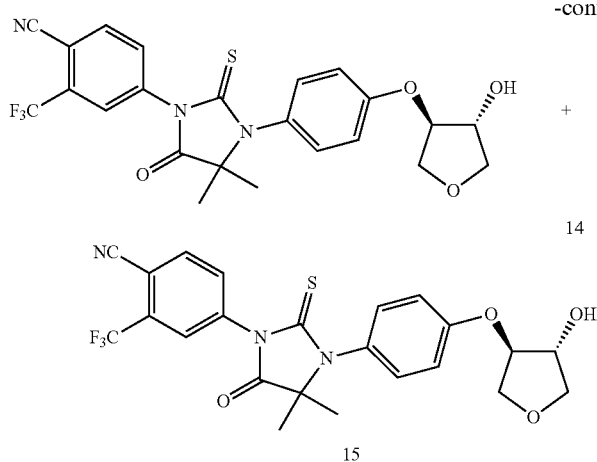

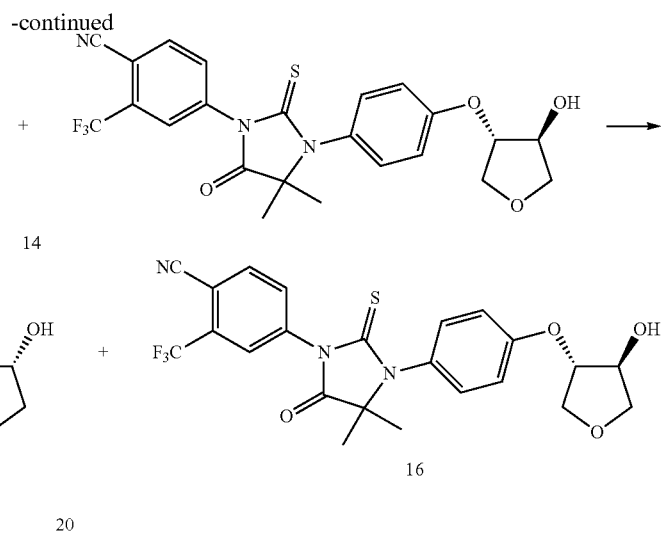

4-(3-(4-(((3R,4R/3S,4S)-4-Hydroxytetrahydrofuran-3-yl) oxy)phenyl)-4,4-dimethyl-5-oxo-2-thioxoimidazolidin-1-yl)-2-(trifluoromethyl)benzonitrile 14 (350 mg, 0.71 mmol) was chirally separated by preparation equipments and a chiral column by HPLC (separation condition: chiral column CHIRALCEL IA, mobile phase: n-hexane:ethanol:dichloromethane=80:10:10, flow rate: 20 mL/minute). The corresponding fractions were collected, and evaporated to remove the solvent to obtain the title product 4-(3-(4-(((3R,4R)-4-hydroxytetrahydrofuran-3-yl)oxy)phenyl)-4,4-dimethyl-5-oxo-2-thioxoimidazolidin-1-yl)-2-(trifluoromethyl)benzonitrile 15 (150 mg, 0.31 mmol) and 4-(3-(4-(((3S,4S)-4-hydroxytetrahydrofuran-3-yl)oxy)phenyl)-4,4-dimethyl-5-oxo-2-thioxoimidazolidin-1-yl)-2-(trifluoromethyl) benzonitrile 16 (150 mg, 0.31 mmol).

15: MS m/z (ESI): 492.3 [M+1], retention time=6.136 minutes, ee value>99.0%.

16: MS m/z (ESI): 492.3 [M+1], retention time=7.139 minutes, ee value>99.0%.

15: $^1$H NMR (400 MHz, CDCl$_3$): δ 8.03-8.01 (m, 2H), 7.90-7.88 (m, 1H), 7.28-7.26 (m, 2H), 7.12-7.10 (m, 2H), 4.81-4.80 (m, 1H), 4.53-4.52 (m, 1H), 4.37-4.33 (m, 1H), 4.14-4.10 (m, 1H), 4.02-3.99 (m, 1H), 3.91-3.89 (m, 1H), 1.62 (s, 6H).

16: $^1$H NMR (400 MHz, CDCl$_3$): δ 8.03-8.01 (m, 2H), 7.90-7.88 (m, 1H), 7.28-7.26 (m, 2H), 7.12-7.10 (m, 2H), 4.81-4.80 (m, 1H), 4.53-4.52 (m, 1H), 4.37-4.33 (m, 1H), 4.14-4.10 (m, 1H), 4.02-3.99 (m, 1H), 3.91-3.89 (m, 1H), 1.62 (s, 6H).

Example 17

4-(3-(4-(2-Hydroxyethoxy)phenyl)-4,4-dimethyl-5-oxo-2-thioxoimidazolidin-1-yl)-2-(trifluoromethyl) benzonitrile

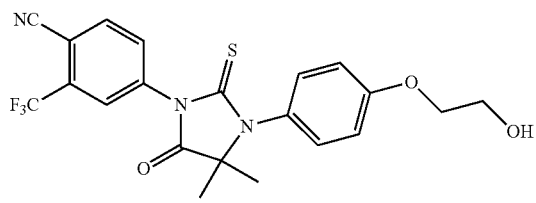

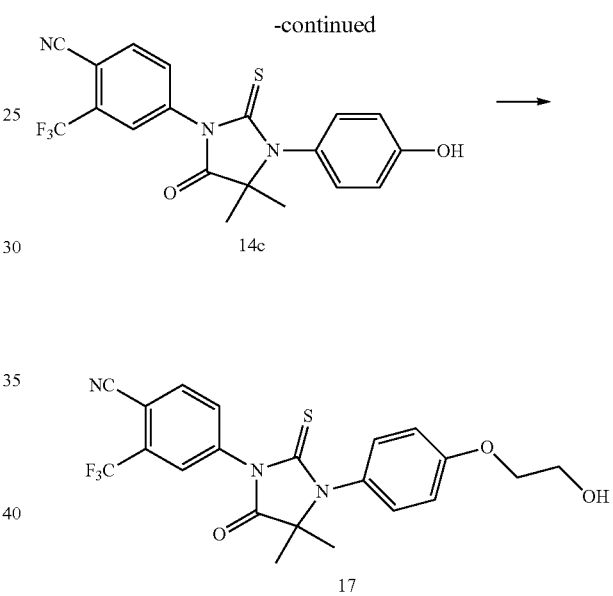

4-(3-(4-Hydroxyphenyl)-4,4-dimethyl-5-oxo-2-thioxoimidazolidin-1-yl)-2-(trifluoromethyl)benzonitrile 14c (100 mg, 0.25 mmol) was placed in a reaction flask, followed by addition of potassium carbonate (69 mg, 0.50 mmol), 2 mL of N,N-dimethylformamide, and bromoethanol (62 mg, 0.50 mmol), successively. The reaction solution was warmed up to 80° C. After reacting for 12 hours, the reaction solution was cooled down to room temperature, mixed with 20 mL of water, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure and the residue was purified by thin layer chromatography with elution system B to obtain the title compound 4-(3-(4-(2-hydroxyethoxy)phenyl)-4,4-dimethyl-5-oxo-2-thioxoimidazolidin-1-yl)-2-(trifluoromethyl)benzonitrile 17 (40 mg, yield 36.3%) as a white solid.

MS m/z (ESI): 450.3 [M+1]; $^1$H NMR (400 MHz, CDCl$_3$): δ 7.99-7.97 (m, 2H), 7.86-7.84 (m, 1H), 7.24-7.21 (m, 2H), 7.09-7.06 (m, 2H), 4.16-4.14 (m, 2H), 4.02-4.00 (m, 2H), 1.58 (s, 6H).

Example 18

4-(3-(3-Fluoro-4-((tetrahydrofuran-3-yl)methoxy)phenyl)-4,4-dimethyl-5-oxo-2-thioxoimidazolidin-1-yl)-2-(trifluoromethyl)benzonitrile

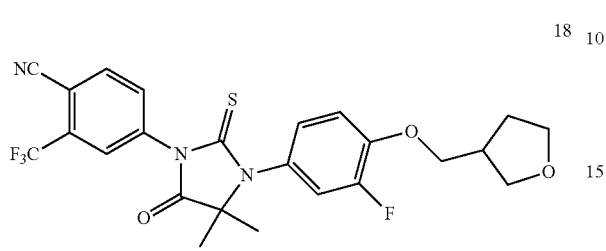

18

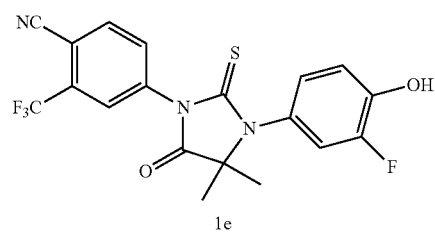

1e +

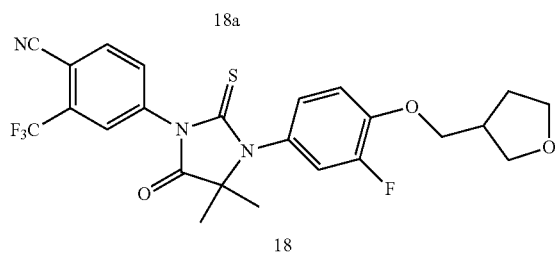

18a

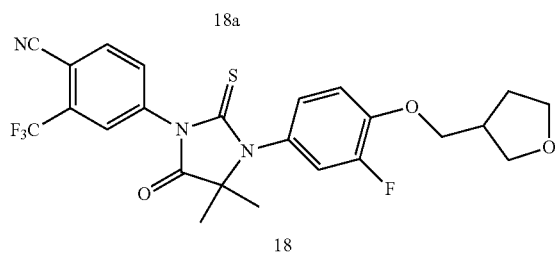

18

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of (tetrahydrofuran-3-yl)methanol 18a (29 mg, 0.28 mmol), 1,1'-(azodicarbonyl)dipiperidine (95 mg, 0.38 mmol), 5 mL of methylbenzene, and tri-n-butylphosphine (76 mg, 0.38 mmol), successively. The reaction solution was warmed up to 50° C. and stirred for 2 hours. The reaction solution was dissolved in a small amount of methanol, and purified by thin layer chromatography with elution system A to obtain the title compound 4-(3-(3-fluoro-4-((tetrahydrofuran-3-yl)methoxy)phenyl)-4,4-dimethyl-5-oxo-2-thioxoimidazolidin-1-yl)-2-(trifluoromethyl)benzonitrile 18 (97 mg, yield 81.5%) as a white solid.

MS m/z (ESI): 508.4 [M+1]; $^1$H NMR (400 MHz, CDCl$_3$): δ 8.00-7.96 (m, 2H), 7.85-7.83 (m, 1H), 7.11-7.03 (m, 3H), 4.07-3.99 (m, 2H), 3.96-3.91 (m, 2H), 3.84-3.75 (m, 2H), 2.88-2.80 (m, 1H), 2.22-2.14 (m, 1H), 1.80-1.75 (m, 1H), 1.59 (s, 6H).

Example 19

4-(3-(3-Fluoro-4-((piperidin-4-yl)oxy)phenyl)-4,4-dimethyl-5-oxo-2-thioxoimidazolidin-1-yl)-2-(trifluoromethyl)benzonitrile

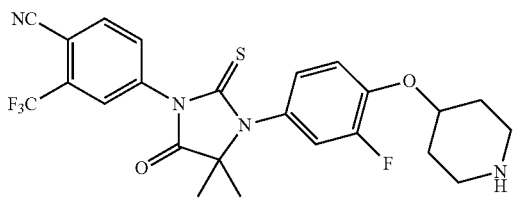

19

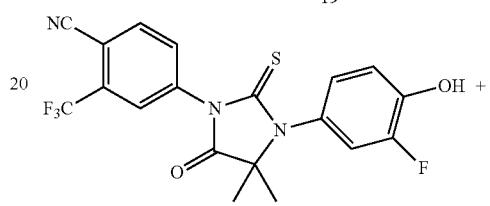

1e

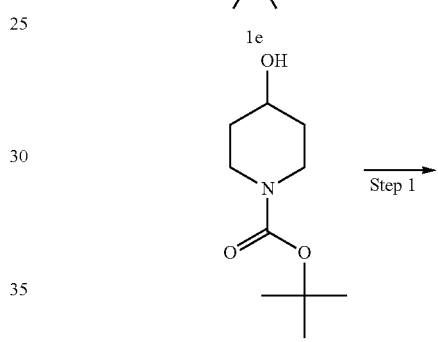

19a

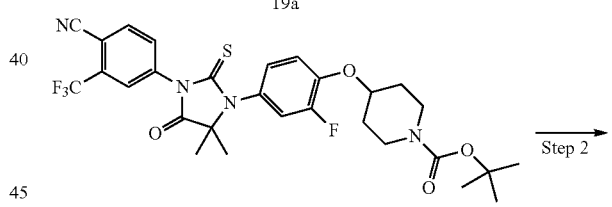

19b

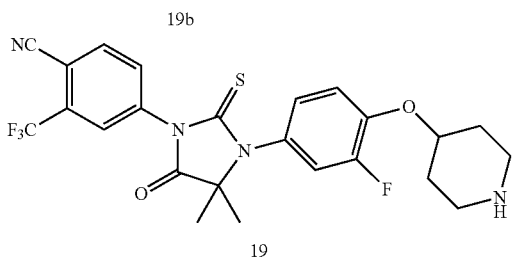

19

Step 1 tert-Butyl 4-(4-(3-(4-cyano-3-(trifluoromethyl)phenyl)-5,5-dimethyl-4-oxo-2-thioxoimidazolidin-1-yl)-2-fluorophenoxy)piperidine-1-carboxylate 4-(3-(3-Fluoro-4-hydroxyphenyl)-4,4-dimethyl-5-oxo-2-thioxoimidazolidin-1-yl)-2-(trifluoromethyl)benzonitrile 1e (200 mg, 0.47 mmol) was placed in a reaction flask, followed by addition of tert-butyl 4-hydroxypiperidine-1-carboxylate 19a (114 mg, 0.57 mmol), 1,1'-(azodicarbonyl) dipiperidine (191 mg, 0.76 mmol), 10 mL of methylbenzene, and tri-n-butylphosphine (153 mg, 0.76 mmol), successively. The reaction solution was warmed up to 50° C. and stirred for 3 hours. The reaction solution was concentrated under reduced pressure, and the resulting residue was purified by silica gel column chromatography with elution system B to obtain the title compound tert-butyl 4-(4-(3-(4-cyano-3-(trifluoromethyl)phenyl)-5,5-dimethyl-4-oxo-2-thioxoimidazolidin-1-yl)-2-fluorophenoxy)piperidine-1-carboxylate 19b (200 mg, yield 69.8%) as a white solid.

MS m/z (ESI): 551.4 [M−56+1]

Step 2

4-(3-(3-Fluoro-4-((piperidin-4-yl)oxy)phenyl)-4,4-dimethyl-5-oxo-2-thioxoimidazolidin-1-yl)-2-(trifluoromethyl)benzonitrile tert-Butyl 4-(4-(3-(4-cyano-3-(trifluoromethyl)phenyl)-5,5-dimethyl-4-oxo-2-thioxoimidazolidin-1-yl)-2-fluorophenoxy)piperidine-1-carboxylate 19b (180 mg, 0.30 mmol) was dissolved in 6 mL of a solution of 2 M hydrogen chloride in methanol. The reaction solution was stirred for 12 hours. The reaction solution was concentrated under reduced pressure to obtain the title product 4-(3-(3-fluoro-4-((piperidin-4-yl)oxy)phenyl)-4,4-dimethyl-5-oxo-2-thioxoimidazolidin-1-yl)-2-(trifluoromethyl)benzonitrile 19 (160 mg, yield 99.4%) as a white solid.

MS m/z (ESI): 507.4 [M+1]; $^1$H NMR (400 MHz, CDCl$_3$): δ 7.95-7.99 (m, 2H), 7.84 (d, 1H), 7.07-7.11 (m, 3H), 4.56-4.57 (m, 1H), 2.99-3.02 (m, 2H), 2.85-2.88 (m, 2H), 2.35-2.37 (m, 2H), 2.05-2.09 (m, 2H), 1.59 (s, 6H).

Example 20

4-(3-(3-Fluoro-4-((1-methylpiperidin-4-yl)oxy)phenyl)-4,4-dimethyl-5-oxo-2-thioxoimidazolidin-1-yl)-2-(trifluoromethyl)benzonitrile

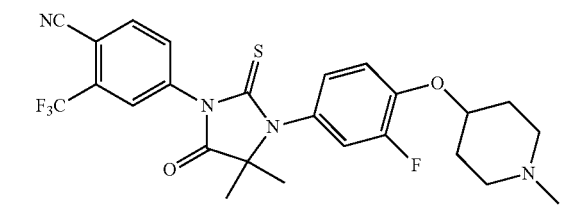

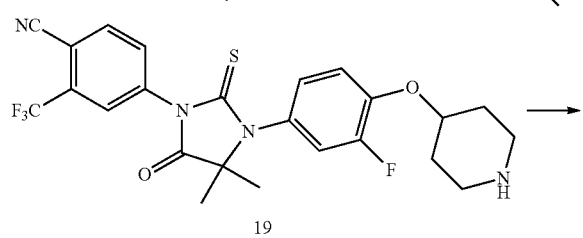

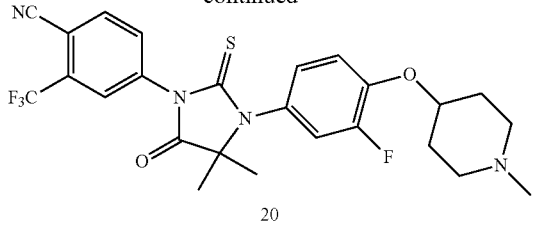

4-(3-(3-Fluoro-4-((piperidin-4-yl)oxy)phenyl)-4,4-dimethyl-5-oxo-2-thioxoimidazolidin-1-yl)-2-(trifluoromethyl)benzonitrile 19 (150 mg, 0.28 mmol) was dissolved in 1.5 mL of methanol, followed by addition of 1 mL of 40% formaldehyde solution and 1 mL of 0.3 M sodium cyanoborohydride in a saturated methanol solution of zinc chloride, successively. The reaction solution was stirred for 3 hours, then mixed with 15 mL of water, and extracted with ethyl acetate (15 mL×3). The organic phases were combined, washed with saturated sodium chloride solution (20 mL), dried over anhydrous sodium sulfate, and filtered. The filtrate was concentrated under reduced pressure, and the residue was purified by thin layer chromatography with elution system A to obtain the title compound 4-(3-(3-fluoro-4-((1-methylpiperidin-4-yl)oxy)phenyl)-4,4-dimethyl-5-oxo-2-thioxoimidazolidin-1-yl)-2-(trifluoromethyl)benzonitrile 20 (90 mg, yield 62.6%) as a white solid.

MS m/z (ESI): 521.2 [M+1]; $^1$H NMR (400 MHz, CDCl$_3$): δ 7.95-7.99 (m, 2H), 7.84 (d, 1H), 7.07-7.11 (m, 3H), 4.56-4.57 (m, 1H), 2.97-2.99 (m, 2H), 2.81-2.85 (m, 2H), 2.56 (s, 3H), 2.34-2.36 (m, 2H), 2.05-2.09 (m, 2H), 1.59 (s, 6H).

Example 21

(R)-4-(4,4-Dimethyl-5-oxo-3-(6-((tetrahydrofuran-3-yl)oxy)pyridin-3-yl)-2-thioxoimidazolidin-1-yl)-2-(trifluoromethyl)benzonitrile

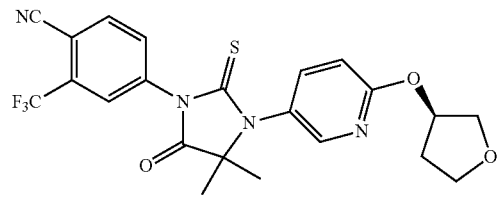

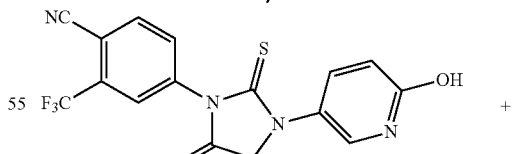

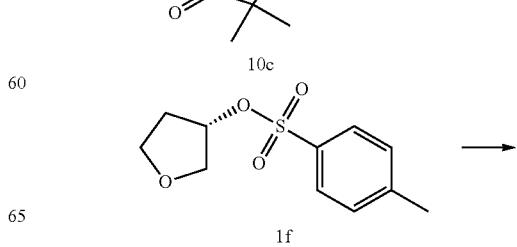

-continued

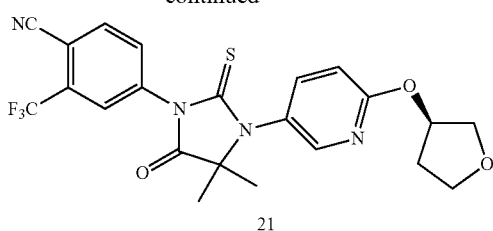

21

4-(3-(6-Hydroxypyridin-3-yl)-4,4-dimethyl-5-oxo-2-thioxoimidazolidin-1-yl)-2-(trifluoromethyl)benzonitrile 10c (100 mg, 0.24 mmol) was placed in a reaction flask, followed by addition of (S)-tetrahydrofuran-3-yl-4-methyl-benzenesulfonate 1f (116 mg, 0.48 mmol), cesium carbonate (235 mg, 0.72 mmol), and 3 mL of N,N-dimethylacetamide, successively. The reaction solution was warmed up to 60° C. and stirred for 2 hours. The reaction solution was cooled down to room temperature, mixed with 5 mL of saturated sodium chloride solution, and extracted with ethyl acetate (10 mL×3). The organic phases were combined, dried over anhydrous sodium sulfate, and filtered. The filtrate was concentrated under reduced pressure, and the residue was purified by thin layer chromatography with elution system A to obtain the title compound (R)-4-(4,4-dimethyl-5-oxo-3-(6-((tetrahydrofuran-3-yl)oxy)pyridin-3-yl)-2-thioxoimidazolidin-1-yl)-2-(trifluoromethyl)benzonitrile 21 (46 mg, yield 40.3%) as a yellow solid.

MS m/z (ESI): 477.1 [M+1]; $^1$H NMR (400 MHz, CDCl$_3$): δ 8.09-8.08 (m, 1H), 8.01-7.97 (m, 2H), 7.86-7.84 (m, 1H), 7.54-7.51 (m, 1H), 6.92-6.90 (m, 1H), 5.76-5.60 (m, 1H), 4.09-3.93 (m, 4H), 2.32-2.21 (m, 2H), 1.61 (s, 6H).

Example 22

4-(3-(3-Fluoro-4-(3-(methylsulfonyl)propoxy)phenyl)-4,4-dimethyl-5-oxo-2-thioxoimidazolidin-1-yl)-2-(trifluoromethyl)benzonitrile

22

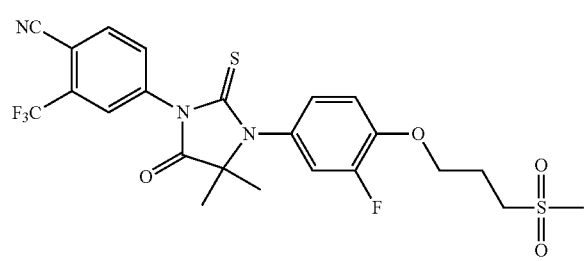

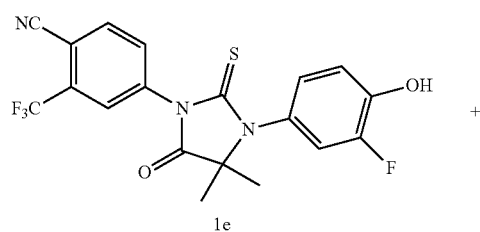

1e

-continued

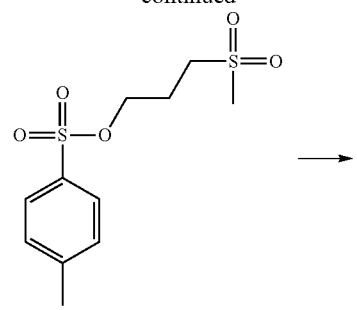

22a

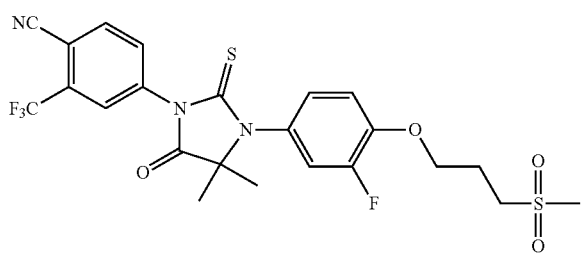

22

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of 3-(methylsulfonyl)propyl-4-methyl-benzenesulfonate 22a (138 mg, 0.47 mmol, prepared by a method disclosed in PCT Patent Application Publication WO 2008/1931 A2), cesium carbonate (231 mg, 0.71 mmol), and 2 mL of N,N-dimethylacetamide, successively. The reaction solution was warmed up to 70° C. and stirred for 2 hours. The reaction solution was cooled down to room temperature, mixed with 15 mL of water and extracted with ethyl acetate (15 mL×3). The organic phases were combined, washed with saturated sodium chloride solution (20 mL×2), dried over anhydrous sodium sulfate, and filtered. The filtrate was concentrated under reduced pressure and the residue was purified by thin layer chromatography with elution system B, and subsequently with elution system A to obtain the title compound 4-(3-(3-fluoro-4-(3-(methylsulfonyl)propoxy)phenyl)-4,4-dimethyl-5-oxo-2-thioxoimidazolidin-1-yl)-2-(trifluoromethyl)benzonitrile 22 (50 mg, yield 63.8%) as a white solid.

MS m/z (ESI): 544.2 [M+1]; $^1$H NMR (400 MHz, CDCl$_3$): δ 7.95-8.00 (m, 2H), 7.84 (d, 1H), 7.05-7.10 (m, 3H), 4.26-4.29 (m, 2H), 3.29-3.32 (m, 2H), 2.99 (s, 3H), 2.41-2.46 (m, 2H), 1.59 (s, 6H).

Example 23

4-(3-(4-((1,1-Dioxidotetrahydro-2H-thiopyran-4-yl)oxy)-3-fluorophenyl)-4,4-dimethyl-5-oxo-2-thioxoimidazolidin-1-yl)-2-(trifluoromethyl)benzonitrile

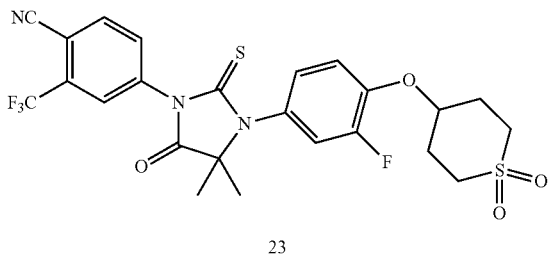

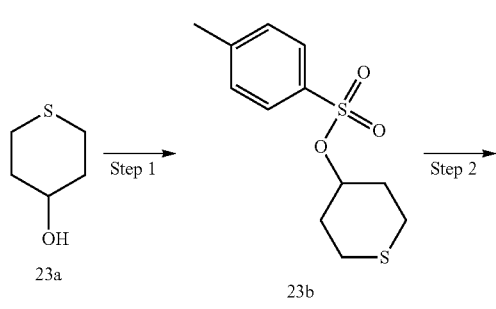

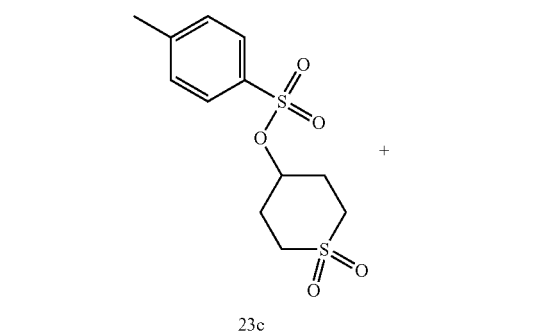

Step 1

Tetrahydro-2H-thiopyran-4-yl-4-methylbenzenesulfonate

Tetrahydro-2H-thiopyran-4-ol 23a (350 mg, 2.97 mmol, prepared by a method disclosed in EP Patent Application Publication EP1466898 A1) was placed in a reaction flask, followed by addition of triethylamine (606 mg, 5.94 mmol), 4-dimethylaminopyridine (36 mg, 0.30 mmol), 20 mL of dichloromethane, and p-toluenesulfonyl chloride (848 mg, 4.45 mmol). After reacting for 12 hours, the reaction solution was mixed with 30 mL of water, and left to stand and separate. The aqueous phase was then extracted with dichloromethane (10 mL×2). The organic phases were combined, washed with saturated sodium chloride solution (30 mL), dried over anhydrous sodium sulfate, and filtered. The filtrate was concentrated under reduced pressure, and the residue was purified by silica gel column chromatography with elution system B to obtain the title compound tetrahydro-2H-thiopyran-4-yl-4-methylbenzenesulfonate 23b (556 mg, yield 68.9%) as a white solid.

Step 2

1,1-Dioxidotetrahydro-2H-thiopyran-4-yl 4-methylbenzenesulfonate

Tetrahydro-2H-thiopyran-4-yl-4-methylbenzenesulfonate 23b (280 mg, 1.03 mmol) was dissolved in 6 mL of a mixture of dichloromethane and methanol (v/v=1:1), followed by addition of 0.6 mL of water and Oxone® reagent (1.58 g, 2.57 mmol) successively. The reaction solution was stirred for 3 hours, concentrated under reduced pressure, and mixed with 20 mL of water and 20 mL of ethyl acetate. The reaction mixture was left to stand and separate, The aqueous phase was then extracted with ethyl acetate (10 mL×2). The organic phases were combined, washed with saturated sodium sulfate solution (10 mL×2) and saturated sodium chloride solution (20 mL), dried over anhydrous sodium sulfate, and filtered. The filtrate was concentrated under reduced pressure to obtain the title compound 1,1-dioxidotetrahydro-2H-thiopyran-4-yl 4-methylbenzenesulfonate 23c (279 mg, yield 89.1%) as a white solid.

Step 3

4-(3-(4-((1,1-Dioxidotetrahydro-2H-thiopyran-4-yl)oxy)-3-fluorophenyl)-4,4-dimethyl-5-oxo-2-thioxoimidazolidin-1-yl)-2-(trifluoromethyl)benzonitrile 4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of 1,1-dioxidotetrahydro-2H-thiopyran-4-yl 4-methylbenzenesulfonate 23c (144 mg, 0.47 mmol), cesium carbonate (231 mg, 0.71 mmol), and 1 mL of N,N-dimethylacetamide, successively. The reaction mixture was warmed up to 70° C. After reacting for 3 hours, the reaction solution was cooled down to room temperature, mixed with 15 mL of H$_2$O, and extracted with ethyl acetate (15 mL×3). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system B, and subsequently with elution system A to obtain the title compound 4-(3-(4-((1,1-dioxidotetrahydro-2H-thiopyran-4-yl)oxy)-3-fluorophenyl)-4,4-dimethyl-5-oxo-2-thioxoimidazolidin-1-yl)-2-(trifluoromethyl)benzonitrile 23 (70 mg, yield 72.4%) as a white solid.

MS m/z (ESI): 556.2 [M+1]; $^1$H NMR (400 MHz, CDCl$_3$): δ 7.95-8.00 (m, 2H), 7.83 (d, 1H), 7.06-7.12 (m, 3H), 4.70-4.71 (m, 1H), 3.45-3.49 (m, 2H), 2.99-3.02 (m, 2H), 2.42-2.50 (m, 4H), 1.60 (s, 6H).

Example 24

(S)-4-(4,4-Dimethyl-5-oxo-3-(6-((tetrahydrofuran-3-yl)oxy)pyridin-3-yl)-2-thioxoimidazolidin-1-yl)-2-(trifluoromethyl)benzonitrile zolidin-1-yl)-2-(trifluoromethyl)benzonitrile 24 (60 mg, yield 52.6%) as a white solid.

MS m/z (ESI): 477.2 [M+1]; $^1$H NMR (400 MHz, CDCl$_3$): δ 8.09-8.08 (m, 1H), 8.00-7.96 (m, 2H), 7.86-7.84 (m, 1H), 7.54-7.51 (m, 1H), 6.92-6.90 (m, 1H), 5.63-5.60 (m, 1H), 4.14-3.91 (m, 4H), 2.35-2.16 (m, 2H), 1.60 (s, 6H).

Example 25

4-(4,4-Dimethyl-5-oxo-3-(6-((tetrahydrofuran-3-yl)methoxy)pyridin-3-yl)-2-thioxoimidazolidin-1-yl)-2-(trifluoromethyl)benzonitrile

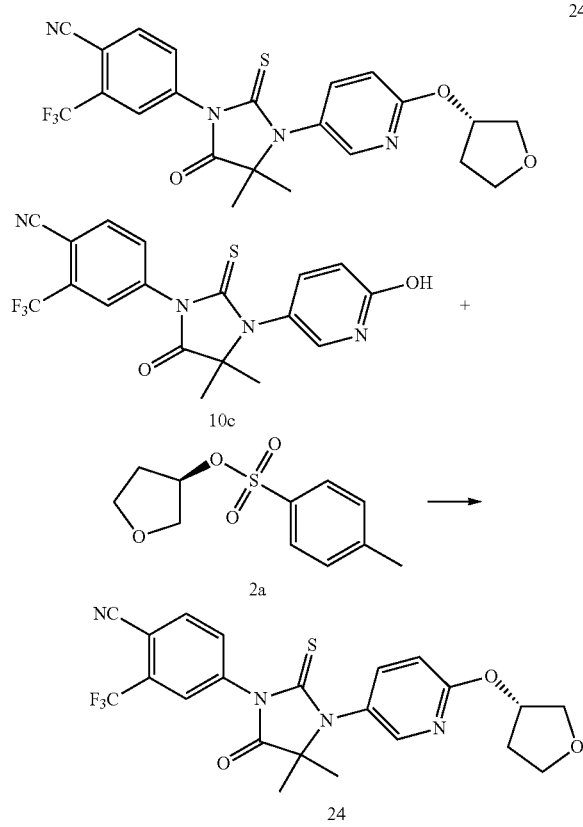

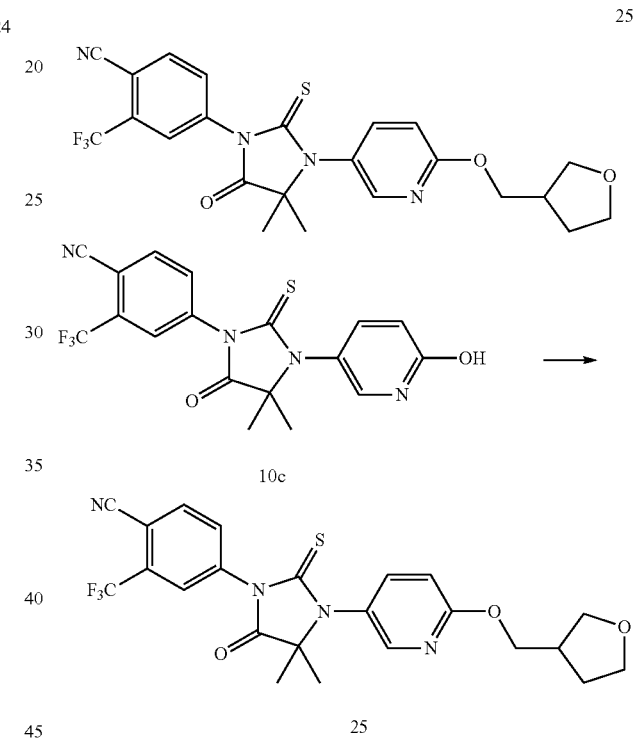

4-(3-(6-Hydroxypyridin-3-yl)-4,4-dimethyl-5-oxo-2-thioxoimidazolidin-1-yl)-2-(trifluoromethyl)benzonitrile 10c (100 mg, 0.24 mmol) was placed in a reaction flask, followed by addition of (R)-tetrahydrofuran-3-yl-4-methylbenzenesulfonate 2a (116 mg, 0.48 mmol), cesium carbonate (235 mg, 0.72 mmol), and 3 mL of N,N-dimethylacetamide, successively. The reaction solution was warmed up to 60° C. and stirred for 2 hours. The reaction solution was cooled down to room temperature, mixed with 10 mL of saturated sodium chloride solution, and extracted with ethyl acetate (20 mL×3). The organic phases were combined, dried over anhydrous sodium sulfate, and filtered. The filtrate was concentrated under reduced pressure, and the residue was purified by thin layer chromatography with elution system A to obtain the title compound (S)-4-(4,4-dimethyl-5-oxo-3-(6-(((tetrahydrofuran-3-yl)oxy)pyridin-3-yl)-2-thioxoimida- 4-(3-(6-Hydroxypyridin-3-yl)-4,4-dimethyl-5-oxo-2-thioxoimidazolidin-1-yl)-2-(trifluoromethyl)benzonitrile 10c (80 mg, 0.20 mmol) was placed in a reaction flask, followed by addition of (tetrahydrofuran-3-yl)methanol 18a (24 mg, 0.24 mmol), 1,1'-(azodicarbonyl)dipiperidine (80 mg, 0.32 mmol), 5 mL of methylbenzene, and tri-n-butylphosphine (64 mg, 0.32 mmol), successively. The reaction solution was warmed up to 50° C. and stirred for 2 hours. The reaction solution was dissolved in a small amount of methanol, and purified by thin layer chromatography with elution system A to obtain the title compound 4-(4,4-dimethyl-5-oxo-3-(6-((tetrahydrofuran-3-yl) methoxy)pyridin-3-yl)-2-thioxoimidazolidin-1-yl)-2-(trifluoromethyl)benzonitrile 25 (40 mg, yield 41.4%) as a yellow solid.

MS m/z (ESI): 491.2 [M+1]; $^1$H NMR (400 MHz, CDCl$_3$): δ 8.10-8.09 (m, 1H), 8.00-7.97 (m, 2H), 7.86-7.84 (m, 1H), 7.54-7.51 (m, 1H), 6.92-6.90 (m, 1H), 4.38-4.25 (m, 2H), 3.96-3.90 (m, 2H), 3.84-3.70 (m, 2H), 2.80-2.77 (m, 1H), 2.25-2.11 (m, 2H), 1.60 (s, 6H).

Example 26

2-(4-(3-(4-Cyano-3-(trifluoromethyl)phenyl)-5,5-dimethyl-4-oxo-2-thioxoimidazolidin-1-yl)-2-fluorophenoxy)-N-methylbenzamide

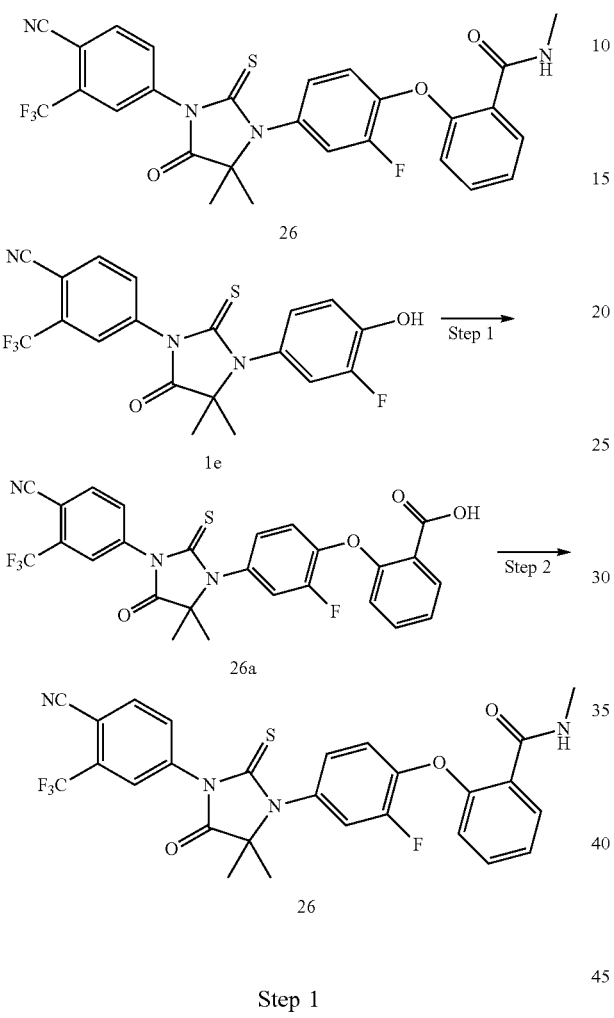

Step 1

2-(4-(3-(4-Cyano-3-(trifluoromethyl)phenyl)-5,5-dimethyl-4-oxo-2-thioxoimidazolidin-1-yl)-2-fluorophenoxy)benzoic acid 4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of 2-iodo benzoic acid (70 mg, 0.28 mmol), cuprous iodide (14 mg, 0.07 mmol), phenanthroline (13 mg, 0.07 mmol), cesium carbonate (186 mg, 0.57 mmol), and 4 mL of methylbenzene. successively. The reaction solution was warmed up to 120° C. and stirred for 12 hours. The reaction solution was cooled down to room temperature, and 2 M hydrochloric acid was added to adjust the pH to 2, followed by addition of H₂O (20 mL), and extraction with ethyl acetate (15 mL×3). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system A to obtain the title compound 2-(4-(3-(4-cyano-3-(trifluoromethyl)phenyl)-5,5-dimethyl-4-oxo-2-thioxoimidazolidin-1-yl)-2-fluorophenoxy)benzoic acid 26a (32 mg, yield 24.9%) as a yellow solid.

MS m/z (ESI): 544.2 [M+1]

Step 2

2-(4-(3-(4-Cyano-3-(trifluoromethyl)phenyl)-5,5-dimethyl-4-oxo-2-thioxoimidazolidin-1-yl)-2-fluorophenoxy)-N-methylbenzamide 2-(4-(3-(4-Cyano-3-(trifluoromethyl)phenyl)-5,5-dimethyl-4-oxo-2-thioxoimidazolidin-1-yl)-2-fluorophenoxy)benzoic acid 26a (30 mg, 0.06 mmol) was placed in a reaction flask, followed by addition of a solution of 2 M methylamine in tetrahydrofuran (33 μL, 0.07 mmol), 2-(7-azabenzotriazol-1-yl)-N,N,N',N'-tetramethyluronium hexafluorophosphate) (25 mg, 0.07 mmol), triethylamine (23 μL, 0.17 mmol), and 2 mL of dichloromethane, successively. The reaction mixture was stirred for 48 hours. The reaction solution was concentrated under reduced pressure, and the residue was purified by thin layer chromatography with elution system A to obtain the title compound 2-(4-(3-(4-cyano-3-(trifluoromethyl)phenyl)-5,5-dimethyl-4-oxo-2-thioxoimidazolidin-1-yl)-2-fluorophenoxy)-N-methylbenzamide 26 (32 mg, yield 32.7%) as a white solid.

MS m/z (ESI): 557.2 [M+1]; ¹H NMR (400 MHz, CDCl₃): δ 7.96-8.01 (m, 2H), 7.84 (d, 1H), 7.32-7.41 (m, 4H), 7.06-7.12 (m, 3H), 6.56-6.57 (m, 1H), 2.99 (d, 3H), 1.60 (s, 6H).

Example 27

(S)-4-(3-(3-Fluoro-4-((1-methylpyrrolidin-3-yl)oxy)phenyl)-4,4-dimethyl-5-oxo-2-thioxoimidazolidin-1-yl)-2-(trifluoromethyl)benzonitrile

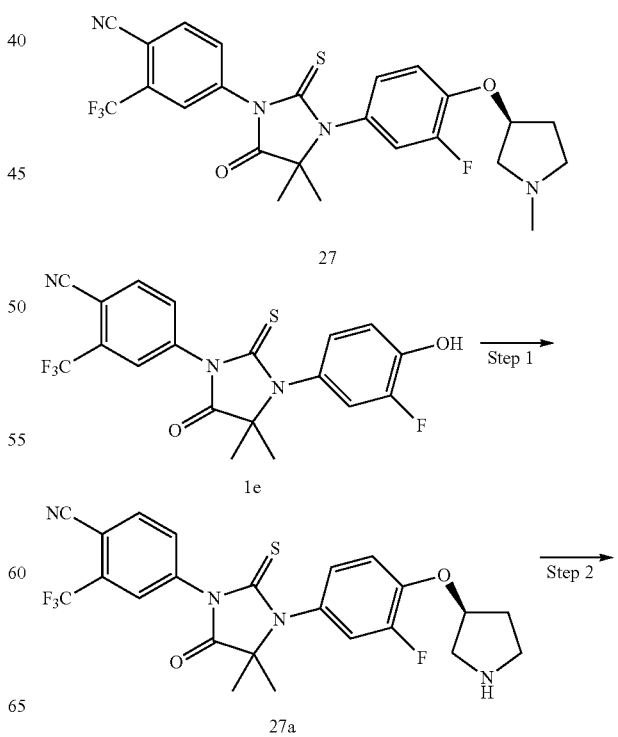

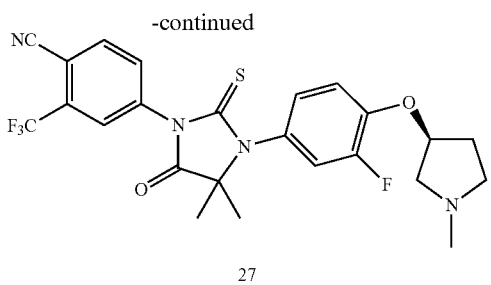

27

Step 1

(S)-4-(3-(3-Fluoro-4-((pyrrolidin-3-yl)oxy)phenyl)-4,4-dimethyl-5-oxo-2-thioxoimidazolidin-1-yl)-2-(trifluoromethyl)benzonitrile 4-(3-(3-Fluoro-4-hydroxyphenyl)-4,4-dimethyl-5-oxo-2-thioxoimidazolidin-1-yl)-2-(trifluoromethyl)benzonitrile 1e (200 mg, 0.47 mmol) was placed in a reaction flask, followed by addition of (R)-pyrrolidin-3-ol (50 mg, 0.58 mmol), 1,1'-(azodicarbonyl)dipiperidine (192 mg, 0.76 mmol), 20 mL of methylbenzene, and tri-n-butylphosphine (154 mg, 0.76 mmol), successively. The reaction solution was warmed up to 50° C. and stirred for 1 hour. The reaction solution was concentrated under reduced pressure, and the residue was purified by silica gel column chromatography with elution system A to obtain the title compound (S)-4-(3-(3-fluoro-4-((pyrrolidin-3-yl)oxy)phenyl)-4,4-dimethyl-5-oxo-2-thioxoimidazolidin-1-yl)-2-(trifluoromethyl)benzonitrile 27a (100 mg, yield 43.1%) as a white solid.

Step 2

(S)-4-(3-(3-Fluoro-4-((1-methylpyrrolidin-3-yl)oxy)phenyl)-4,4-dimethyl-5-oxo-2-thioxoimidazolidin-1-yl)-2-(trifluoromethyl)benzonitrile (S)-4-(3-(3-Fluoro-4-((pyrrolidin-3-yl)oxy)phenyl)-4,4-dimethyl-5-oxo-2-thioxoimidazolidin-1-yl)-2-(trifluoromethyl)benzonitrile 27a (100 mg, 0.20 mmol) was dissolved in 1.5 mL of methanol, followed by addition of 1 mL of 40% formaldehyde solution and 1 mL of 0.3 M sodium cyanoborohydride in a saturated methanol solution of zinc chloride, successively. The reaction solution was stirred for 12 hours, then mixed with 20 mL of water and extracted with ethyl acetate (20 mL×2). The organic phases were combined, washed with saturated sodium chloride solution (20 mL×3), dried over anhydrous sodium sulfate, and filtered. The filtrate was concentrated under reduced pressure, and the residue was purified by thin layer chromatography with elution system A to obtain the title compound (S)-4-(3-(3-fluoro-4-((1-methylpyrrolidin-3-yl)oxy)phenyl)-4,4-dimethyl-5-oxo-2-thioxoimidazolidin-1-yl)-2-(trifluoromethyl)benzonitrile 27 (50 mg, yield 49.0%) as a white solid.

MS m/z (ESI): 507.2 [M+1]; $^1$H NMR (400 MHz, CDCl$_3$): δ 7.99-7.95 (m, 2H), 7.85-7.82 (m, 1H), 7.08-7.00 (m, 3H), 4.97-4.93 (m, 1H), 3.16-3.14 (m, 1H), 2.90-2.84 (m, 2H), 2.76-2.75 (m, 1H), 2.50 (s, 3H), 2.42-2.38 (m, 1H), 2.18-2.16 (m, 1H), 1.59 (s, 6H).

Example 28

4-(3-(3-Fluoro-4-((pyrrolidin-3-yl)oxy)phenyl)-4,4-dimethyl-5-oxo-2-thioxoimidazolidin-1-yl)-2-(trifluoromethyl)benzonitrile

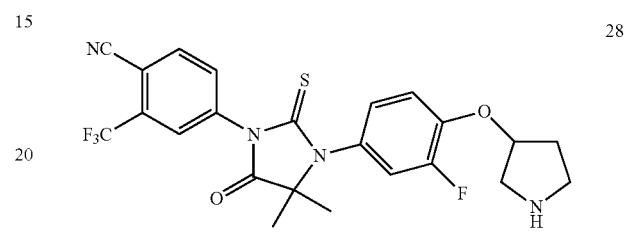

28

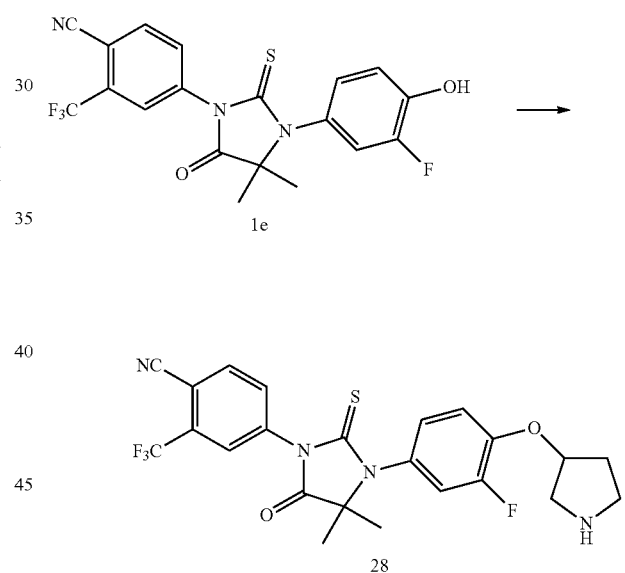

28

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of pyrrolidine-3-ol (12 mg, 0.14 mmol), 1,1'-(azodicarbonyl)dipiperidine (47 mg, 0.19 mmol), 5 mL of methylbenzene, and tri-n-butylphosphine (38 mg, 0.19 mmol), successively. The reaction solution was warmed up to 50° C. and stirred for 1 hour. The reaction solution was concentrated under reduced pressure, and the residue was purified by thin layer chromatography with elution system A to obtain the title compound 4-(3-(3-fluoro-4-((pyrrolidin-3-yl)oxy)phenyl)-4,4-dimethyl-5-oxo-2-thioxoimidazolidin-1-yl)-2-(trifluoromethyl)benzonitrile 28 (45 mg, yield 77.6%) as a white solid.

MS m/z (ESI): 493.2 [M+1]; $^1$H NMR (400 MHz, CDCl$_3$): δ 8.00-7.96 (m, 2H), 7.85-7.82 (m, 1H), 7.17-7.04 (m, 3H), 3.54-3.35 (m, 5H), 2.27-2.18 (m, 2H), 1.60 (s, 6H).

Example 29

4-(3-(3-Fluoro-4-((1-methylpyrrolidin-3-yl)oxy)phenyl)-4,4-dimethyl-5-oxo-2-thioxoimidazolidin-1-yl)-2-(trifluoromethyl)benzonitrile

Example 30

4-(3-(6-(Difluoromethoxy)pyridin-3-yl)-4,4-dimethyl-5-oxo-2-thioxoimidazolidin-1-yl)-2-(trifluoromethyl)benzonitrile

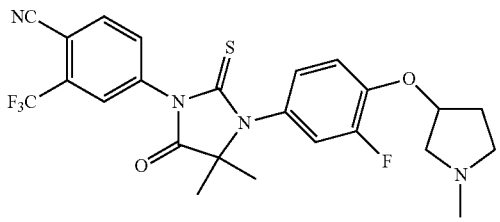

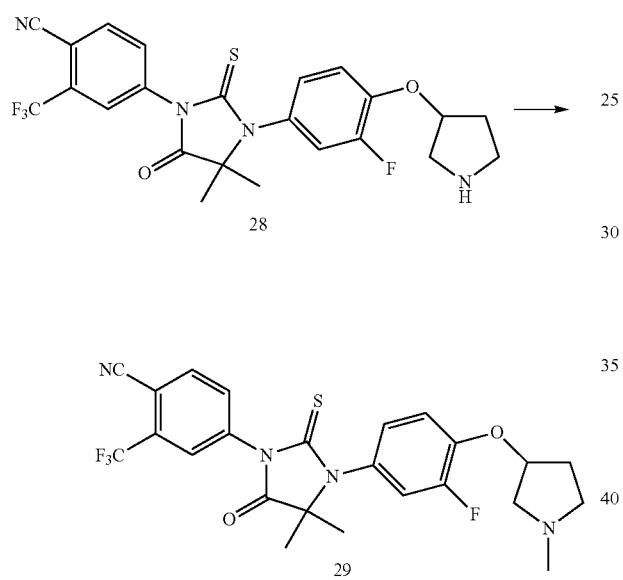

4-(3-(3-Fluoro-4-((pyrrolidin-3-yl)oxy)phenyl)-4,4-dimethyl-5-oxo-2-thioxoimidazolidin-1-yl)-2-(trifluoromethyl)benzonitrile 28 (80 mg, 0.16 mmol) was was dissolved in 1.5 mL of methanol, followed by addition of 1 mL of 40% formaldehyde solution and 1 mL of 0.3 M sodium cyanoborohydride in a saturated methanol solution of zinc chloride, successively. The reaction solution was stirred for 12 hours, then mixed with 50 mL of water and extracted with ethyl acetate (50 mL). The organic phases were washed with water (30 mL×3) and saturated sodium chloride solution (30 mL×3), dried over anhydrous sodium sulfate, and filtered. The filtrate was concentrated under reduced pressure, and the residue was purified by thin layer chromatography with elution system A to obtain the title compound 4-(3-(3-fluoro-4-((1-methylpyrrolidin-3-yl)oxy)phenyl)-4,4-dimethyl-5-oxo-2-thioxoimidazolidin-1-yl)-2-(trifluoromethyl)benzonitrile 29 (50 mg, yield 60.9%) as a white solid.

MS m/z (ESI): 507.2 [M+1]; $^1$H NMR (400 MHz, CDCl$_3$): δ 8.00-7.96 (m, 2H), 7.85-7.83 (m, 1H), 7.09-7.03 (m, 3H), 3.34-3.33 (m, 1H), 2.95-2.93 (m, 3H), 2.59 (s, 3H), 2.44-2.42 (m, 1H), 2.17-2.16 (m, 2H), 1.59 (s, 6H).

4-(3-(6-Hydroxypyridin-3-yl)-4,4-dimethyl-5-oxo-2-thioxoimidazolidin-1-yl)-2-(trifluoromethyl)benzonitrile 10c (50 mg, 0.12 mmol) was dissolved in 2 mL of acetonitrile, followed by addition of anhydrous sodium sulfate (2 mg, 0.01 mmol) and 2-(fluorosulphonyl)difluoroacetic acid (26 mg, 0.15 mmol), successively. The reaction solution was stirred for 12 hours. The reaction solution was then supplemented with 2-(fluorosulphonyl)difluoroacetic acid (26 mg, 0.15 mmol) and a small amount of anhydrous sodium sulfate, warmed up to 60° C. and stirred for 2 hours. The reaction solution was mixed with saturated sodium chloride solution (5 mL) and extracted with ethyl acetate (10 mL×3). The organic phases were combined, washed with saturated sodium chloride solution (20 mL), dried over anhydrous sodium sulfate, and filtered. The filtrate was concentrated under reduced pressure, and the residue was purified by thin layer chromatography with elution system B and subsequent elution system A to obtain the title compound 4-(3-(6-(difluoromethoxy)pyridin-3-yl)-4,4-dimethyl-5-oxo-2-thioxoimidazolidin-1-yl)-2-(trifluoromethyl)benzonitrile 30 (20 mg, yield 35.7%) as a yellow solid.

MS m/z (ESI): 457.3 [M+1]; $^1$H NMR (400 MHz, CDCl$_3$): δ 8.18-8.17 (m, 1H), 8.02-7.94 (m, 2H), 7.87-7.83 (m, 1H), 7.72-7.69 (m, 1H), 7.51 (t, 1H), 7.12-7.09 (m, 1H), 1.62 (s, 6H).

Example 31

2-(4-(3-(4-Cyano-3-(trifluoromethyl)phenyl)-5,5-dimethyl-4-oxo-2-thioxoimidazolidin-1-yl)-2-fluorophenoxy)acetic acid

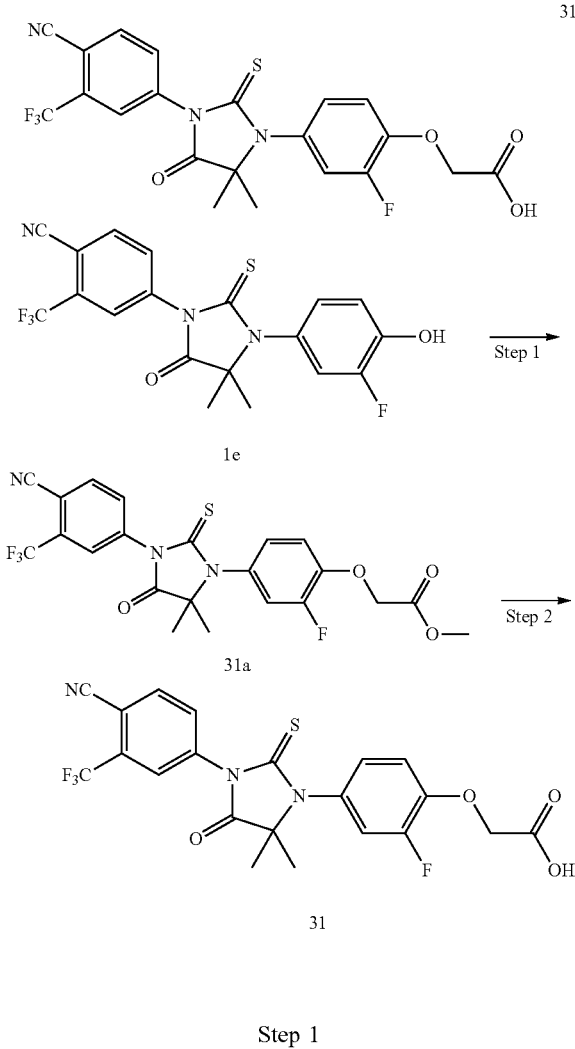

Step 1

Methyl 2-(4-(3-(4-cyano-3-(trifluoromethyl)phenyl)-5,5-dimethyl-4-oxo-2-thioxoimidazolidin-1-yl)-2-fluorophenoxy)acetate 4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of methyl glycolate (42 mg, 0.47 mmol), triphenylphosphine (93 mg, 0.35 mmol), 5 mL of dichloromethane, and diisopropyl azodicarboxylate (72 mg, 0.35 mmol), successively. The reaction solution was stirred for 1 hour. The reaction solution was concentrated under reduced pressure, and the residue was purified by thin layer chromatography with elution system A to obtain the title compound methyl 2-(4-(3-(4-cyano-3-(trifluoromethyl)phenyl)-5,5-dimethyl-4-oxo-2-thioxoimidazolidin-1-yl)-2-fluorophenoxy)acetate 31a (104 mg, yield 89.7%) as a white solid.

MS m/z (ESI): 496.2 [M+1]

Step 2

2-(4-(3-(4-Cyano-3-(trifluoromethyl)phenyl)-5,5-dimethyl-4-oxo-2-thioxoimidazolidin-1-yl)-2-fluorophenoxy)acetic acid Methyl 2-(4-(3-(4-cyano-3-(trifluoromethyl)phenyl)-5,5-dimethyl-4-oxo-2-thioxoimidazolidin-1-yl)-2-fluorophenoxy)acetate 31a (60 mg, 0.12 mmol) was dissolved in 4 mL of a mixture of tetrahydrofuran and methanol (v/v=1:1), followed by addition of 1 ml of sodium hydroxide (48 mg, 1.20 mmol). The reaction solution was stirred for 10 minutes. The reaction solution was concentrated under reduced pressure, followed by addition of ethyl acetate (5 mL). Then, 2 M hydrochloric acid was added dropwise to adjust the pH to 2-3. The reaction solution was dried over anhydrous sodium sulfate and filtered. The filtrate was concentrated under reduced pressure to obtain the title compound 2-(4-(3-(4-cyano-3-(trifluoromethyl)phenyl)-5,5-dimethyl-4-oxo-2-thioxoimidazolidin-1-yl)-2-fluorophenoxy)acetic acid 31 (58 mg, yield 99.5%) as a white solid.

MS m/z (ESI): 482.1 [M+1]

$^1$H NMR (400 MHz, CDCl$_3$): δ 8.00-7.96 (m, 2H), 7.85-7.83 (m, 1H), 7.14-7.05 (m, 3H), 4.83 (s, 2H), 1.60 (s, 6H).

Example 32

2-(4-(3-(4-Cyano-3-(trifluoromethyl)phenyl)-5,5-dimethyl-4-oxo-2-thioxoimidazolidin-1-yl)-2-fluorophenoxy)-N-methylacetamide

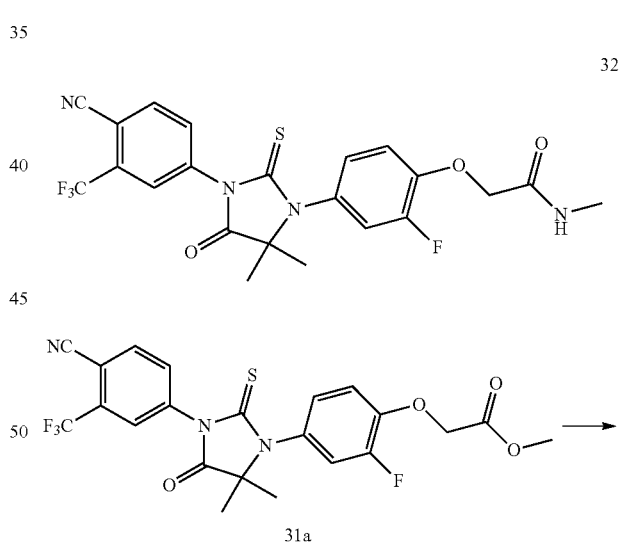

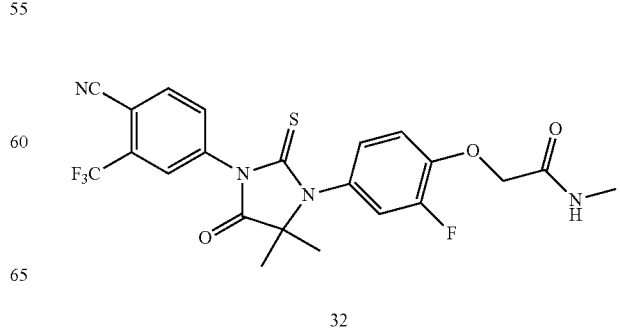

Methyl 2-(4-(3-(4-cyano-3-(trifluoromethyl)phenyl)-5,5-dimethyl-4-oxo-2-thioxoimidazolidin-1-yl)-2-fluorophenoxy)acetate 31a (44 mg, 0.09 mmol) was dissolved in 2 mL of tetrahydrofuran, followed by addition of methylamine alcoholic solution (5 mL). After reacting for 2 hours, the reaction solution was warmed up to 60° C. and stirred for 12 hours. The reaction solution was concentrated under reduced pressure, and the resulting residue was purified by thin layer chromatography with elution system A to obtain the title product 2-(4-(3-(4-cyano-3-(trifluoromethyl)phenyl)-5,5-dimethyl-4-oxo-2-thioxoimidazolidin-1-yl)-2-fluorophenoxy)-N-methylacetamide 32 (30 mg, yield 68.2%) as a white solid.

MS m/z (ESI): 495.2 [M+1]; $^1$H NMR (400 MHz, CDCl$_3$): δ 8.02-7.95 (m, 2H), 7.85-7.82 (m, 1H), 7.15-7.08 (m, 3H), 4.61 (s, 2H), 2.98 (d, 3H), 1.60 (s, 6H).

Example 33

1-((4-(3-(4-Cyano-3-(trifluoromethyl)phenyl)-5,5-dimethyl-4-oxo-2-thioxoimidazolidin-1-yl)-2-fluorophenoxy)methyl)cyclopropanecarboxylic acid

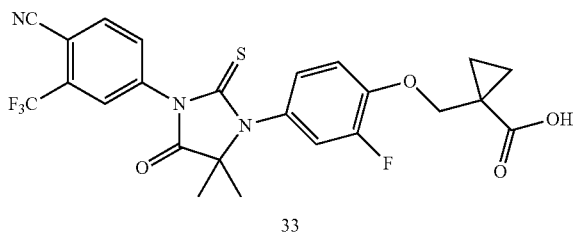

33

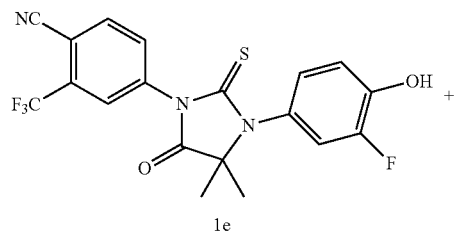

1e

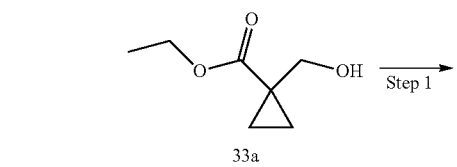

33a

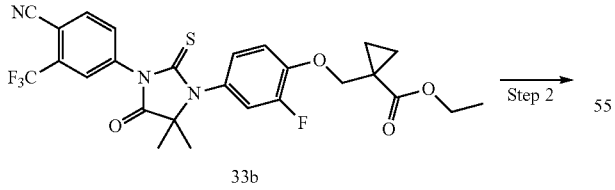

33b

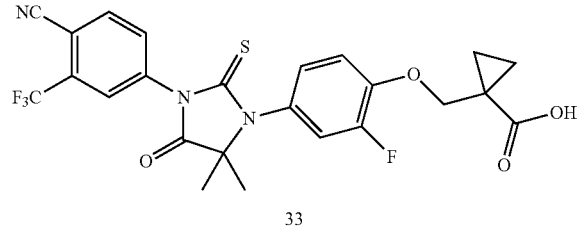

33

Step 1

Ethyl 1-((4-(3-(4-cyano-3-(trifluoromethyl)phenyl)-5,5-dimethyl-4-oxo-2-thioxoimidazolidin-1-yl)-2-fluorophenoxy)methyl)cyclopropanecarboxylate 4-(3-(3-Fluoro-4-hydroxyphenyl)-4,4-dimethyl-5-oxo-2-thioxoimidazolidin-1-yl)-2-(trifluoromethyl)benzonitrile 1e (50 mg, 0.12 mmol) was placed in a reaction flask, followed by addition of ethyl 1-(hydroxymethyl)cyclopropanecarboxylate 33a (20 mg, 0.14 mmol, prepared by a method disclosed in US Patent Application Publication U.S. 2012/110702 A1), triphenylphosphine (46 mg, 0.18 mmol), 8 mL of dichloromethane, and diisopropyl azodicarboxylate (36 mg, 0.18 mmol), successively in an ice bath at 0° C. The reaction solution was stirred for 1 hour, concentrated under reduced pressure, and the residue was purified by silica gel column chromatography with elution system B to obtain the title compound ethyl 1-((4-(3-(4-cyano-3-(trifluoromethyl)phenyl)-5,5-dimethyl-4-oxo-2-thioxoimidazolidin-1-yl)-2-fluorophenoxy)methyl)cyclopropanecarboxylate 33b (80 mg, yield>100%) as a yellow oil.

Step 2

1-((4-(3-(4-Cyano-3-(trifluoromethyl)phenyl)-5,5-dimethyl-4-oxo-2-thioxoimidazolidin-1-yl)-2-fluorophenoxy)methyl)cyclopropanecarboxylic acid Ethyl 1-((4-(3-(4-cyano-3-(trifluoromethyl)phenyl)-5,5-dimethyl-4-oxo-2-thioxoimidazolidin-1-yl)-2-fluorophenoxy)methyl)cyclopropanecarboxylate 33b (70 mg, 0.13 mmol) was dissolved in 8 mL of a mixture of tetrahydrofuran and methanol (v/v=1:1), followed by addition of 1 ml of sodium hydroxide (51 mg, 1.28 mmol). The reaction solution was warmed up to 50° C. and stirred for 1 hour. The reaction solution was concentrated under reduced pressure, followed by addition of water (50 mL) and ethyl acetate (50 mL). Then, 1 M hydrochloric acid was added dropwise to adjust the pH to 3-4. The reaction solution was separated, and the ethyl acetate phase was washed with water (10 mL×3) and saturated sodium chloride solution (10 mL×3), dried over anhydrous sodium sulfate, and filtered. The filtrate was concentrated under reduced pressure and the residue was purified by thin layer chromatography with elution system A to obtain the title compound 1-((4-(3-(4-cyano-3-(trifluoromethyl)phenyl)-5,5-dimethyl-4-oxo-2-thioxoimidazolidin-1-yl)-2-fluorophenoxy)methyl)cyclopropanecarboxylic acid 33 (40 mg, yield 60.6%) as a white solid.

MS m/z (ESI): 522.3 [M+1]; $^1$H NMR (400 MHz, CDCl$_3$): δ 7.96-7.95 (m, 2H), 7.84-7.83 (m, 1H), 7.11-7.04 (m, 3H), 4.26 (s, 2H), 1.58 (s, 6H), 1.52-1.51 (m, 2H), 1.19-1.18 (m, 2H).

Example 34

1-((4-(3-(4-Cyano-3-(trifluoromethyl)phenyl)-5,5-dimethyl-4-oxo-2-thioxoimidazolidin-1-yl)-2-fluorophenoxy)methyl)-N-methylcyclopropanecarboxamide

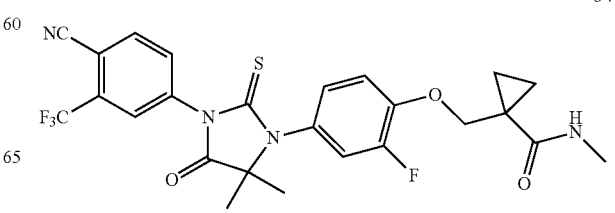

34

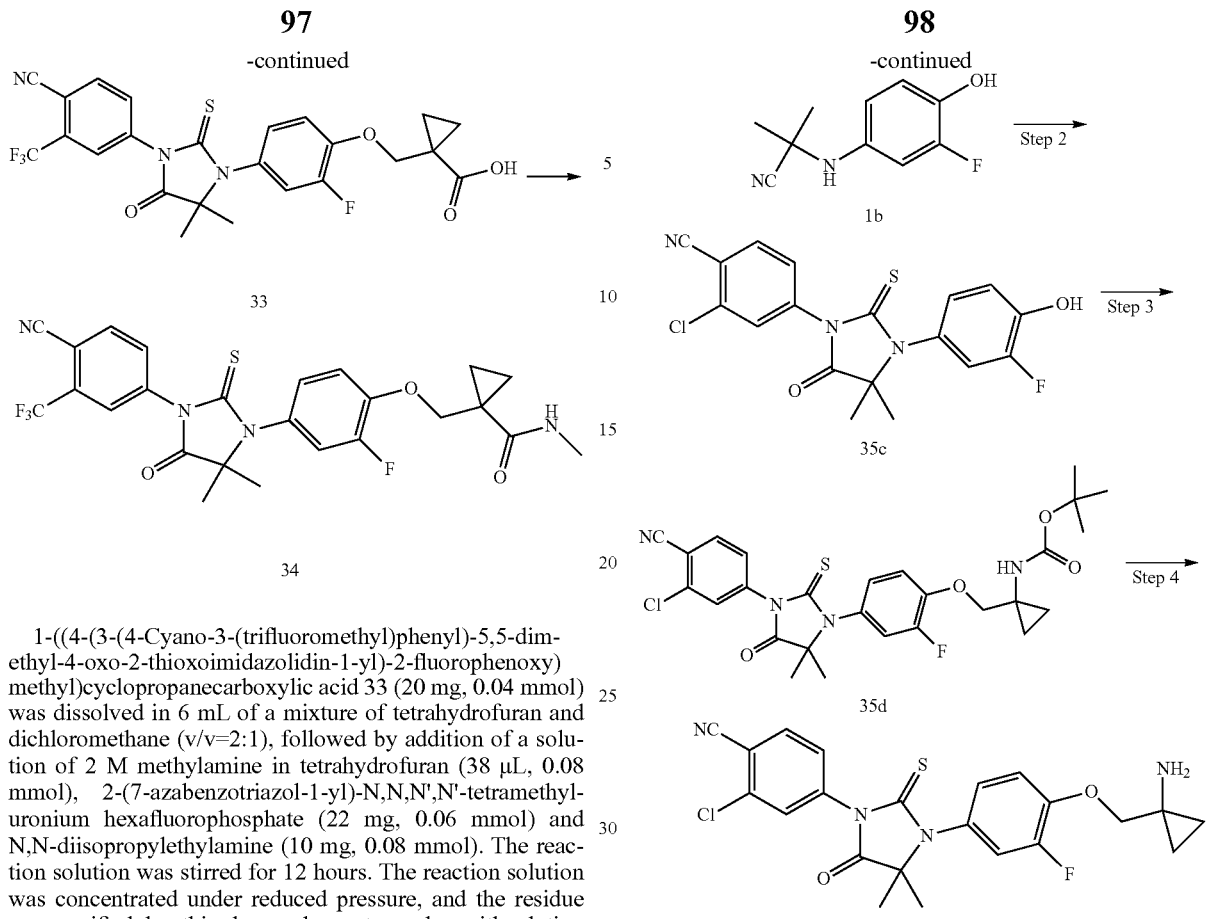

1-((4-(3-(4-Cyano-3-(trifluoromethyl)phenyl)-5,5-dimethyl-4-oxo-2-thioxoimidazolidin-1-yl)-2-fluorophenoxy)methyl)cyclopropanecarboxylic acid 33 (20 mg, 0.04 mmol) was dissolved in 6 mL of a mixture of tetrahydrofuran and dichloromethane (v/v=2:1), followed by addition of a solution of 2 M methylamine in tetrahydrofuran (38 μL, 0.08 mmol), 2-(7-azabenzotriazol-1-yl)-N,N,N',N'-tetramethyluronium hexafluorophosphate (22 mg, 0.06 mmol) and N,N-diisopropylethylamine (10 mg, 0.08 mmol). The reaction solution was stirred for 12 hours. The reaction solution was concentrated under reduced pressure, and the residue was purified by thin layer chromatography with elution system A to obtain the title compound 1-((4-(3-(4-cyano-3-(trifluoromethyl)phenyl)-5,5-dimethyl-4-oxo-2-thioxoimidazolidin-1-yl)-2-fluorophenoxy)methyl)-N-methylcyclopropanecarboxamide 34 (15 mg, yield 25.0%) as a white solid.

MS m/z (ESI): 535.2 [M+1]; $^1$H NMR (400 MHz, CDCl$_3$): δ 8.00-7.96 (m, 2H), 7.85-7.83 (m, 1H), 7.14-7.06 (m, 3H), 4.15 (s, 2H), 2.88 (d, 3H), 1.60 (s, 6H), 1.42-1.41 (m, 2H), 0.84-0.83 (m, 2H).

Example 35

4-(3-(4-((1-Aminocyclopropyl)methoxy)-3-fluorophenyl)-4,4-dimethyl-5-oxo-2-thioxoimidazolidin-1-yl)-2-chlorobenzonitrile

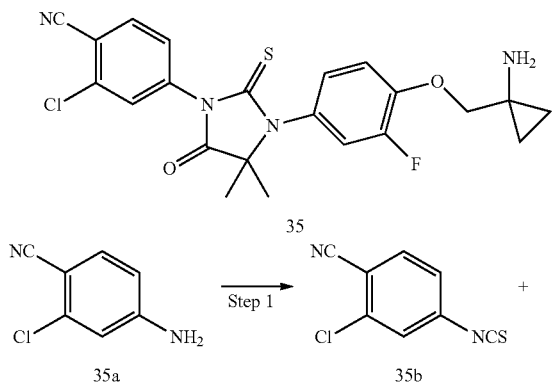

Step 1

2-Chloro-4-isothiocyanatobenzonitrile

4-Amino-2-chlorobenzonitrile 35a (12 g, 0.08 mol) was dissolved in 30 mL of 1,2-dichloroethane, followed by addition of thiophosgene (13.60 g, 0.12 mol). The reaction solution was warmed up to 60° C. After reacting for 12 hours, the reaction solution was cooled down to room temperature, poured into 100 mL of water, and the aqueous phase was extracted with ethyl acetate (100 mL×2). The organic phases were combined, washed with saturated sodium chloride solution (100 mL×2), dried over anhydrous sodium sulfate, and filtered. The filtrate was concentrated under reduced pressure, and the residue was purified by silica gel column chromatography with elution system B to obtain the title compound 2-chloro-4-isothiocyanatobenzonitrile 35b (8.50 g, yield 56.7%) as a yellow solid.

Step 2

2-Chloro-4-(3-(3-fluoro-4-hydroxyphenyl)-4,4-dimethyl-5-oxo-2-thioxoimidazolidin-1-yl)benzonitrile 2-Chloro-4-isothiocyanatobenzonitrile 35b (2.20 g, 11.30 mmol) was dissolved in 20 mL of N,N-dimethylacetamide, followed by addition of 2-((3-fluoro-4-hydroxyphenyl)amino)-2-methylpropanenitrile 1b (2 g, 10.30 mmol). The reaction solution was warmed up to 60° C. and stirred for 12 hours, followed by addition of 20 mL of methanol and 20 mL of 2 M hydrochloric acid. The reaction solution was warmed up to 75° C. and stirred for 2 hours. The reaction solution was cooled down to room temperature, mixed with H₂O (30 mL), and extracted with ethyl acetate (30 mL×2). The organic phases were combined, washed with saturated sodium chloride solution (30 mL×3), dried over anhydrous sodium sulfate, and filtered. The filtrate was concentrated under reduced pressure and the residue was purified by silica gel column chromatography with elution system B to obtain the title compound 2-chloro-4-(3-(3-fluoro-4-hydroxyphenyl)-4,4-dimethyl-5-oxo-2-thioxoimidazolidin-1-yl)benzonitrile 35c (2.20 g, yield 45.9%) as a solid solid.

Step 3 tert-Butyl (1-((4-(3-(3-chloro-4-cyanophenyl)-5,5-dimethyl-4-oxo-2-thioxoimidazolidin-1-yl)-2-fluorophenoxy)methyl)cyclopropyl)carbamate 2-Chloro-4-(3-(3-fluoro-4-hydroxyphenyl)-4,4-dimethyl-5-oxo-2-thioxoimidazolidin-1-yl)benzonitrile 35c (100 mg, 0.26 mmol) was dissolved in 5 mL of methylbenzene, followed by addition of tert-butyl (1-(hydroxymethyl)cyclopropyl)carbamate 6a (49 mg, 0.26 mmol), 1,1'-(azodicarbonyl)dipiperidine (106 mg, 0.42 mmol), and tri-n-butylphosphine (85 mg, 0.42 mmol), successively. The reaction solution was warmed up to 50° C. and stirred for 2 hours. The resulting solution was concentrated under reduced pressure. The residue was purified by silica gel column chromatography with elution system B to obtain the title compound tert-butyl (1-((4-(3-(3-chloro-4-cyanophenyl)-5,5-dimethyl-4-oxo-2-thioxoimidazolidin-1-yl)-2-fluorophenoxy)methyl)cyclopropyl)carbamate 35d (80 mg, yield 55.9%) as a white solid.

Step 4
4-(3-(4-((1-Aminocyclopropyl)methoxy)-3-fluorophenyl)-4,4-dimethyl-5-oxo-2-thioxoimidazolidin-1-yl)-2-chlorobenzonitrile tert-Butyl (1-((4-(3-(3-chloro-4-cyanophenyl)-5,5-dimethyl-4-oxo-2-thioxoimidazolidin-1-yl)-2-fluorophenoxy)methyl)cyclopropyl)carbamate 35d (70 mg, 0.13 mmol) was dissolved in 3 mL of a solution of 2 M hydrogen chloride in methanol and stirred for 2 hours. The reaction solution was concentrated under reduced pressure and the residue was washed with diethyl ether (10 mL), and dried to obtain the title product 4-(3-(4-((1-aminocyclopropyl)methoxy)-3-fluorophenyl)-4,4-dimethyl-5-oxo-2-thioxoimidazolidin-1-yl)-2-chlorobenzonitrile 35 (60 mg, yield 96.7%) as a yellow solid.

MS m/z (ESI): 459.2 [M+1]; ¹H NMR (400 MHz, CDCl₃): δ 7.97-7.95 (m, 1H), 7.85 (s, 1H), 7.64-7.62 (m, 1H), 7.31-7.27 (m, 2H), 7.19-7.17 (m, 1H), 4.27 (s, 2H), 1.54 (s, 6H), 1.16-1.13 (m, 4H).

Example 36

4-(3-(4-((1-Acetylpyrrolidin-3-yl)oxy)-3-fluorophenyl)-4,4-dimethyl-5-oxo-2-thioxoimidazolidin-1-yl)-2-(trifluoromethyl)benzonitrile

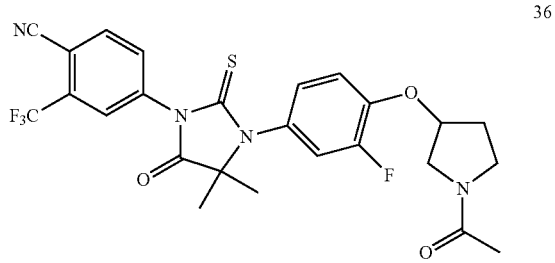

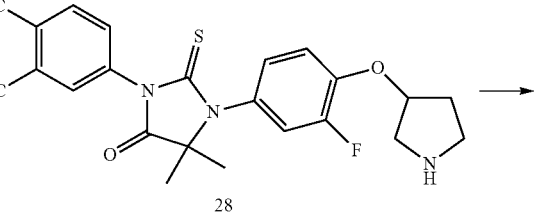

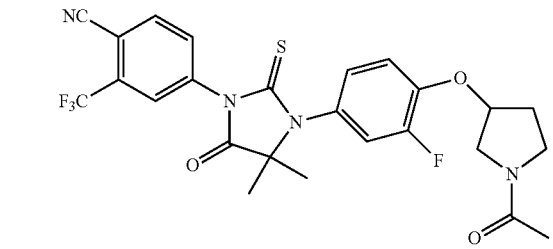

4-(3-(3-Fluoro-4-((pyrrolidin-3-yl)oxy)phenyl)-4,4-dimethyl-5-oxo-2-thioxoimidazolidin-1-yl)-2-(trifluoromethyl)benzonitrile 28 (50 mg, 0.10 mmol) was dissolved in 5 mL of dichloromethane and cooled down to 0° C., followed by addition of triethylamine (20 mg, 0.20 mmol), 4-dimethylaminopyridine (12 mg, 0.10 mmol), and dropwise addition of acetyl chloride (16 mg, 0.20 mmol). The reaction solution was stirred for 30 minutes at 0° C. The reaction solution was concentrated under reduced pressure, and the residue was purified by thin layer chromatography with elution system A to obtain the title compound 4-(3-(4-((1-acetylpyrrolidin-3-yl)oxy)-3-fluorophenyl)-4,4-dimethyl-5-oxo-2-thioxoimidazolidin-1-yl)-2-(trifluoromethyl)benzonitrile 36 (20 mg, yield 37.0%) as a white solid.

MS m/z (ESI): 535.2 [M+1]; ¹H NMR (400 MHz, CDCl₃): δ 8.00-7.96 (m, 2H), 7.85-7.83 (m, 1H), 7.12-7.00 (m, 3H), 3.75-3.60 (m, 4H), 2.42-2.27 (m, 3H), 2.18 (s, 3H), 1.60 (s, 6H).

Example 37

4-(3-(4-((1-Aminocyclopropyl)methoxy)phenyl)-4,4-dimethyl-5-oxo-2-thioxoimidazolidin-1-yl)-2-(trifluoromethyl)benzonitrile

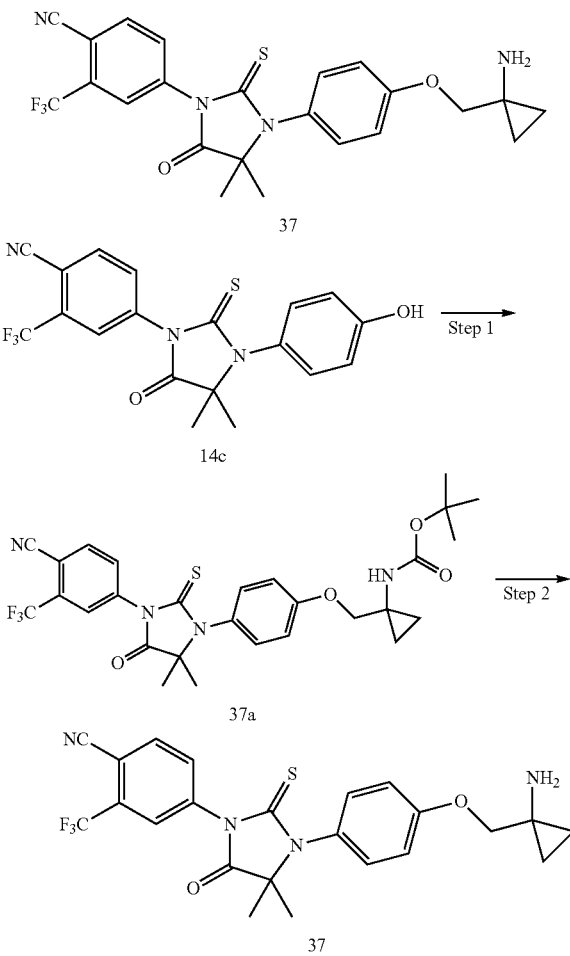

Step 1 tert-Butyl (1-((4-(3-(4-cyano-3-(trifluoromethyl)phenyl)-5,5-dimethyl-4-oxo-2-thioxoimidazolidin-1-yl)phenoxy)methyl)cyclopropyl)carbamate 4-(3-(4-Hydroxyphenyl)-4,4-dimethyl-5-oxo-2-thioxoimidazolidin-1-yl)-2-(trifluoromethyl)benzonitrile 14c (100 mg, 0.25 mmol) was placed in a reaction flask, followed by addition of tert-butyl (1-(hydroxymethyl)cyclopropyl)carbamate 6a (93 mg, 0.49 mmol), triphenylphosphine (97 mg, 0.37 mmol), 5 mL of dichloromethane, and diisopropyl azodicarboxylate (75 mg, 0.37 mmol), successively. The reaction solution was stirred for 2 hours. The reaction solution was concentrated under reduced pressure, and the residue was purified by thin layer chromatography with elution system A to obtain the title compound tert-butyl (1-((4-(3-(4-cyano-3-(trifluoromethyl)phenyl)-5,5-dimethyl-4-oxo-2-thioxoimidazolidin-1-yl)phenoxy)methyl)cyclopropyl)carbamate 37a (50 mg, yield 35.2%) as a white solid.

MS m/z (ESI): 519.3 [M−56+1]

Step 2

4-(3-(4-((1-Aminocyclopropyl)methoxy)phenyl)-4,4-dimethyl-5-oxo-2-thioxoimidazolidin-1-yl)-2-(trifluoromethyl)benzonitrile tert-Butyl (1-((4-(3-(4-cyano-3-(trifluoromethyl)phenyl)-5,5-dimethyl-4-oxo-2-thioxoimidazolidin-1-yl)phenoxy)methyl)cyclopropyl)carbamate 37a (50 mg, 0.09 mmol) was dissolved in 5 mL of a solution of 2 M hydrogen chloride in methanol and stirred for 2 hours. The reaction solution was concentrated under reduced pressure to obtain the title compound 4-(3-(4-((1-aminocyclopropyl)methoxy)phenyl)-4,4-dimethyl-5-oxo-2-thioxoimidazolidin-1-yl)-2-(trifluoromethyl)benzonitrile 37 (50 mg, yield>100%) as a yellow solid.

MS m/z (ESI): 475.3 [M+1]; $^1$H NMR (400 MHz, CDCl$_3$): δ 8.40-8.38 (m, 1H), 8.29-8.28 (m, 1H), 8.09-8.06 (m, 1H), 7.34-7.31 (m, 2H), 7.16-7.11 (m, 2H), 4.15 (s, 2H), 1.50 (s, 6H), 1.09-1.06 (m, 2H), 0.99-0.94 (m, 2H).

Example 38

4-(3-(4-((1-Aminocyclopropyl)methoxy)-3-fluorophenyl)-4,4-dimethyl-5-oxo-2-thioxoimidazolidin-1-yl)-2-methylbenzonitrile

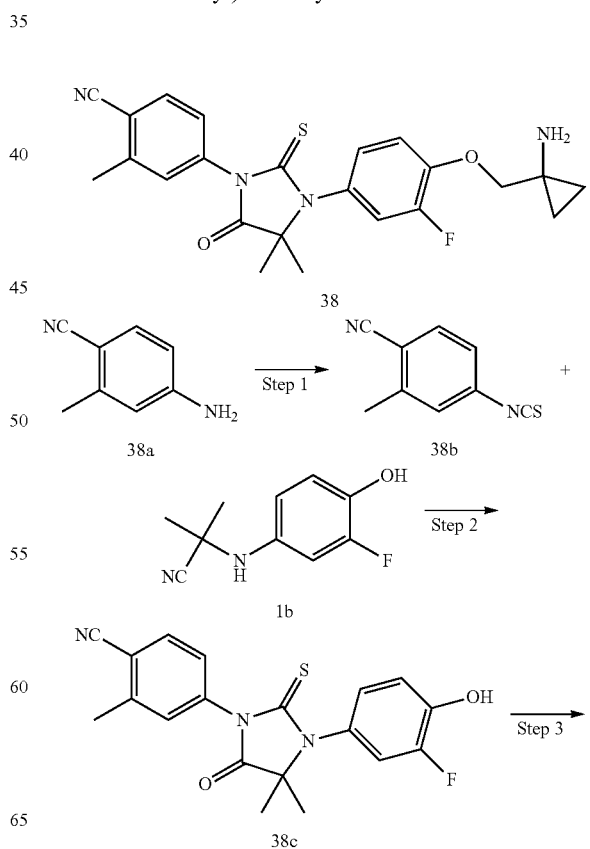

-continued

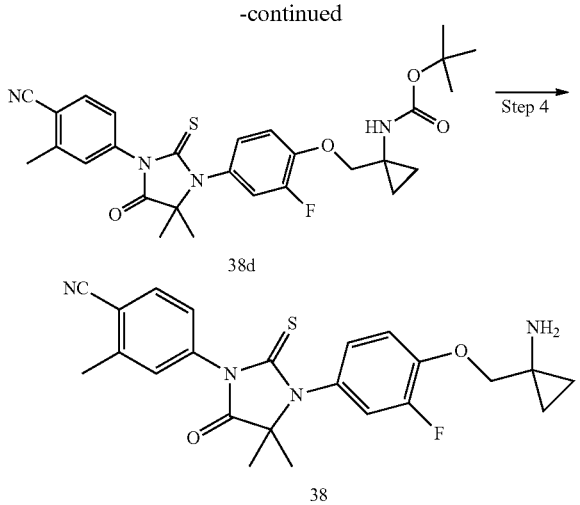

Step 1

4-Isothiocyanato-2-methylbenzonitrile

4-Amino-2-methylbenzonitrile 38a (110 mg, 0.83 mmol) was dissolved in 5 mL of tetrahydrofuran and cooled down to 0° C., followed by addition of thiophosgene (115 mg, 0.99 mmol). The reaction solution was stirred for 1 hour at 0° C., then mixed with $H_2O$ (20 mL) and extracted with ethyl acetate (20 mL×3). The organic phases were combined, washed with saturated sodium chloride solution (20 mL×3), dried over anhydrous sodium sulfate, and filtered. The filtrate was concentrated under reduced pressure to obtain the title compound 4-isothiocyanato-2-methylbenzonitrile 38b (130 mg, yield 89.7%) as a white solid.

Step 2

4-(3-(3-Fluoro-4-hydroxyphenyl)-4,4-dimethyl-5-oxo-2-thioxoimidazolidin-1-yl)-2-methylbenzonitrile 4-isothiocyanato-2-methylbenzonitrile 38b (110 mg, 0.63 mmol) was dissolved in 3 mL of N,N-dimethylacetamide, followed by addition of 2-((3-fluoro-4-hydroxyphenyl)amino)-2-methylpropanenitrile 1b (98 mg, 0.50 mmol). The reaction solution was stirred for 12 hours, followed by addition of methanol (1.5 mL) and 2 M hydrochloric acid (1.5 mL). The reaction solution was warmed up to 80° C. After reacting for 2 hours, the reaction solution was cooled down to room temperature, mixed with 20 mL of $H_2O$, and extracted with ethyl acetate (15 mL×3). The organic phases were combined, washed with saturated sodium chloride solution (20 mL×3), dried over anhydrous sodium sulfate, and filtered. The filtrate was concentrated under reduced pressure, and the residue was purified by thin layer chromatography with elution system B to obtain the title compound 4-(3-(3-fluoro-4-hydroxyphenyl)-4,4-dimethyl-5-oxo-2-thioxoimidazolidin-1-yl)-2-methylbenzonitrile 38c (20 mg, yield 10.7%) as a yellow solid.
MS m/z (ESI): 370.1 [M+1]

Step 3 tert-Butyl (1-((4-(3-(4-cyano-3-methylphenyl)-5,5-dimethyl-4-oxo-2-thioxoimidazolidin-1-yl)-2-fluorophenoxy)methyl)cyclopropyl)carbamate 4-(3-(3-Fluoro-4-hydroxyphenyl)-4,4-dimethyl-5-oxo-2-thioxoimidazolidin-1-yl)-2-methylbenzonitrile 38c (22 mg, 0.06 mmol) was placed in a reaction flask, followed by addition of tert-butyl (1-(hydroxymethyl)cyclopropyl)carbamate 6a (12 mg, 0.07 mmol), 1,1'-(azodicarbonyl)dipiperidine (24 mg, 0.10 mmol), 5 mL of methylbenzene, and tri-n-butylphosphine (19 mg, 0.10 mmol), successively. The reaction solution was warmed up to 50° C. and stirred for 24 hours. The reaction solution was concentrated under reduced pressure, and the resulting residue was purified by thin layer chromatography with elution system B to obtain the title compound tert-butyl (1-((4-(3-(4-cyano-3-methylphenyl)-5,5-dimethyl-4-oxo-2-thioxoimidazolidin-1-yl)-2-fluorophenoxy)methyl)cyclopropyl)carbamate 38d (17 mg, yield 52.9%) as a white solid.
MS m/z (ESI): 483.3 [M−56+1]

Step 4

4-(3-(4-((1-Aminocyclopropyl)methoxy)-3-fluorophenyl)-4,4-dimethyl-5-oxo-2-thioxoimidazolidin-1-yl)-2-methylbenzonitrile tert-Butyl (1-((4-(3-(4-cyano-3-methylphenyl)-5,5-dimethyl-4-oxo-2-thioxoimidazolidin-1-yl)-2-fluorophenoxy)methyl)cyclopropyl)carbamate 38d (16 mg, 0.03 mmol) was dissolved in 2 mL of a solution of 4 M hydrogen chloride in methanol. The reaction solution was stirred for 1 hour. The reaction solution was concentrated under reduced pressure to obtain the title product 4-(3-(4-((1-aminocyclopropyl)methoxy)-3-fluorophenyl)-4,4-dimethyl-5-oxo-2-thioxoimidazolidin-1-yl)-2-methylbenzonitrile 38 (14 mg, yield 99.3%) as a white solid.
MS m/z (ESI): 439.3 [M+1]; $^1$H NMR (400 MHz, $CDCl_3$): δ 7.79 (d, 1H), 7.52 (s, 1H), 7.42 (d, 1H), 7.26 (t, 2H), 7.18 (d, 1H), 4.28 (s, 2H), 2.59 (s, 3H), 1.54 (s, 6H), 1.12-1.17 (m, 4H).

Example 39

4-(3-(4-((1-Cyanocyclopropyl)methoxy)-3-fluorophenyl)-4,4-dimethyl-5-oxo-2-thioxoimidazolidin-1-yl)-2-(trifluoromethyl)benzonitrile

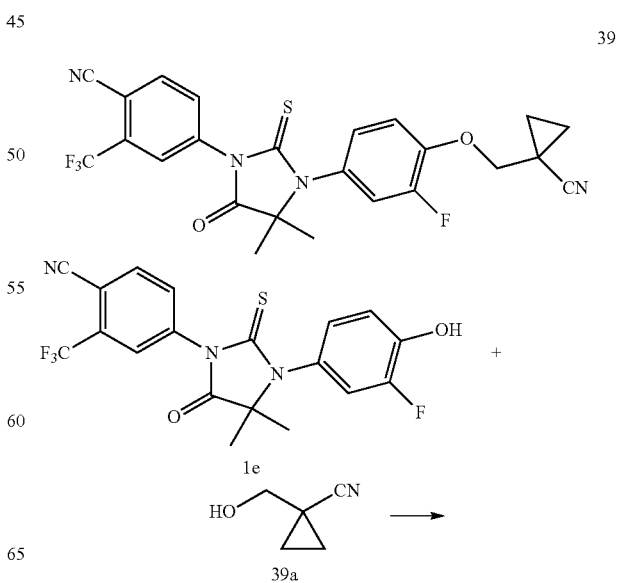

105

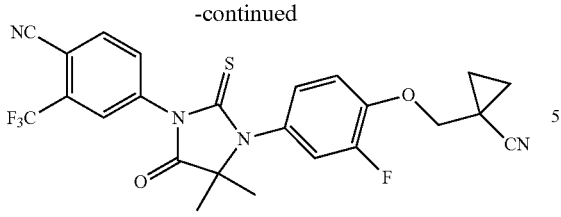

39

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was placed in a reaction flask, followed by addition of 1-(hydroxymethyl)cyclopropanecarbonitrile 39a (28 mg, 0.28 mmol, prepared by a well known method described in *Bioorganic and Medicinal Chemistry Letters*, 2009, 19(6), 1797-1801), 1,1'-(azodicarbonyl)dipiperidine (95 mg, 0.38 mmol), 10 mL of methylbenzene, and tri-n-butylphosphine (76 mg, 0.38 mmol), successively. The reaction solution was warmed up to 50° C. and stirred for 12 hours. The reaction solution was concentrated under reduced pressure, and the resulting residue was purified by thin layer chromatography with elution system A to obtain the title compound 4-(3-(4-((1-cyanocyclopropyl)methoxy)-3-fluorophenyl)-4,4-dimethyl-5-oxo-2-thioxoimidazolidin-1-yl)-2-(trifluoromethyl)benzonitrile 39 (110 mg, yield 93.2%) as a white solid.

MS m/z (ESI): 503.3 [M+1]; $^1$H NMR (400 MHz, CDCl$_3$): δ 7.95-8.00 (m, 2H), 7.84 (d, 1H), 7.04-7.11 (m, 3H), 4.12 (s, 2H), 1.59 (s, 6H), 1.45 (t, 2H), 1.18 (t, 2H).

Example 40

4-(4,4-Dimethyl-3-(4-((oxetan-3-yl)oxy)phenyl)-5-oxo-2-thioxoimidazolidin-1-yl)-2-(trifluoromethyl)benzonitrile

106

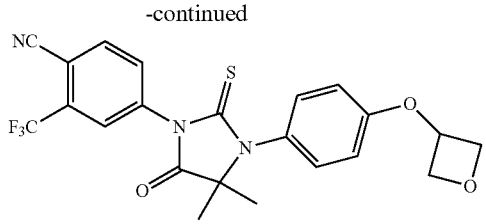

40

4-(3-(4-Hydroxyphenyl)-4,4-dimethyl-5-oxo-2-thioxoimidazolidin-1-yl)-2-(trifluoromethyl)benzonitrile 14c (100 mg, 0.25 mmol) was dissolved in 5 mL of N,N-dimethylacetamide, followed by addition of oxetan-3-yl-4-methylbenzenesulfonate 40a (114 mg, 0.50 mmol, prepared by a well known method described in *Organic Letters*, 2008, 10(15), 3259-3262) and potassium carbonate (103 mg, 0.75 mmol). The reaction solution was warmed up to 80° C. After reacting for 12 hours, the reaction solution was cooled down to room temperature, mixed with 20 mL of H$_2$O, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system A to obtain the title compound 4-(4,4-dimethyl-3-(4-((oxetan-3-yl)oxy)phenyl)-5-oxo-2-thioxoimidazolidin-1-yl)-2-(trifluoromethyl) benzonitrile 40 (20 mg, yield 17.7%) as a yellow solid.

MS m/z (ESI): 462.3 [M+1]; $^1$H NMR (400 MHz, CDCl$_3$): δ 7.99-7.96 (m, 2H), 7.86-7.83 (m, 1H), 7.23-7.20 (m, 2H), 6.86-6.83 (m, 2H), 5.27-5.24 (m, 1H), 5.03-4.99 (m, 2H), 4.83-4.80 (m, 2H), 1.58 (s, 6H).

Example 41

4-(3-(3-Fluoro-4-((oxetan-3-yl)oxy)phenyl)-4,4-dimethyl-5-oxo-2-thioxoimidazolidin-1-yl)-2-(trifluoromethyl)benzonitrile

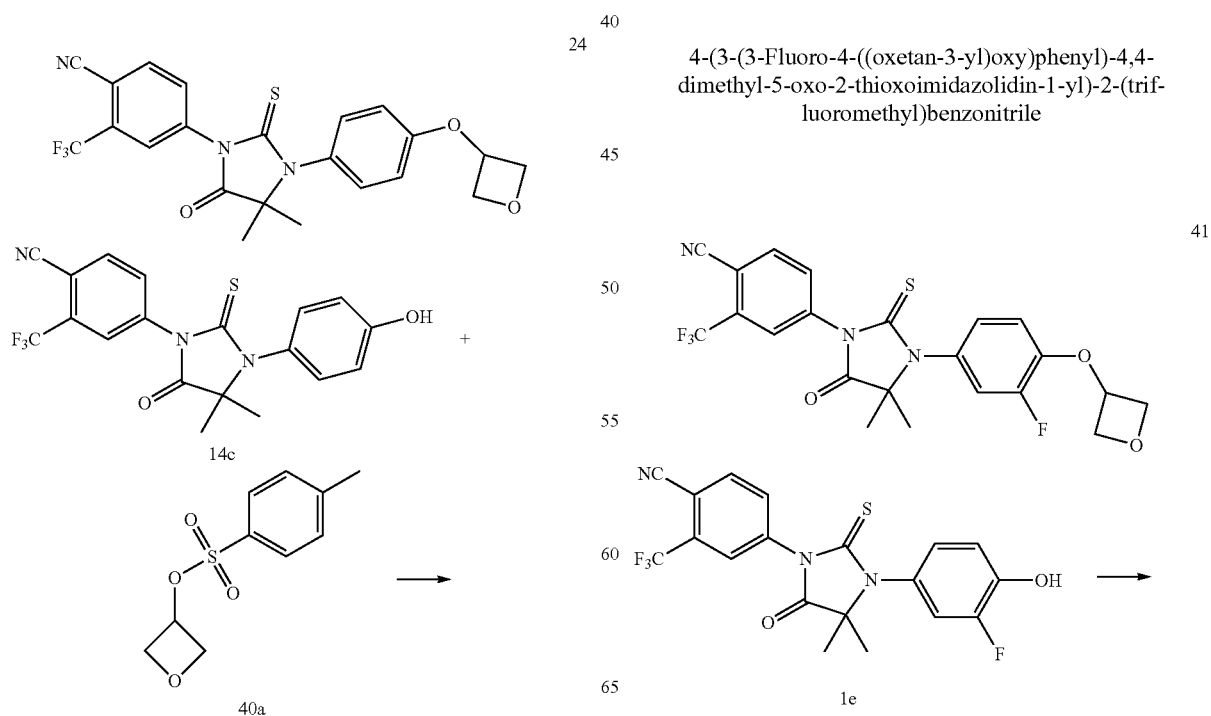

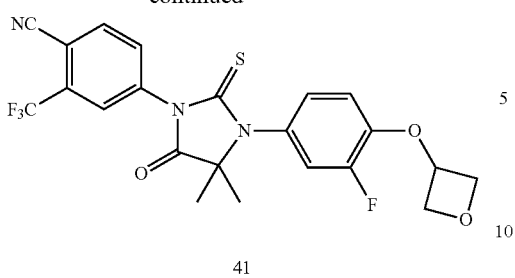

41

4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was dissolved in 5 mL of N,N-dimethylacetamide, followed by addition of oxetan-3-yl-4-methylbenzenesulfonate 40a (110 mg, 0.48 mmol) and potassium carbonate (100 mg, 0.72 mmol). The reaction solution was warmed up to 80° C. After reacting for 4 hours, the reaction solution was cooled down to room temperature, mixed with 20 mL of $H_2O$, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system A to obtain the title compound 4-(3-(3-fluoro-4-((oxetan-3-yl)oxy)phenyl)-4,4-dimethyl-5-oxo-2-thioxoimidazolidin-1-yl)-2-(trifluoromethyl)benzonitrile 41 (30 mg, yield 26.5%) as a white solid.

MS m/z (ESI): 480.3 [M+1]; $^1$H NMR (400 MHz, $CDCl_3$): δ 8.00-7.95 (m, 2H), 7.84-7.82 (m, 1H), 7.12-7.09 (m, 1H), 7.01-7.00 (m, 1H), 6.75-6.71 (m, 1H), 5.32-5.30 (m, 1H), 5.03-4.99 (m, 2H), 4.89-4.86 (m, 2H), 1.59 (s, 6H).

Example 42

4-(3-(4-((Azetidin-3-yl)oxy)-3-fluorophenyl)-4,4-dimethyl-5-oxo-2-thioxoimidazolidin-1-yl)-2-(trifluoromethyl)benzonitrile

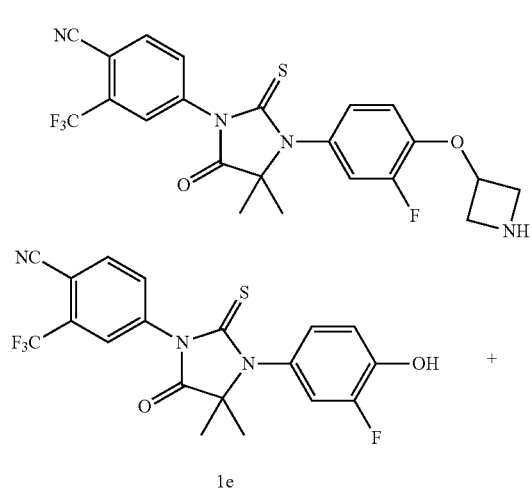

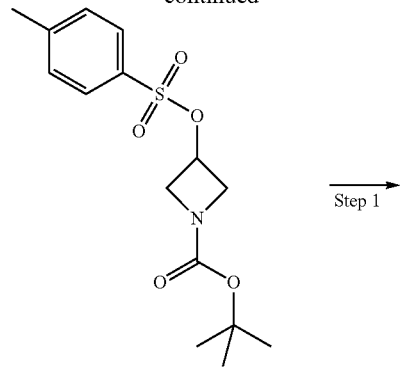

Step 1 tert-Butyl 3-(4-(3-(4-cyano-3-(trifluoromethyl)phenyl)-5,5-dimethyl-4-oxo-2-thioxoimidazolidin-1-yl)-2-fluorophenoxy)azetidine-1-carboxylate 4-(3-(3-Fluoro-4-hydroxyphenyl)-4,4-dimethyl-5-oxo-2-thioxoimidazolidin-1-yl)-2-(trifluoromethyl)benzonitrile 1e (100 mg, 0.24 mmol) was dissolved in 5 mL of N,N-dimethylacetamide, followed by addition of tert-butyl 3-(tosyloxy)azetidine-1-carboxylate 42a (157 mg, 0.48 mmol, prepared by a method disclosed in PCT Patent Application Publication WO 2011/103196 A1) and potassium carbonate (100 mg, 0.72 mmol). The reaction solution was warmed up to 90° C. After reacting for 4 hours, the reaction solution was cooled down to room temperature, mixed with 20 mL of $H_2O$, and extracted with ethyl acetate (20 mL×2). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system A to obtain the title compound tert-butyl 3-(4-(3-(4-cyano-3-(trifluoromethyl)phenyl)-5,5-dimethyl-4-oxo-2-thioxoimidazolidin-1-yl)-2-fluorophenoxy)azetidine-1-carboxylate 42b (70 mg, yield 51.4%) as a white solid.

Step 2

4-(3-(4-((Azetidin-3-yl)oxy)-3-fluorophenyl)-4,4-dimethyl-5-oxo-2-thioxoimidazolidin-1-yl)-2-(trifluoromethyl)benzonitrile tert-Butyl 3-(4-(3-(4-cyano-3-(trifluoromethyl)phenyl)-5,5-dimethyl-4-oxo-2-thioxoimidazolidin-1-yl)-2-fluorophenoxy)azetidine-1-carboxylate 42b (70 mg, 0.12 mmol) was dissolved in 3 mL of a solution of 4 M hydrogen chloride in methanol and stirred for 12 hours. The reaction solution was concentrated under reduced pressure to obtain the title product 4-(3-(4-((azetidin-3-yl)oxy)-3-fluorophenyl)-4,4-dimethyl-5-oxo-2-thioxoimidazolidin-1-yl)-2-(trifluoromethyl)benzonitrile 42 (60 mg, yield 96.3%) as a white solid.

MS m/z (ESI): 479.3 [M+1]; $^1$H NMR (400 MHz, CDCl$_3$): δ 9.22 (S, 1H), 8.39-8.37 (m, 1H), 8.26-8.25 (m, 1H), 8.06-8.03 (m, 1H), 7.42-7.38 (m, 1H), 7.18-7.12 (m, 2H), 5.22-5.19 (m, 1H), 4.49-4.44 (m, 2H), 4.10-4.09 (m, 2H), 1.50 (s, 6H).

Example 43

4-(3-(4-((1,3-Dihydroxypropan-2-yl)oxy)-3-fluorophenyl)-4,4-dimethyl-5-oxo-2-thioxoimidazolidin-1-yl)-2-(trifluoromethyl)benzonitrile

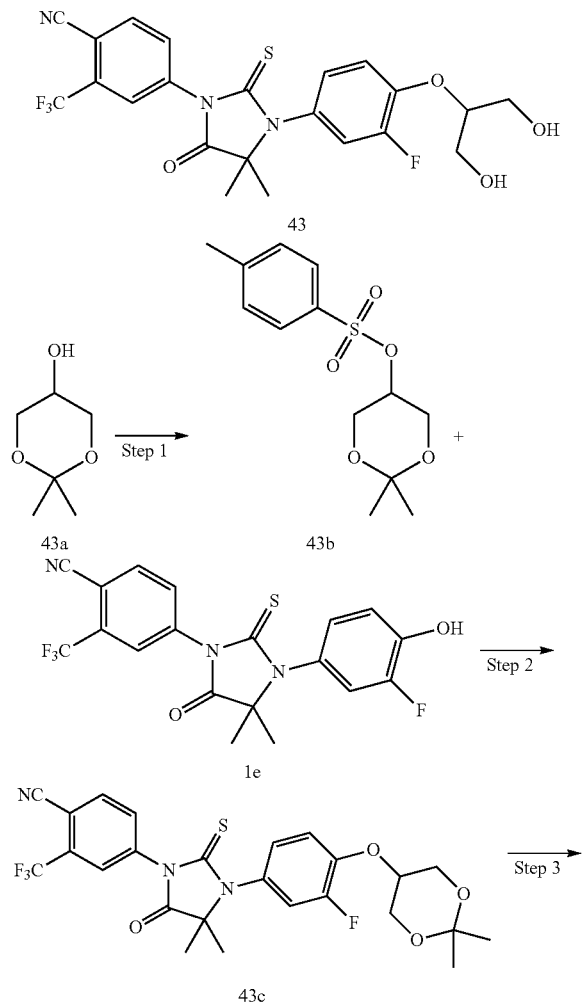

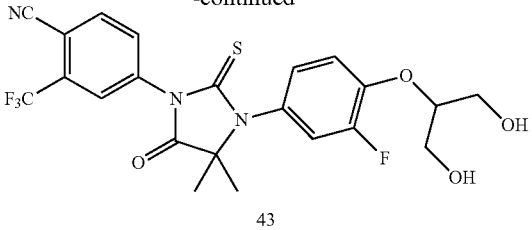

43

Step 1

2,2-Dimethyl-1,3-dioxan-5-yl-4-methylbenzenesulfonate

2,2-Dimethyl-1,3-dioxan-5-ol 43a (200 mg, 1.51 mmol, prepared by a method disclosed in US Patent Application Publication U.S. 2007/10542 A1) was dissolved in 30 mL of dichloromethane, followed by addition of p-toluenesulfonyl chloride (420 mg, 2.20 mmol) and triethylamine (300 mg, 2.97 mmol). The reaction solution was stirred for 3 hours, washed with saturated sodium chloride solution (20 mL×2), dried over anhydrous sodium sulfate, and filtered. The filtrate was concentrated under reduced pressure and the residue was purified by silica gel column chromatography with elution system B to obtain the title compound 2,2-dimethyl-1,3-dioxan-5-yl 4-methylbenzenesulfonate 43b (100 mg, yield 23.3%) as a colourless oil.

MS m/z (ESI): 287.2 [M+1]

Step 2

4-(3-(4-((2,2-Dimethyl-1,3-dioxan-5-yl)oxy)-3-fluorophenyl)-4,4-dimethyl-5-oxo-2-thioxoimidazolidin-1-yl)-2-(trifluoromethyl)benzonitrile

4-(3-(3-Fluoro-4-hydroxyphenyl)-4,4-dimethyl-5-oxo-2-thioxoimidazolidin-1-yl)-2-(trifluoromethyl)benzonitrile 1e (200 mg, 0.47 mmol) was dissolved in 5 mL of N,N-dimethylformamide, followed by addition of 2,2-dimethyl-1,3-dioxan-5-yl-4-methylbenzenesulfonate 43b (200 mg, 0.71 mmol) and potassium carbonate (130 mg, 0.94 mmol). The reaction solution was warmed up to 60° C. After reacting for 6 hours, the reaction solution was cooled down to room temperature, mixed with 20 mL of water, and extracted with ethyl acetate (30 mL×2). The organic phases were combined, washed with saturated sodium chloride solution (20 mL×2), dried over anhydrous sodium sulfate, and filtered. The filtrate was concentrated under reduced pressure, and the residue was purified by thin layer chromatography with elution system B to obtain the title compound 4-(3-(4-((2,2-dimethyl-1,3-dioxan-5-yl)oxy)-3-fluorophenyl)-4,4-dimethyl-5-oxo-2-thioxoimidazolidin-1-yl)-2-(trifluoromethyl)benzonitrile 43c (170 mg, yield 67.1%) as a white solid.

MS m/z (ESI): 538.3 [M+1]

Step 3

4-(3-(4-((1,3-Dihydroxypropan-2-yl)oxy)-3-fluorophenyl)-4,4-dimethyl-5-oxo-2-thioxoimidazolidin-1-yl)-2-(trifluoromethyl)benzonitrile

4-(3-(4-((2,2-Dimethyl-1,3-dioxan-5-yl)oxy)-3-fluorophenyl)-4,4-dimethyl-5-oxo-2-thioxoimidazolidin-1-yl)-2-

(trifluoromethyl)benzonitrile 43c (70 mg, 0.12 mmol) was dissolved in 10 mL of methanol, followed by addition of 1 M hydrochloric acid (1 mL). The reaction solution was stirred for 2 hours, mixed with 10 mL of water and 20 mL of saturated potassium carbonate solution, and extracted with ethyl acetate (30 mL×2). The organic phases were combined, washed with saturated sodium chloride solution (30 mL×3), dried over anhydrous sodium sulfate, and filtered. The filtrate was concentrated under reduced pressure, and the residue was purified by thin layer chromatography with elution system A to obtain the title compound 4-(3-(4-((1,3-dihydroxypropan-2-yl)oxy)-3-fluorophenyl)-4,4-dimethyl-5-oxo-2-thioxoimidazolidin-1-yl)-2-(trifluoromethyl)benzonitrile 43 (40 mg, yield 43.4%) as a white solid.

MS m/z (ESI): 498.3 [M+1]; $^1$H NMR (400 MHz, CDCl$_3$): δ 8.00-7.95 (m, 2H), 7.84-7.82 (m, 1H), 7.29-7.26 (m, 1H), 7.11-7.03 (m, 2H), 4.51-4.47 (m, 1H), 3.978 (s, 4H), 1.59 (s, 6H).

Example 44

(S)-4-(3-(4-(2,3-Dihydroxypropoxy)phenyl)-4,4-dimethyl-5-oxo-2-thioxoimidazolidin-1-yl)-2-(trifluoromethyl)benzonitrile

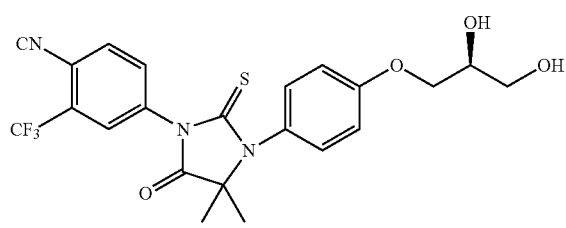

44

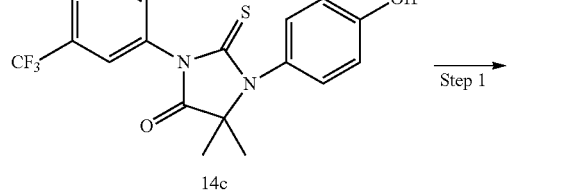

14c

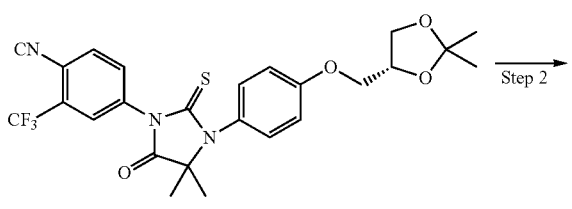

44a

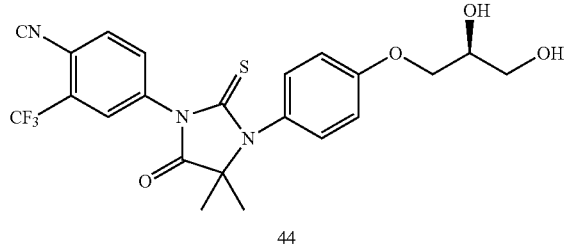

44

Step 1

(R)-4-(3-(4-((2,2-Dimethyl-1,3-dioxolan-4-yl)methoxy)phenyl)-4,4-dimethyl-5-oxo-2-thioxoimidazolidin-1-yl)-2-(trifluoromethyl)benzonitrile 4-(3-(4-Hydroxyphenyl)-4,4-dimethyl-5-oxo-2-thioxoimidazolidin-1-yl)-2-(trifluoromethyl)benzonitrile 14c (2.5 g, 6.20 mmol) was dissolved in 50 mL of methylbenzene, followed by addition of (R)-(2,2-dimethyl-1,3-dioxo-pentane-4-yl)methanol (819 mg, 6.20 mmol) and 1,1'-(azodicarbonyl)dipiperidine (2.5 g, 9.92 mmol), successively. The reactor was purged with argon 3 times, followed by addition of tri-n-butylphosphine (2 g, 9.92 mmol). The reaction solution was warmed up to 50° C. and stirred for 3 hours. Then, the reaction solution was concentrated under reduced pressure and the residue was purified by silica gel column chromatography with elution system E to obtain the title compound (R)-4-(3-(4-((2,2-dimethyl-1,3-dioxolan-4-yl)methoxy)phenyl)-4,4-dimethyl-5-oxo-2-thioxoimidazolidin-1-yl)-2-(trifluoromethyl)benzonitrile 44a (2.2 g, yield 68.7%) as a yellow solid.

MS m/z (ESI): 520.3 [M+1]; $^1$H NMR (400 MHz, CDCl$_3$): δ 8.38 (d, 1H), 8.29 (s, 1H), 8.08 (dd, 1H), 7.29 (d, 2H), 77.12 (d, 2H), 4.47-4.41 (m, 1H), 4.14-4.03 (m, 3H), 3.81-3.32 (m, 1H), 1.50 (s, 6H), 1.37 (s, 3H), 1.32 (s, 3H).

Step 2

(S)-4-(3-(4-(2,3-Dihydroxypropoxy)phenyl)-4,4-dimethyl-5-oxo-2-thioxoimidazolidin-1-yl)-2-(trifluoromethyl)benzonitrile (R)-4-(3-(4-((2,2-Dimethyl-1,3-dioxolan-4-yl)methoxy)phenyl)-4,4-dimethyl-5-oxo-2-thioxoimidazolidin-1-yl)-2-(trifluoromethyl)benzonitrile 44a (2.2 g, 4.20 mmol) was dissolved in 100 mL of acetic acid, followed by addition of 50 mL of H$_2$O. The reaction solution was warmed up to 70° C. and stirred for 1 hour. Then, the reaction solution was concentrated under reduced pressure to remove residual acetic acid, mixed with H$_2$O (100 mL) and ethyl acetate (100 mL), and left to stand and separate. The organic phases were washed with saturated sodium bicarbonate solution (100 mL×2), dried over anhydrous sodium sulfate, and filtered. The filtrate was concentrated under reduced pressure, and the residue was purified by silica gel column chromatography with elution system A to obtain the title compound (S)-4-(3-(4-(2,3-dihydroxypropoxy)phenyl)-4,4-dimethyl-5-oxo-2-thioxoimidazolidin-1-yl)-2-(trifluoromethyl)benzonitrile 44 (1.1 g, yield 55.0%) as a white solid.

MS m/z (ESI): 480.3 [M+1]; $^1$H NMR (400 MHz, CDCl$_3$): δ 8.02-8.00 (m, 2H), 7.89-7.87 (m, 1H), 7.30-7.25 (m, 2H), 7.11-7.09 (m, 2H), 4.20-4.14 (m, 3H), 3.91-3.80 (m, 2H), 2.61-2.60 (d, 1H), 2.02-1.99 (m, 1H), 1.61 (s, 6H).

Example 45

(R)-4-(3-(4-(2,3-Dihydroxypropoxy)phenyl)-4,4-dimethyl-5-oxo-2-thioxoimidazolidin-1-yl)-2-(trifluoromethyl)benzonitrile

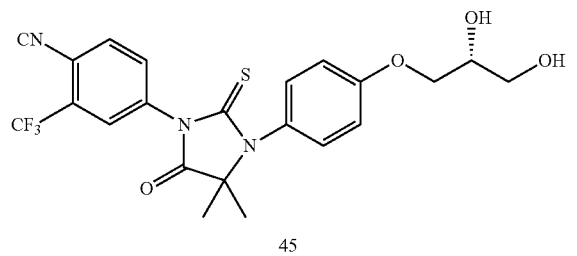

45

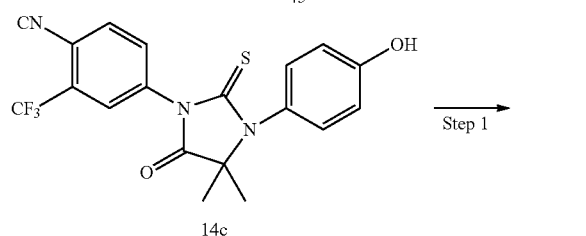

14c

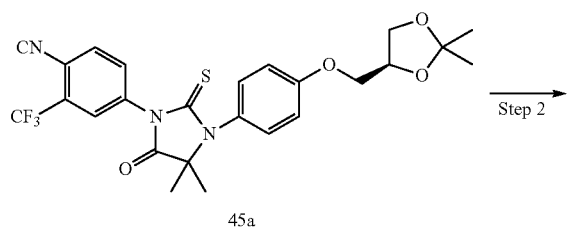

45a

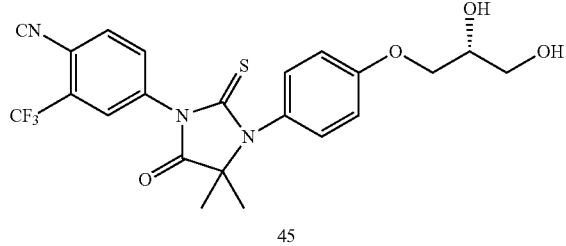

45

Step 1

(S)-4-(3-(4-((2,2-Dimethyl-1,3-dioxolan-4-yl)methoxy)phenyl)-4,4-dimethyl-5-oxo-2-thioxoimidazolidin-1-yl)-2-(trifluoromethyl)benzonitrile 4-(3-(4-Hydroxyphenyl)-4,4-dimethyl-5-oxo-2-thioxoimidazolidin-1-yl)-2-(trifluoromethyl)benzonitrile 14c (2.5 g, 6.20 mmol) was dissolved in 50 mL of methylbenzene, followed by addition of (S)-(2,2-dimethyl-1,3-dioxo-pentane-4-yl)methanol (819 mg, 6.20 mmol) and 1,1'-(azodicarbonyl)dipiperidine (2.5 g, 9.92 mmol), successively. The reactor was purged with argon 3 times, followed by addition of tri-n-butylphosphine (2 g, 9.92 mmol). The reaction solution was warmed up to 50° C. and stirred for 3 hours. Then, the reaction solution was concentrated under reduced pressure, and the residue was purified by silica gel column chromatography with elution system E to obtain the title compound (S)-4-(3-(4-((2,2-dimethyl-1,3-dioxolan-4-yl)methoxy)phenyl)-4,4-dimethyl-5-oxo-2-thioxoimidazolidin-1-yl)-2-(trifluoromethyl)benzonitrile 45a (2.5 g, yield 78.1%) as a yellow solid.

MS m/z (ESI): 520.3 [M+1]

Step 2

(R)-4-(3-(4-(2,3-Dihydroxypropoxy)phenyl)-4,4-dimethyl-5-oxo-2-thioxoimidazolidin-1-yl)-2-(trifluoromethyl)benzonitrile (S)-4-(3-(4-((2,2-Dimethyl-1,3-dioxolan-4-yl)methoxy)phenyl)-4,4-dimethyl-5-oxo-2-thioxoimidazolidin-1-yl)-2-(trifluoromethyl)benzonitrile 45a (2.5 g, 4.80 mmol) was dissolved in 100 mL of acetic acid, followed by addition of 50 mL of H$_2$O. The reaction solution was warmed up to 70° C. and stirred for 1 hour. Then, the reaction solution was concentrated under reduced pressure to remove residual acetic acid, mixed with H$_2$O (100 mL) and ethyl acetate (100 mL), and left to stand and separate. The organic phases were washed with saturated sodium bicarbonate solution (100 mL×2), dried over anhydrous sodium sulfate, and filtered. The filtrate was concentrated under reduced pressure, and the residue was purified by silica gel column chromatography with elution system A to obtain the title compound (R)-4-(3-(4-(2,3-dihydroxypropoxy)phenyl)-4,4-dimethyl-5-oxo-2-thioxoimidazolidin-1-yl)-2-(trifluoromethyl)benzonitrile 45 (1.32 g, yield 57.3%) as a white solid.

MS m/z (ESI): 480.3 [M+1]; $^1$H NMR (400 MHz, CDCl$_3$): δ 7.99-7.97 (m, 2H), 7.86-7.83 (m, 1H), 7.24-7.22 (m, 2H), 7.08-7.06 (m, 2H), 4.15-4.10 (m, 3H), 3.88-3.78 (m, 2H), 2.59-2.58 (d, 1H), 2.02-1.99 (m, 1H), 1.59 (s, 6H).

Example 46

4-(3-(4-((1-Acetyl-4-hydroxypyrrolidin-3-yl)oxy)-3-fluorophenyl)-4,4-dimethyl-5-oxo-2-thioxoimidazolidin-1-yl)-2-(trifluoromethyl)benzonitrile

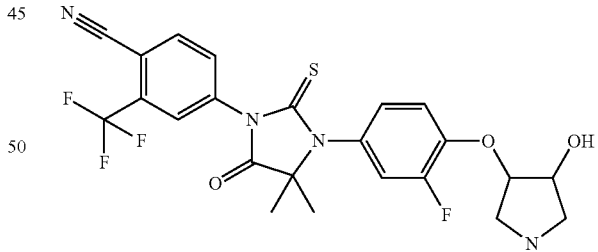

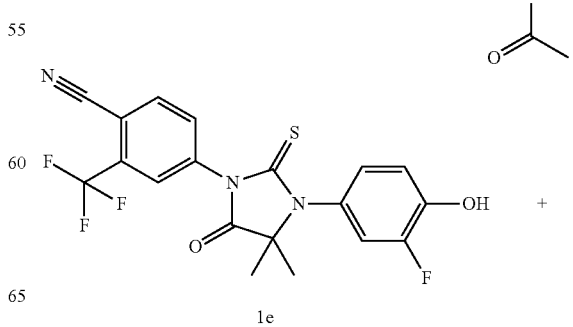

1e

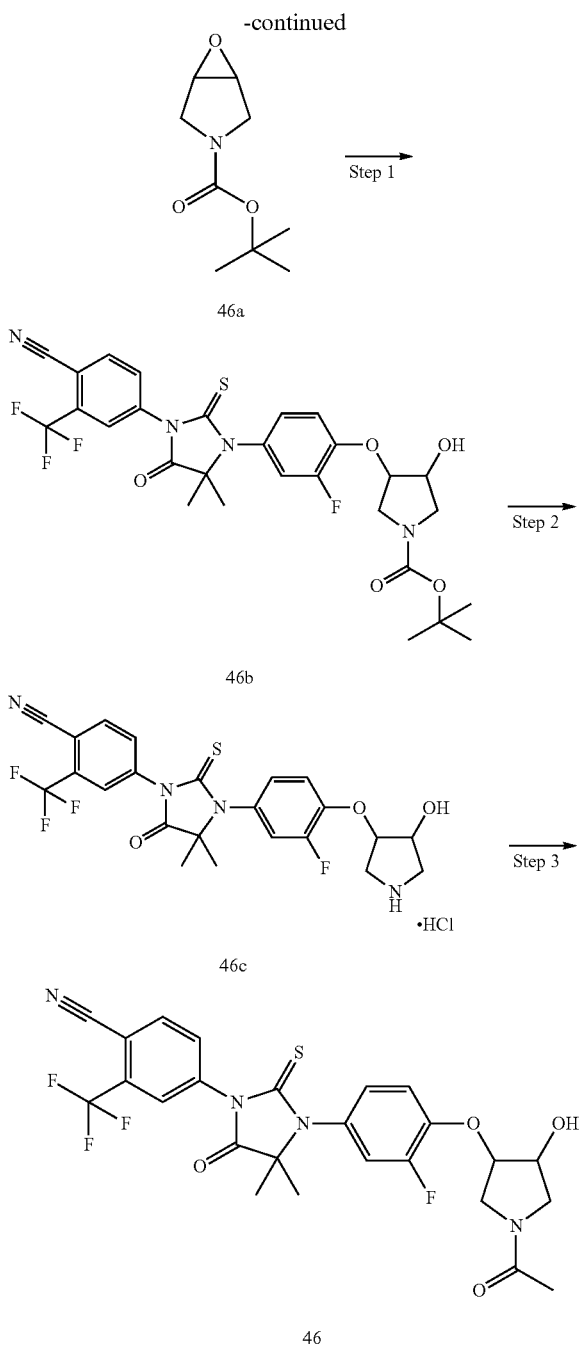

reaction solution was naturally cooled down to room temperature, mixed with H$_2$O (50 mL) and ethyl acetate (50 mL), and separated. The organic phases were washed with saturated sodium chloride solution (50 mL×2), dried over anhydrous sodium sulfate, and filtered to remove the drying agent. The filtrate was concentrated under reduced pressure, and the residue was purified by thin layer chromatography with elution system C to obtain the title compound tert-butyl 3-(4-(3-(4-cyano-3-(trifluoromethyl)phenyl)-5,5-dimethyl-4-oxo-2-thioxoimidazolidin-1-yl)-2-fluorophenoxy)-4-hydroxypyrrolidine-1-carboxylate 46b (280 mg, yield 92.1%) as a pale yellow solid.

MS m/z (ESI): 553.3 [M−56+1]

Step 2

4-(3-(3-Fluoro-4-((4-hydroxypyrrolidin-3-yl)oxy)phenyl)-4,4-dimethyl-5-oxo-2-thioxoimidazolidin-1-yl)-2-(trifluoromethyl)benzonitrile hydrochloride tert-Butyl 3-(4-(3-(4-cyano-3-(trifluoromethyl)phenyl)-5,5-dimethyl-4-oxo-2-thioxoimidazolidin-1-yl)-2-fluorophenoxy)-4-hydroxypyrrolidine-1-carboxylate 46b (280 mg, 0.46 mmol) was dissolved in 50 mL of methanol, followed by addition of a solution of hydrochloric acid in methanol (2%, 5 mL). The reaction solution was stirred for 4 hours, then concentrated under reduced pressure to obtain the title compound 4-(3-(3-fluoro-4-((4-hydroxypyrrolidin-3-yl)oxy)phenyl)-4,4-dimethyl-5-oxo-2-thioxoimidazolidin-1-yl)-2-(trifluoromethyl)benzonitrile hydrochloride 46c (230 mg, yield 98.3%) as a pale yellow solid.

MS m/z (ESI): 509.3 [M+1]; $^1$H NMR (400 MHz, DMSO): δ 9.62 (m, 2H), 8.40-8.36 (m, 1H), 8.28-8.27 (m, 1H), 8.08-8.06 (m, 1H), 7.57-7.53 (m, 1H), 7.41-7.37 (m, 1H), 7.23-7.21 (m, 1H), 4.99-4.98 (m, 1H), 4.43-4.42 (m, 1H), 3.67-3.63 (m, 1H), 3.36-3.30 (m, 2H), 2.25-2.16 (m, 1H), 1.51 (s, 6H).

Step 3

4-(3-(4-((1-Acetyl-4-hydroxypyrrolidin-3-yl)oxy)-3-fluorophenyl)-4,4-dimethyl-5-oxo-2-thioxoimidazolidin-1-yl)-2-(trifluoromethyl)benzonitrile 4-(3-(3-Fluoro-4-((4-hydroxypyrrolidin-3-yl)oxy)phenyl)-4,4-dimethyl-5-oxo-2-thioxoimidazolidin-1-yl)-2-(trifluoromethyl)benzonitrile hydrochloride 46c (80 mg, 0.16 mmol), triethylamine (14 mg, 0.18 mmol), and 4-dimethylaminopyridine (2 mg, 0.02 mmol) were added to 5 mL of dichloromethane, successively, and mixed well, followed by addition of acetylchloride. The reaction solution was stirred for 2 hours, concentrated under reduced pressure, and the residue was purified by thin layer chromatography with elution system C to obtain the title compound 4-(3-(4-((1-acetyl-4-hydroxypyrrolidin-3-yl)oxy)-3-fluorophenyl)-4,4-dimethyl-5-oxo-2-thioxoimidazolidin-1-yl)-2-(trifluoromethyl)benzonitrile 46 (15 mg, yield 18.8%) as a white solid.

MS m/z (ESI): 551.3 [M+1]; $^1$H NMR (400 MHz, CDCl3): δ 8.00-7.95 (m, 2H), 7.84-7.82 (m, 1H), 7.15-7.06 (m, 3H), 4.86-4.78 (m, 1H), 4.63-4.53 (m, 1H), 3.99-3.89 (m, 2H), 3.77-3.73 (m, 1H), 3.69-3.56 (m, 1H), 2.12 (s, 3H), 1.60 (s, 6H).

Step 1 tert-Butyl 3-(4-(3-(4-cyano-3-(trifluoromethyl)phenyl)-5,5-dimethyl-4-oxo-2-thioxoimidazolidin-1-yl)-2-fluorophenoxy)-4-hydroxypyrrolidine-1-carboxylate 4-(3-(3-Fluoro-4-hydroxyphenyl)-4,4-dimethyl-5-oxo-2-thioxoimidazolidin-1-yl)-2-(trifluoromethyl)benzonitrile 1e (212 mg, 0.50 mmol) was placed in a reaction flask, followed by addition of tert-butyl 6-oxa-3-azabicyclo[3.1.0]hexane-3-carboxylate 46a (463 mg, 2.5 mmol) and 0.5 mL of N,N-diisopropylethylamine. The reaction solution was warmed up to 100° C. and stirred for 16 hours. Then, the

Example 47

4-(3-(3-Fluoro-4-((4-hydroxy-1-methylpyrrolidin-3-yl)oxy)phenyl)-4,4-dimethyl-5-oxo-2-thioxoimidazolidin-1-yl)-2-(trifluoromethyl)benzonitrile

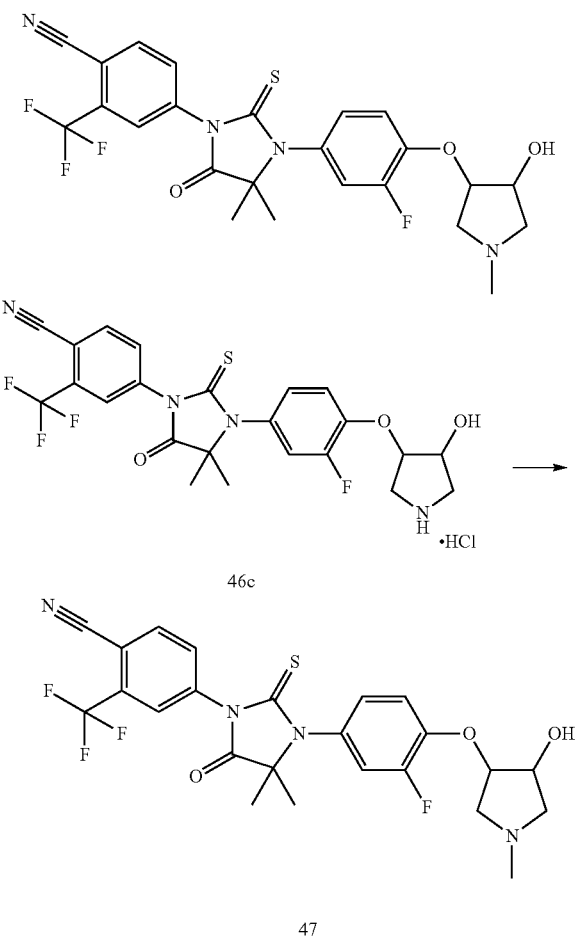

46c

47

Sodium cyanoborohydride (35 mg, 0.55 mmol) and zinc chloride (37 mg, 0.28 mmol) were added to 3 mL of methanol and mixed well, followed by addition of 4-(3-(3-fluoro-4-((4-hydroxypyrrolidin-3-yl)oxy)phenyl)-4,4-dimethyl-5-oxo-2-thioxoimidazolidin-1-yl)-2-(trifluoromethyl) benzonitrile hydrochloride 46c (100 mg, 0.18 mmol) and formaldehyde (1 mL). The reaction solution was stirred for 16 hours, mixed with H$_2$O (50 mL) and ethyl acetate (50 mL), and separated. The organic phases were washed with saturated sodium chloride solution (50 mL×2), dried over anhydrous sodium sulfate, and filtered to remove the drying agent. The filtrate was concentrated under reduced pressure, and the residue was purified by thin layer chromatography with elution system A to obtain the title compound 4-(3-(3-fluoro-4-(4-hydroxy-1-methylpyrrolidin-3-yl)oxy)phenyl)-4,4-dimethyl-5-oxo-2-thioxoimidazolidin-1-yl)-2-(trifluoromethyl)benzonitrile 47 (35 mg, yield 36.5%) as a white solid.

MS m/z (ESI): 523.4 [M+1]; $^1$H NMR (400 MHz, CDCl3): δ 7.99-7.96 (m, 2H), 7.84-7.82 (m, 1H), 7.25-7.23 (m, 1H), 7.08-7.03 (m, 2H), 4.70 (m, 1H), 4.33 (m, 1H), 3.42-3.38 (m, 1H), 2.86-2.79 (m, 2H), 2.63-2.59 (m, 1H), 2.45 (s, 3H), 1.59 (s, 6H).

Example 48

4-(3-(4-(2,3-Dihydroxypropoxy)phenyl)-4,4-dimethyl-5-oxo-2-thioxoimidazolidin-1-yl)-2-(trifluoromethyl)benzonitrile

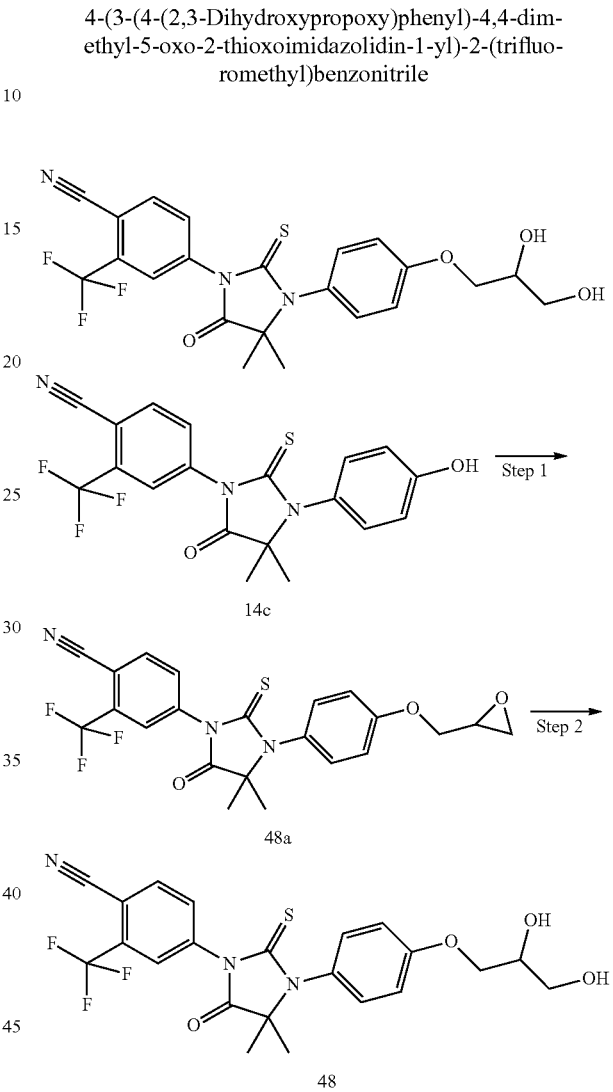

14c

48a

48

Step 1

4-(4,4-Dimethyl-3-(4-(oxiran-2-ylmethoxy)phenyl)-5-oxo-2-thioxoimidazolidin-1-yl)-2-(trifluoromethyl) benzonitrile 4-(3-(4-Hydroxyphenyl)-4,4-dimethyl-5-oxo-2-thioxoimidazolidin-1-yl)-2-(trifluoromethyl)benzonitrile 14c (4.5 g, 11.1 mmol) was dissolved in 50 mL of acetonitrile, followed by addition of epoxy chloropropane (2.05 g, 22.2 mmol) and potassium carbonate (3.8 g, 27.8 mmol), successively. The reaction solution was warmed up to 80° C. and refluxed for 16 hours. The reaction solution was cooled down to room temperature, mixed with 100 mL of water and extracted with ethyl acetate (100 mL×2). The organic phases were combined, washed with saturated sodium chloride solution (100 mL×2), dried over anhydrous sodium sulfate, and filtered. The filtrate was concentrated under the reduced pressure and the residue was purified by silica gel column chromatography with elution system C to obtain the title compound 4-(4,4-dimethyl-3-(4-(oxiran-2-ylmethoxy)phenyl)-5-oxo-2-thioxoimidazolidin-1-yl)-2-(trifluoromethyl)benzonitrile 48a (3.0 g, yield 58.8%) as a colourless oil.

MS m/z (ESI): 480.3 [M+1]

Step 2

4-(3-(4-(2,3-Dihydroxypropoxy)phenyl)-4,4-dimethyl-5-oxo-2-thioxoimidazolidin-1-yl)-2-(trifluoromethyl)benzonitrile 4-(4,4-Dimethyl-3-(4-(oxiran-2-ylmethoxy)phenyl)-5-oxo-2-thioxoimidazolidin-1-yl)-2-(trifluoromethyl)benzonitrile 48a (2.9 g, 6.3 mmol) was dissolved in 80 mL of a mixture of water and tetrahydrofuran (v/v=1:1), followed by addition of concentrated sulfuric acid (2.0 mL). The reaction solution was stirred for 4 hours, mixed with hydrochloric acid (1M, 50 mL), and extracted with ethyl acetate (100 mL×2). The organic phases were combined, washed with saturated sodium chloride solution (100 mL×2), dried over anhydrous sodium sulfate, and filtered. The filtrate was concentrated under reduced pressure, and the residue was purified by silica gel column chromatography with elution system A to obtain the title compound 4-(3-(4-(2,3-dihydroxypropoxy)phenyl)-4,4-dimethyl-5-oxo-2-thioxoimidazolidin-1-yl)-2-(trifluoromethyl)benzonitrile 48 (1.1 g, yield 36.7%) as a white solid.

MS m/z (ESI): 480.3 [M+1]; $^1$H NMR (400 MHz, CDCl3): δ 7.99-7.97 (m, 2H), 7.86-7.84 (m, 1H), 7.27-7.22 (m, 2H), 7.08-7.06 (m, 2H), 4.16-4.10 (m, 3H), 3.87-3.78 (m, 2H), 1.58 (s, 6H).

Example 49 and Example 50

(S)-4-(3-(4-(2,3-Dihydroxypropoxy)-3-fluorophenyl)-4,4-dimethyl-5-oxo-2-thioxoimidazolidin-1-yl)-2-(trifluoromethyl)benzonitrile 49

(R)-4-(3-(4-(2,3-Dihydroxypropoxy)-3-fluorophenyl)-4,4-dimethyl-5-oxo-2-thioxoimidazolidin-1-yl)-2-(trifluoromethyl)benzonitrile 50

The racemate 4-(3-(4-(2,3-dihydroxypropoxy)-3-fluorophenyl)-4,4-dimethyl-5-oxo-2-thioxoimidazolidin-1-yl)-2-(trifluoromethyl)benzonitrile 48 (1.6 g, white solid) was chirally separated by preparation equipments and a chiral column by HPLC (separation condition: chiral column CHIRALPAK AD-H, column size: 3 cm I.D.×25 cm L, mobile phase: n-hexane:isopropanol=80:20 (v/v), flow rate: 25 mL/minute). The corresponding fractions were collected, and evaporated to remove the solvent to obtain the title product (S)-4-(3-(4-(2,3-dihydroxypropoxy)-3-fluorophenyl)-4,4-dimethyl-5-oxo-2-thioxoimidazolidin-1-yl)-2-(trifluoromethyl)benzonitrile 49 (745 mg, yield 46.6%) as a white solid, and (R)-4-(3-(4-(2,3-dihydroxypropoxy)-3-fluorophenyl)-4,4-dimethyl-5-oxo-2-thioxoimidazolidin-1-yl)-2-(trifluoromethyl)benzonitrile 50 (796 mg, yield 49.8%) as a white solid.

49: MS m/z (ESI): 498.3 [M+1]; $^1$H NMR (400 MHz, CDCl3): δ 7.99-7.95 (m, 2H), 7.84-7.82 (m, 1H), 7.15-7.04 (m, 3H), 4.22-4.18 (m, 3H), 3.91-3.79 (m, 2H), 1.59 (s, 6H).

50: MS m/z (ESI): 498.3 [M+1]; $^1$H NMR (400 MHz, CDCl3): δ 7.99-7.95 (m, 2H), 7.84-7.82 (m, 1H), 7.15-7.04 (m, 3H), 4.22-4.18 (m, 3H), 3.91-3.79 (m, 2H), 1.59 (s, 6H).

Example 51

4-(3-(4-Cyano-3-(trifluoromethyl)phenyl)-5,5-dimethyl-4-oxo-2-thioxoimidazolidin-1-yl)-2-fluorophenyl trifluoromethanesulfonate

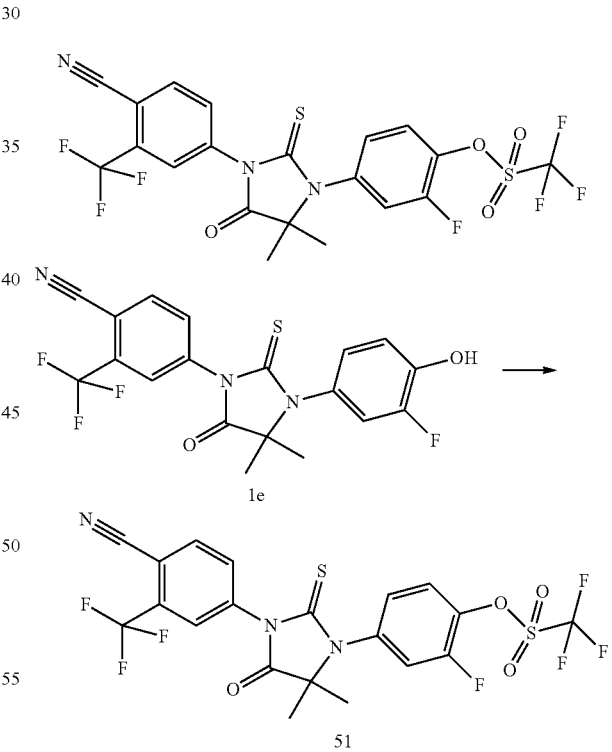

4-(3-(3-Fluoro-4-hydroxyphenyl)-4,4-dimethyl-5-oxo-2-thioxoimidazolidin-1-yl)-2-(trifluoromethyl)benzonitrile 1e (200 mg, 0.47 mmol) was dissolved in 4 mL of dichloromethane in an ice bath, followed by addition of triethylamine (0.2 mL, 1.42 mmol) and trifluoromethanesulfonic acid (160 mg, 0.57 mmol). The reactor was purged with argon 3 times and stirred for 1 hour, followed by addition of 20 mL of a mixture of dichloromethane and water (v/v=1:1).

The reaction solution was separated, and the aqueous phase was extracted with dichloromethane (10 mL×3). The organic phases were combined, washed with saturated sodium chloride solution (20 mL×2), dried over anhydrous sodium sulfate, and filtered. The filtrate was concentrated under reduced pressure to obtain the title compound 4-(3-(4-cyano-3-(trifluoromethyl)phenyl)-5,5-dimethyl-4-oxo-2-thioxoimidazolidin-1-yl)-2-fluorophenyl trifluoromethanesulfonate 51 (250 mg, yield 95.3%) as a brown solid.

MS m/z (ESI): 614.1 [M+1]; $^1$H NMR (400 MHz, CDCl3): δ 8.01-7.95 (m, 2H), 7.84-7.83 (m, 1H), 7.57-7.52 (m, 1H), 7.32-7.29 (m, 1H), 7.27-7.24 (m, 1H), 1.59 (s, 6H).

Test Examples

Biological Assay

The invention will be further illustrated with reference to the following test examples. It is to be understood that these examples are merely intended to demonstrate the invention without limiting the scope of the invention.

The experimental methods in the following examples for which no specific conditions are indicated were carried out under conventional conditions, or under those conditions suggested by the manufacturers. The experimental reagents for which no specific sources are indicated were conventional reagents generally purchased from the market.

Test Example 1

Biological Evaluation of Inhibitory Activity on PSA Secretion of LNCaP Cells

The following in vitro assay was performed to determine the activity of the compounds of the present invention for inhibiting prostate specific antigen (PSA) secretion of LNCaP cells.

1. Material & Apparatus
  (1). RIPM 1640 culture medium (Hyclone, SH30809.01B)
  (2). Fetal calf serum, FBS (GIBCO, 10099)
  (3). Pen Strep (GIBCO, 15140-122)
  (4). CS-FBS (SERANA, 1090111)
  (5). LNCaP cell (Cell bank of the Chinese Academy of Sciences, TCHu173)
  (6). Testosterone (Dr. Ehrenstorfer Gmbh, C 17322500, LOT: 10519)
  (7). PSA kit (Abnova, KA0208)
  (8). NOVO Star microplate reader
  (9). Cell culture: RIPM 1640 culture medium, 10% FBS, 1% Pen Strep
  (10). Active carbon culture medium: RIPM 1640 culture medium, 10% CS-FBS, 1% Pen Strep
  (11). Testosterone culture medium: RIPM 1640 culture medium, 10% CS-FBS, 1% Pen Strep, 1 nM testosterone 2. Experimental Procedure LNCaP cells were subcultured in cell culture medium, resuspended in active carbon culture medium, and then inoculated into a 96-well plate (100 μl/well) with an inoculation density of 5×10$^4$ cells/well.

The test compounds were dissolved in DMSO (dimethyl sulfoxide) and prepared as a 10 mM stock solution. When used, the stock solution was diluted with 5×DMSO and then diluted with a threefold gradient to obtain 8 gradient concentrations. Then, the 8 gradient concentrations were each diluted with 20× testosterone culture medium, in order to ensure DMSO concentration in each culture system was 0.5%. Diluted test compounds remained to be tested.

10 μl of diluted test compounds were added to a 96-well plate and mixed gently. 10 μl of 0.5% DMSO diluted with active carbon culture medium was added to the blank group, and 10 μl of 0.5% DMSO diluted with testosterone culture medium was added to the control group. The 96-well plate was cultured in an incubator under the conditions of 37° C. and 5% $CO_2$.

3. Test Results

After 4 days of incubation, 60 μl of cell cultural supernatants were collected, and the OD450 value per well was measured on a NOVO Star microplate reader using PSA kit (Abnova, KA0208).

$IC_{50}$ values were calculated from the data of the inhibition rates of the test compounds at various concentrations.

| Example No. | IC50(nM) |
| --- | --- |
| 1 | 34 |
| 2 | 45 |
| 3 | 35 |
| 4 | 93 |
| 5 | 124 |
| 6 | 24 |
| 7 | 23 |
| 8 | 21 |
| 9 | 26 |
| 10 | 23 |
| 11 | 35 |
| 12 | 33 |
| 13 | 88 |
| 14 | 19 |
| 15 | 52 |
| 16 | 12 |
| 17 | 24 |
| 19 | 94 |
| 20 | 57 |
| 21 | 76 |
| 22 | 21 |
| 23 | 24 |
| 24 | 32 |
| 25 | 31 |
| 26 | 44 |
| 27 | 83 |
| 28 | 82 |
| 29 | 85 |
| 30 | 17 |
| 32 | 110 |
| 34 | 51 |
| 35 | 57 |
| 36 | 23 |
| 37 | 23 |
| 38 | 33 |
| 39 | 27 |
| 40 | 29 |
| 41 | 24 |
| 44 | 22 |
| 45 | 35 |
| 46 | 47 |
| 47 | 21 |
| 48 | 37 |
| 49 | 35 |
| 50 | 43 |

Conclusion: The test results demonstrated that the preferred compounds of the present invention had significant activity for inhibiting PSA secretion of LNCaP cells.

Test Example 2

Biological Evaluation on Proliferation Inhibition of LNCaP Cells

The following in vitro assay was performed to determine the activity of the compounds of the present invention for inhibiting the proliferation of LNCaP cells.

1. Material & Apparatus:
(1). Cell counting reagent CCK-8 (DOJINDO, CK04)
(2). Victor3 microplate reader (Perkin Elmer, 1420)
2. Experimental Procedure
See experimental procedure from Test Example 1.
3. Test Results After LNCaP cells were cultured for 3 days, the culture medium, test compounds, blank group, and control group were renewed with half of the liquid volume, and were cultured for another 3 days. Then, all 96-well plates were mixed gently with 10 μl of CCK-8 and cultured in an incubator for 2-3 hours under the conditions of 37° C. and 5% $CO_2$. The OD value per well was measured at 450 nm on a Victor3 microplate reader.

$IC_{50}$ values were calculated from the data of the inhibition rates of the test compounds at various concentrations.

| Example No. | IC50(nM) |
| --- | --- |
| 1 | 195 |
| 2 | 97 |
| 3 | 46 |
| 5 | 87 |
| 6 | 99 |
| 7 | 23 |
| 8 | 75 |
| 9 | 162 |
| 10 | 131 |
| 11 | 93 |
| 12 | 146 |
| 13 | 61 |
| 14 | 253 |
| 16 | 78 |
| 17 | 68 |
| 19 | 194 |
| 20 | 156 |
| 21 | 92 |
| 22 | 134 |
| 23 | 180 |
| 24 | 92 |
| 25 | 111 |
| 26 | 201 |
| 28 | 79 |
| 29 | 80 |
| 30 | 58 |
| 32 | 134 |
| 34 | 159 |
| 35 | 277 |
| 36 | 115 |
| 37 | 63 |
| 39 | 256 |
| 40 | 196 |
| 41 | 283 |
| 44 | 33 |
| 45 | 74 |
| 48 | 281 |
| 49 | 203 |
| 50 | 196 |

Conclusion: The preferred compounds of the present invention had significant activity for inhibiting the proliferation of LNCaP cells.

Test Example 3

Biological Evaluation of LNCaP-AR Cells

The following in vitro assay was performed to determine the activity of a high concentration of the compounds of the present invention for agitating the PSA secretion of LNCaP-AR cells (AR-overexpressed LNCaP cells, referred to as "LNCaP-AR cells" for short, constructed by a retroviral transfection method).

1. Cell Culture

LNCaP-AR cells were subcultured in cell culture medium, resuspended in active carbon culture medium, and then inoculated into a 96-well plate (100 μl/well) with an inoculation density of $5 \times 10^4$ cells/well.

The test compounds were dissolved in DMSO (dimethyl sulfoxide) and prepared as a 10 mM stock solution. When used, the stock solution was diluted with DMSO into the two concentrations of 2 mM and 0.6 mM. Then, the diluted concentrations were each diluted with 20× active carbon culture medium, in order to ensure DMSO concentration in each culture system was 0.5%. Diluted test compounds remained to be tested.

10 μl of diluted test compounds were added to a 96-well plate and mixed gently. 10 μl of 0.5% DMSO diluted with active carbon culture medium was added to the blank control group.

2. Test Results

After 4 days of incubation, 60 μl of cell cultural supernatants were collected, and the OD value of PSA per well was measured on a NOVO Star microplate reader using PSA kit (abnova, KA0208).

Agonist activity of the test compounds of the present invention on PSA secretion of LNCaP-AR cells was evaluated by the percentage of OD value (test compounds)/OD value (blank control). When the percentage value is greater than 100, the test compounds have agonist activity on PSA secretion of LNCaP-AR cells compared to the blank control. Conversely, when the percentage value is less than 100, the test compounds have no agonist activity on PSA secretion of LNCaP-AR cells compared to the blank control. Specific test results were as follows:

| Example compounds No. | Agonist activity (%) concentrantion | |
| --- | --- | --- |
| | 3 μM | 10 μM |
| | blank control | |
| | 100 | 100 |
| 6 | 93.20 | 99.97 |
| 8 | 65.03 | 99.5 |
| 9 | 90.77 | 85.0 |
| 10 | 74.74 | 68.10 |
| 12 | 69.58 | 90.69 |
| 13 | 53.58 | 71.49 |
| 15 | 77.48 | 84.79 |
| 44 | 77.22 | 92.67 |

Conclusion: The compounds of the present invention have no agonist activity on PSA secretion of LNCaP-AR cells.

Pharmacokinetics Assay

Test Example 4

The Pharmacokinetics Assay of the Compounds of the Present Invention

1. Abstract

Male rats were used as test animals. The compounds of Example 6, Example 9, Example 11, Example 13, Example 15, Example 16, Example 17, Example 44, and Example 45 were administered intragastrically to rats to determine the drug concentration in plasma at different time points by LC/MS/MS method. The pharmacokinetic behavior of the compounds of the present invention was studied and evaluated in rats.

2. Protocol 2.1 Samples

Compounds of Example 6, Example 9, Example 11, Example 13, Example 15, Example 16, Example 17, Example 44, and Example 45.

2.2 Test Animals 27 healthy adult male Sprague-Dawley (SD) rats, purchased from SINO-BRITISH SIPPR/BK LAB. ANIMAL LTD., CO, Certificate No.: SCXK (Shanghai) 2008-0016, were divided into 9 groups, with 3 rats in each group.

2.3 Preparation of the Test Compounds

The appropriate amount of test compounds was weighed and mixed with 0.5% CMC-Na to prepare a 0.5 mg/mL suspension by an ultrasonic method.

2.4 Administration

After an overnight fast, 27 SD rats were divided into 9 groups, and administered the compounds intragastrically at a dose of 5.0 mg/kg and an administration volume of 10 mL/kg.

3. Process

Compounds of Example 6, Example 9, Example 11, Example 13, Example 15, Example 16, Example 17, Example 44, and Example 45 were administered intragastrically to rats. Blood samples (0.1 mL) were taken from the orbital sinus before administration, and at 0.5 h, 1.0 h, 2.0 h, 3.0 h, 4.0 h, 6.0 h, 8.0 h, 11.0 h, and 24.0 h after administration, stored in heparinized tubes, and centrifuged for 5 minutes at 3,500 rpm to separate blood plasma. The plasma samples were stored at −20° C. The rats were fed 2 hours after administration.

The concentration of the different test compounds in rat plasma after intragastrically administering the test compounds was determined by LC-MS/MS method. The linearity of the method is 1.00-2000 ng/ml. Plasma samples were analyzed after protein precipitation was accomplished by the addition of methanol.

4. Results of Pharmacokinetic Parameters

Pharmacokinetic Parameters of the compounds of the present invention were as follows:

| | Pharmacokinetics Assay (5 mg/kg) | | | | | |
|---|---|---|---|---|---|---|
| Example No | Plasma Conc. Cmax (ng/mL) | Area Under Curve AUC (ng/mL * h) | Half-Life T½ (h) | Mean Residence Time MRT (h) | Clearance CLz/F (ml/min/kg) | Apparent Distribution Volume Vz/F (ml/kg) |
| 6 | 1200 ± 330 | 16838 ± 7483 | 13.1 ± 4.6 | 17.8 ± 6.2 | 5.75 ± 2.44 | 6021 ± 1685 |
| 9 | 772 ± 83 | 18796 ± 3296 | 11.8 ± 1.1 | 18.3 ± 1.9 | 4.52 ± 0.77 | 4587 ± 556 |
| 11 | 430 ± 14 | 11450 ± 1376 | 15.8 ± 2.2/ | 23.2 ± 2.9 | 7.35 ± 0.87 | 9937 ± 633 |
| 13 | 1550 ± 197 | 26506 ± 7385 | 8.10 ± 0.65 | 13.1 ± 1.5 | 3.35 ± 1.10 | 2307 ± 553 |
| 15 | 999 ± 172 | 21406 ± 4100 | 11.7 ± 1.7 | 18.2 ± 2.3 | 3.99 ± 0.75 | 3968 ± 341 |
| 16 | 971 ± 147 | 23345 ± 5898 | 11.3 ± 1.3 | 18.4 ± 2.6 | 3.71 ± 0.84 | 3592 ± 662 |
| 17 | 864 ± 86 | 12246 ± 1517 | 6.31 ± 0.50 | 10.8 ± 0.8 | 6.88 ± 0.89 | 3759 ± 591 |
| 44 | 1300 ± 275 | 19297 ± 4170 | 6.41 ± 0.60 | 10.5 ± 1.3 | 4.47 ± 1.08 | 2450 ± 376 |
| 45 | 980 ± 173 | 13023 ± 365 | 5.90 ± 0.30 | 10.0 ± 0.6 | 6.40 ± 0.18 | 3271 ± 261 |

Conclusion: The compounds of the present invention had better pharmacokinetic data and significantly advantageous pharmacokinetic properties.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A compound of formula (I), or a tautomer, mesomer, racemate, enantiomer, diastereomer, or mixture thereof, or a pharmaceutically acceptable salt thereof:

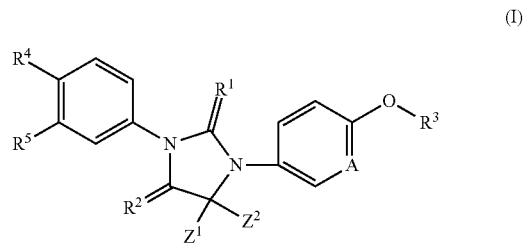

(I)

wherein:
A is —CR';
R' is hydrogen, halogen, or alkyl;
$Z^1$ and $Z^2$ are each independently alkyl;
$R^1$ is S and $R^2$ is O;
$R^3$ is alkyl
substituted with one or more groups selected from the group consisting of halogen, cyano, amino, $C_{3-6}$cycloalkyl, heterocyclyl, —OR$^6$, —C(O)NR$^7$R$^8$, —S(O)$_m$R$^6$, —C(O)R$^6$, —OC(O)R$^6$, —NR$^7$C(O)R$^8$, —NR$^7$C(O)OR$^8$, and —C(O)OR$^6$, wherein the $C_{3-6}$ cycloalkyl and heterocyclyl are each optionally substituted with one or more groups selected from the group consisting of halogen, cyano, amino, alkyl, haloalkyl, hydroxyalkyl, —OR⁶, —C(O)NR⁷R⁸, —S(O)ₘR⁶, —C(O)R⁶, —OC(O)R⁶, —NR⁷C(O)R⁸, —NR⁷C(O)OR⁸, and —C(O)OR⁶;

R⁴ and R⁵ are each independently selected from the group consisting of cyano, nitro, alkyl, haloalkyl, hydroxy, hydrogen, alkoxy, and haloalkoxy;

R⁶ is hydrogen, alkyl, halogen, or alkoxy wherein the alkyl and alkoxy are each optionally substituted with one or more groups selected from the group consisting of halogen, cyano, hydroxy, amino, oxo, alkyl, haloalkyl, hydroxyalkyl, and alkoxy;

R⁷ and R⁸ are each independently selected from the group consisting of hydrogen and alkyl, wherein the alkyl is optionally substituted with one or more groups selected from the group consisting of halogen, cyano, hydroxy, amino, oxo, alkyl, haloalkyl, hydroxyalkyl, and alkoxy; and the heterocyclyl is a 3 to 6-membered ring having 1 to 2 oxygen atoms; and m is 0, 1, or 2.

2. The compound of formula (I), or a tautomer, mesomer, racemate, enantiomer, diastereomer, or mixture thereof, or a pharmaceutically acceptable salt thereof according to claim 1, being a compound of formula (II) or a tautomer, mesomer, racemate, enantiomer, diastereomer, or mixture thereof, or a pharmaceutically acceptable salt thereof:

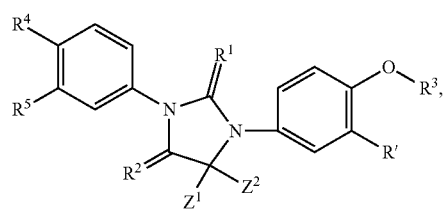

(II)

wherein R' is hydrogen or halogen.

3. The compound of formula (I), or a tautomer, mesomer, racemate, enantiomer, diastereomer, or mixture thereof, or a pharmaceutically acceptable salt thereof according to claim 1, wherein Z¹ and Z² are each methyl.

4. The compound of formula (I), or a tautomer, mesomer, racemate, enantiomer, diastereomer, or mixture thereof, or a pharmaceutically acceptable salt thereof according to claim 1, wherein R⁴ is cyano and R⁵ is haloalkyl.

5. The compound of formula (I), or a tautomer, mesomer, racemate, enantiomer, diastereomer, or mixture thereof, or a pharmaceutically acceptable salt thereof according to claim 1, wherein R³ is alkyl substituted with one or more groups selected from the group consisting of halogen, cyano, amino, C₃₋₆ cycloalkyl, heterocyclyl, —OR⁶, —C(O)NR⁷R⁸, —S(O)ₘR⁶, and —C(O)OR⁶, wherein the C₃₋₆cycloalkyl and heterocyclyl are each optionally substituted with one or more groups selected from the group consisting of halogen, cyano, amino, alkyl, haloalkyl, hydroxyalkyl, —OR⁶, —C(O)NR⁷R⁸, —S(O)ₘR⁶, and —C(O)OR⁶;

R⁶, R⁷, and R⁸ are each independently selected from the group consisting of hydrogen and alkyl, wherein the alkyl is optionally substituted with one or more groups selected from the group consisting of halogen, cyano, hydroxy, amino, oxo, alkyl, and haloalkyl;

the heterocyclyl is a 3 to 6-membered ring having 1 to 2 oxygen atoms; and m is 2.

6. The compound of formula (I), or a tautomer, mesomer, racemate, enantiomer, diastereomer, or mixture thereof, or a pharmaceutically acceptable salt thereof according to claim 1, wherein R³ is alkyl substituted with one or more groups selected from the group consisting of halogen, cyano, amino, C₃₋₆cycloalkyl, heterocyclyl, —OR⁶, —C(O)NR⁷R⁸, —S(O)ₘR⁶, and —C(O)OR⁶;

R⁶, R⁷, and R⁸ are each independently selected from the group consisting of hydrogen, alkyl, and haloalkyl;

the heterocyclyl is a 3 to 6 membered ring having 1 to 2 oxygen atoms; and m is 2.

7. The compound of formula (I), or a tautomer, mesomer, racemate, enantiomer, diastereomer, or mixture thereof, or a pharmaceutically acceptable salt thereof according to claim 1, wherein R³ is alkyl substituted with one or more hydroxy groups.

8. A compound of formula (I), or a tautomer, mesomer, racemate, enantiomer, diastereomer, or mixture thereof, or a pharmaceutically acceptable salt thereof, wherein the compound is selected from the group consisting of:

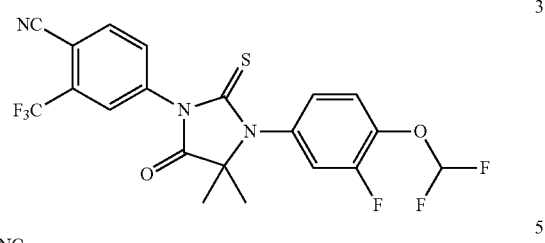

3

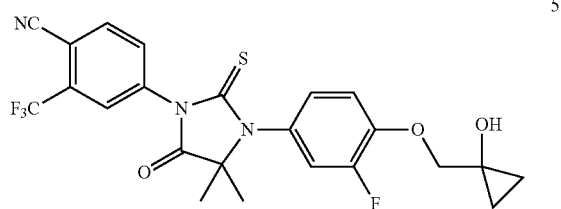

5

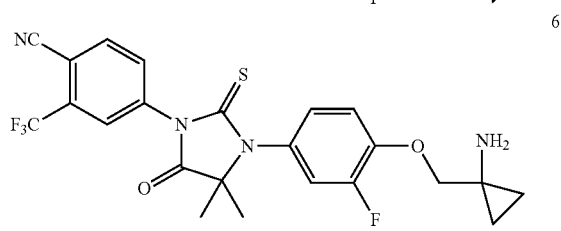

6

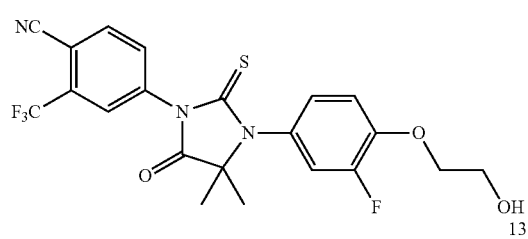

12

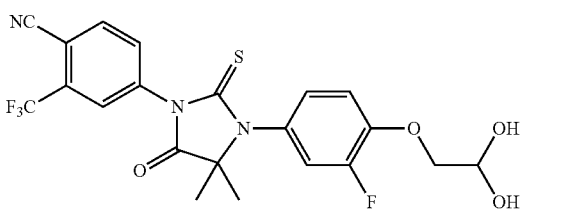

13

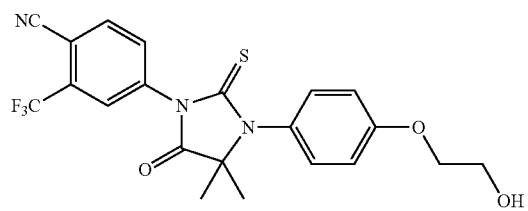
17
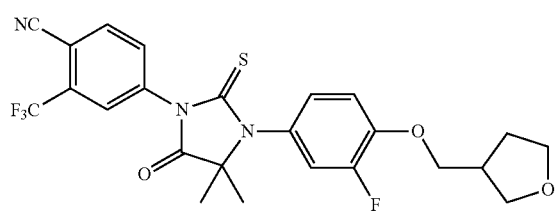
18
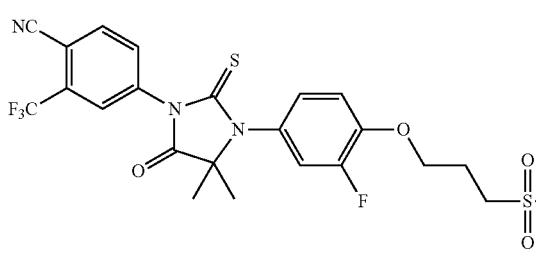
22
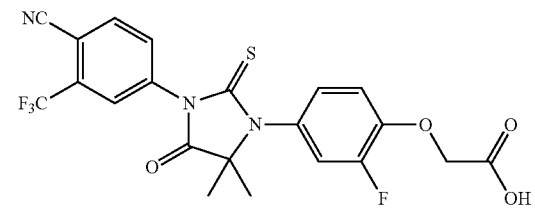
31
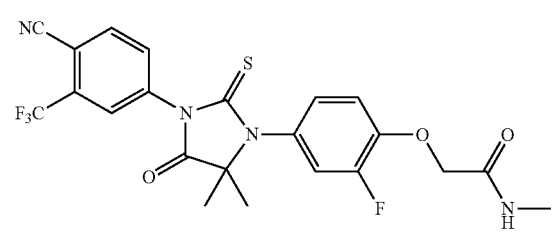
32
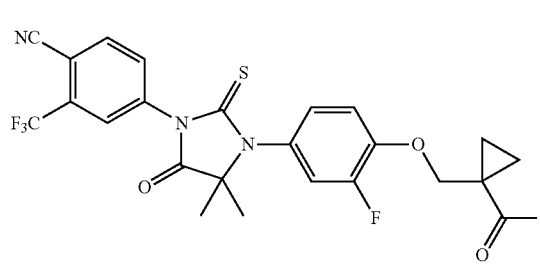
33
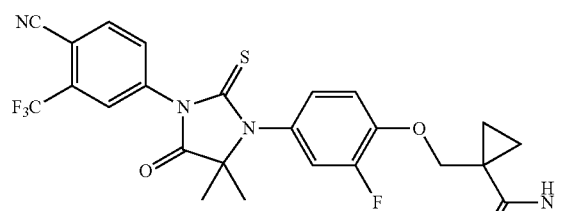
34
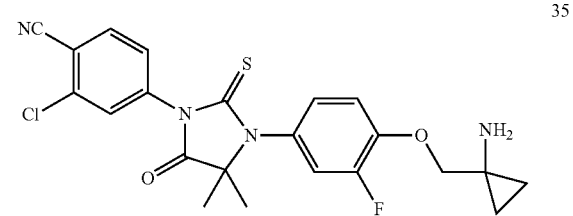
35
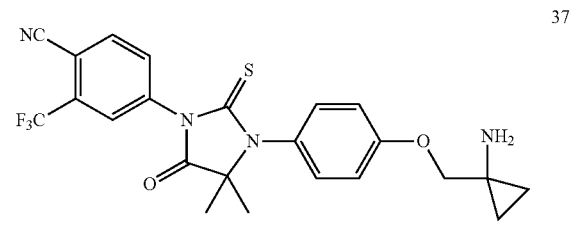
37
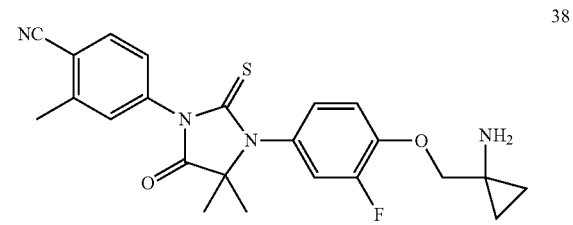
38
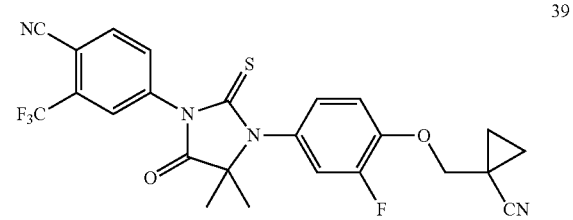
39
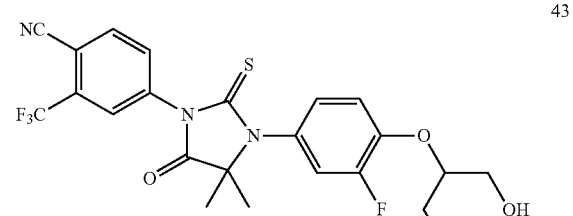
43
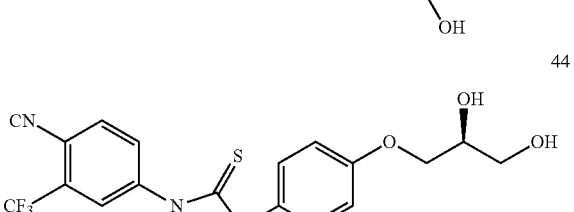
44

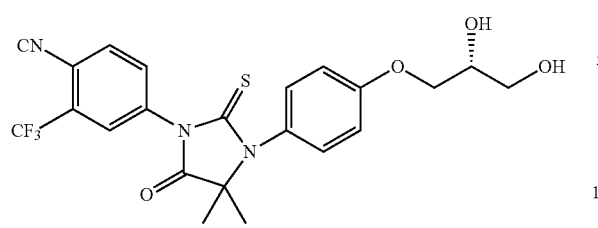
45
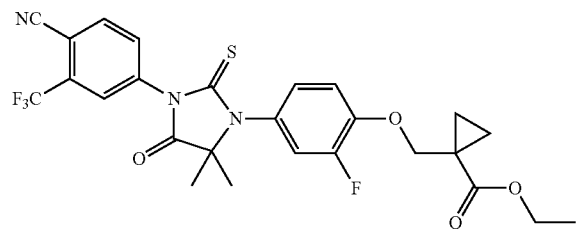
33b
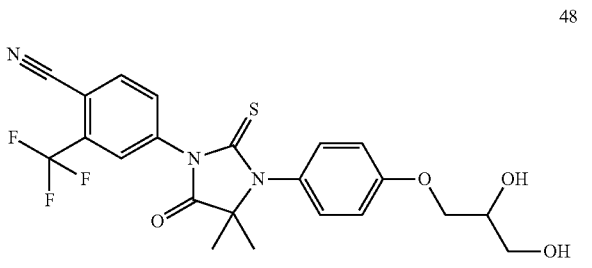
48
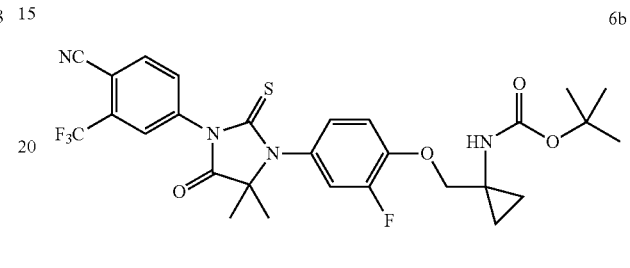
6b
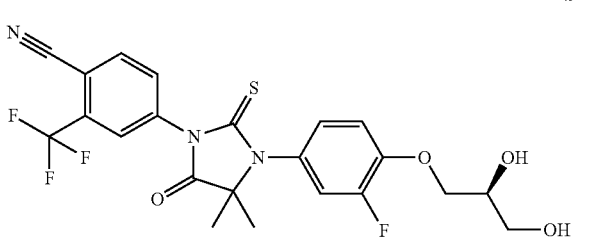
49
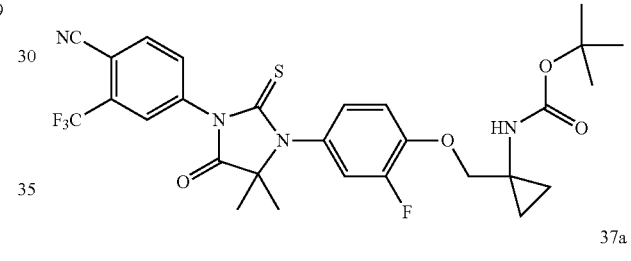
35d
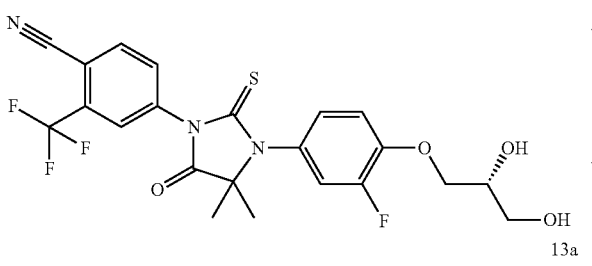
50
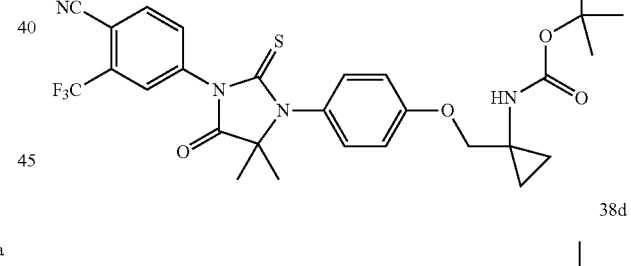
37a
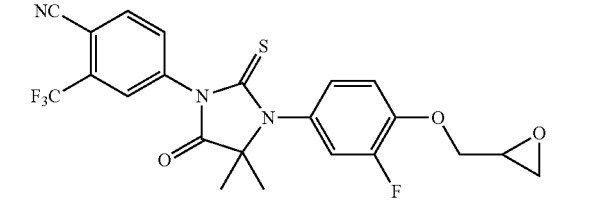
13a
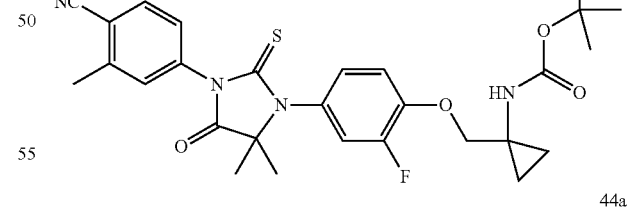
38d
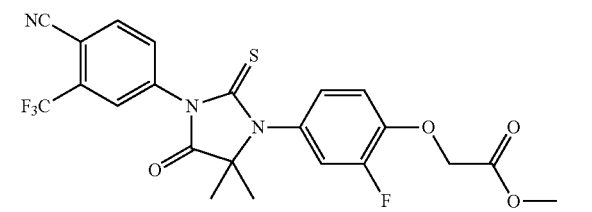
31a
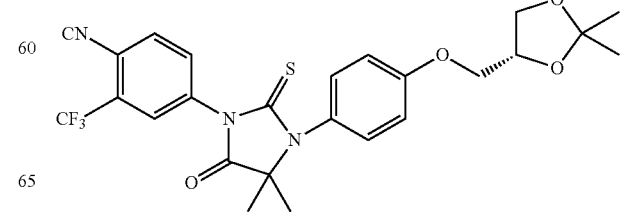
44a -continued

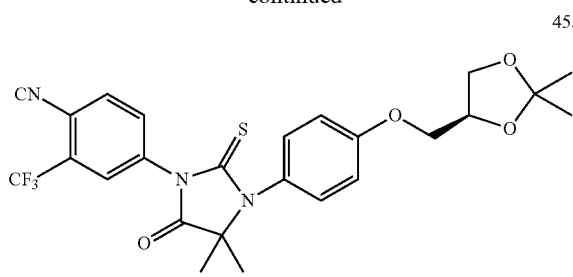

45a and

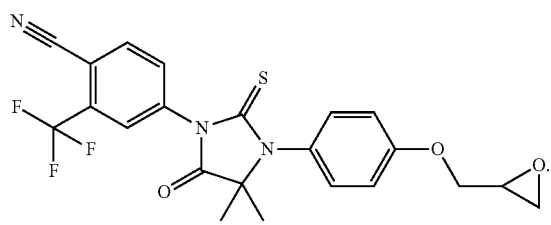

48a

9. A process of preparing the compound of formula (I) according to claim 1, or a tautomer, mesomer, racemate, enantiomer, diastereomer, or mixture thereof, or a pharmaceutically acceptable salt thereof, comprising a step of

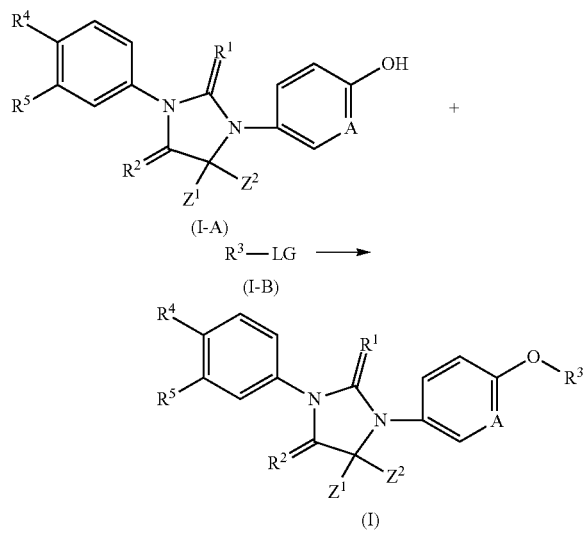

reacting a compound of formula (I-A) with a compound of formula (I-B) under an alkaline condition to obtain a compound of formula (I);

wherein LG is a leaving group.

10. A process of preparing the compound of formula (I) according to claim 1, or a tautomer, mesomer, racemate, enantiomer, diastereomer, or mixture thereof, or a pharmaceutically acceptable salt thereof, comprising a step of:

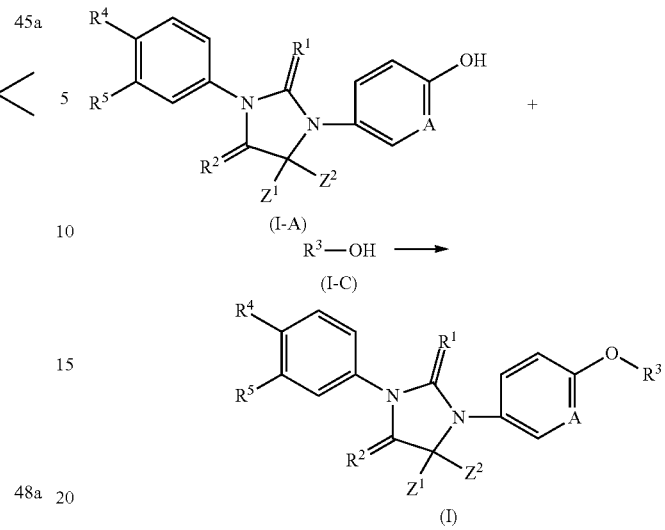

condensing a compound of formula (I-A) with a compound of formula (I-C) in the presence of triphenylphosphine or tri-n-butylphosphine, and azodicarboxylate to obtain a compound of formula (I).

11. A pharmaceutical composition comprising a therapeutically effective amount of the compound of formula (I), or a tautomer, mesomer, racemate, enantiomer, diastereomer, or mixture thereof or a pharmaceutically acceptable salt thereof according to claim 1, and a pharmaceutically acceptable carrier, diluent, or excipient.

12. The process according to claim 9, wherein the leaving group (LG) is halogen or p-toluenesulfonyloxy.

13. The process according to claim 10, wherein the azodicarboxylate is 1,1'-(azodicarbonyl)dipiperidine or diisopropyl azodicarboxylate.

14. A method for treating an androgen receptor-mediated disorder or disease, the method comprising a step of administering to a subject in need thereof a therapeutically effective amount of the pharmaceutical composition according to claim 11, wherein the androgen receptor-mediated disorder or disease is prostate cancer or prostatic hyperplasia.

15. The method according to claim 14, wherein the prostate cancer is hormone sensitive prostate cancer or hormone refractory prostate cancer.

16. A pharmaceutical composition comprising a therapeutically effective amount of the compound, or a tautomer, mesomer, racemate, enantiomer, diastereomer, or mixture thereof. or a pharmaceutically acceptable salt thereof according to claim 8, and a pharmaceutically acceptable carrier, diluent, or excipient.

17. A method for treating an androgen receptor-mediated disorder or disease, the method comprising a step of administering to a subject in need thereof a therapeutically effective amount of the pharmaceutical composition according to claim 16, wherein the androgen receptor-mediated disorder or disease is prostate cancer or prostatic hyperplasia.

18. The compound of formula (I), or a tautomer, mesomer, racemate, enantiomer, diastereomer, or mixture thereof, or a pharmaceutically acceptable salt thereof according to claim 5, wherein $R^3$ is alkyl substituted with one or more groups selected from the group consisting of halogen, cyano, amino, $C_{3-6}$cycloalkyl, —$OR^6$, —$C(O)NR^7R^8$, —$S(O)_mR^6$, and —$C(O)OR^6$, wherein the $C_{3-6}$ cycloalkyl is optionally substituted with one or more groups selected from the group consisting of halogen, cyano, amino, alkyl, haloalkyl, hydroxyalkyl, —OR$^6$, —C(O)NR$^7$R$^8$, —S(O)$_m$R$^6$, and —C(O)OR$^6$.

19. A compound of formula (I), or a tautomer, mesomer, racemate, enantiomer, diastereomer, or mixture thereof, or a pharmaceutically acceptable salt thereof:

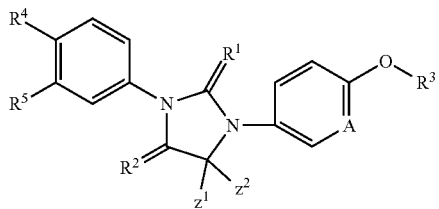

(I)

wherein:
A is —CR';
R' is hydrogen or halogen;
Z$^1$ and Z$^2$ are each independently alkyl;
R$^1$ is S;
R$^2$ is O;
R$^3$ is an alkyl group substituted with one or more groups selected from the group consisting of halogen, hydroxy, amino, cyano, —C(O)NR$^7$R$^8$, —S(O)$_m$R$^6$, —C(O)R$^6$, —C(O)OR$^6$, —NR$^7$C(O)OR$^8$, and C$_{3-6}$ cycloalkyl, wherein the C$_{3-6}$ cycloalkyl is optionally substituted with one or more groups selected from the group consisting of amino, hydroxy, alkyl, cyano, —C(O)NR$^7$R$^8$, —NR$^7$C(O)OR$^8$, and —C(O)OR$^6$;
R$^4$ and R$^5$ are each independently selected from the group consisting of cyano, alkyl, haloalkyl, and hydrogen;
R$^6$, R$^7$, and R$^8$ are each independently selected from the group consisting of hydrogen and alkyl; and
m is 2.

20. A pharmaceutical composition comprising a therapeutically effective amount of the compound of formula (I), or a tautomer, mesomer, racemate, enantiomer, diastereomer, or mixture thereof, or a pharmaceutically acceptable salt thereof according to claim 19, and a pharmaceutically acceptable carrier, diluent, or excipient.

21. A method for treating an androgen receptor-mediated disorder or disease, the method comprising a step of administering to a subject in need thereof a therapeutically effective amount of the pharmaceutical composition according to claim 20, wherein the androgen receptor-mediated disorder or disease is prostate cancer or prostatic hyperplasia.

* * * * *